US010265353B2

(12) United States Patent
Yoon et al.

(10) Patent No.: US 10,265,353 B2
(45) Date of Patent: Apr. 23, 2019

(54) **ENTEROHEMORRHAGIC *E. COLI* BACTERIOPHAGE ESC-CHP-1 AND USE THEREOF FOR INHIBITING PROLIFERATION OF ENTEROHEMORRHAGIC *E. COLI***

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); Hyoun Rok Paik, Incheon (KR); Jee Soo Son, Seoul (KR); Byung Kuk Kim, Gyeonggi-do (KR); Hee Jeong Shin, Gyeonggi-do (KR)

(73) Assignee: INTRON BIOTECHNOLOGY, INC., Gyeonggi-Do (KR)

(*) Notice: Subject to any disclaimer, the term of this patent is extended or adjusted under 35 U.S.C. 154(b) by 0 days.

(21) Appl. No.: 15/538,538

(22) PCT Filed: Dec. 28, 2015

(86) PCT No.: PCT/KR2015/014328
§ 371 (c)(1),
(2) Date: Jun. 21, 2017

(87) PCT Pub. No.: WO2016/108538
PCT Pub. Date: Jul. 7, 2016

(65) Prior Publication Data

US 2017/0333498 A1 Nov. 23, 2017

(30) Foreign Application Priority Data

Dec. 29, 2014 (KR) ........................ 10-2014-0191676

(51) Int. Cl.

| | |
|---|---|
| ***C12N 7/00*** | (2006.01) |
| ***A23K 10/18*** | (2016.01) |
| ***A61K 35/76*** | (2015.01) |
| ***A23K 20/195*** | (2016.01) |
| ***A23K 50/30*** | (2016.01) |
| ***A23K 20/10*** | (2016.01) |
| ***A23K 50/60*** | (2016.01) |
| ***A61P 31/04*** | (2006.01) |

(52) U.S. Cl.
CPC .............. *A61K 35/76* (2013.01); *A23K 10/18* (2016.05); *A23K 20/10* (2016.05); *A23K 20/195* (2016.05); *A23K 50/30* (2016.05); *A23K 50/60* (2016.05); *A61P 31/04* (2018.01); *C12N 7/00* (2013.01); *C12N 2795/10132* (2013.01); *C12N 2795/10171* (2013.01)

(58) Field of Classification Search
None
See application file for complete search history.

(56) References Cited

U.S. PATENT DOCUMENTS

| | | | | |
|---|---|---|---|---|
| 9,358,258 | B2 | 6/2016 | Kim et al. | |
| 9,950,015 | B2 * | 4/2018 | Cimino | A61K 35/35 |
| 9,950,018 | B2 | 4/2018 | Shin et al. | |
| 10,028,984 | B2 * | 7/2018 | Yoon | A23K 20/195 |
| 2014/0017205 | A1 * | 1/2014 | Shin | C12N 7/00 424/93.6 |
| 2014/0356330 | A1 * | 12/2014 | Kim | A61K 35/76 424/93.6 |
| 2015/0322409 | A1 * | 11/2015 | Yoon | C12N 7/00 424/93.6 |
| 2017/0035817 | A1 * | 2/2017 | Shin | A23K 20/195 |
| 2017/0037380 | A1 * | 2/2017 | Shin | A23K 20/10 |
| 2017/0037382 | A1 * | 2/2017 | Shin | A23K 10/18 |
| 2017/0333498 | A1 * | 11/2017 | Yoon | A61K 35/76 |
| 2017/0333499 | A1 * | 11/2017 | Yoon | A23L 2/38 |
| 2017/0340686 | A1 * | 11/2017 | Yoon | A61K 35/76 |
| 2017/0348365 | A1 * | 12/2017 | Yoon | A23L 2/38 |
| 2017/0368116 | A1 * | 12/2017 | Regeimbal | A61K 35/76 |
| 2017/0369852 | A1 * | 12/2017 | Yoon | C12N 7/00 |
| 2018/0000125 | A1 * | 1/2018 | Yoon | A61K 35/76 |
| 2018/0092386 | A1 | 4/2018 | Lu | |
| 2018/0119109 | A1 * | 5/2018 | Yoon | C12N 7/00 |

FOREIGN PATENT DOCUMENTS

| | | |
|---|---|---|
| CN | 201580071133 | 12/2015 |
| CN | 201580071184 | 12/2015 |
| JP | 2004514443 | 5/2004 |
| KR | 20100116289 | 11/2010 |
| KR | 20110041670 | 4/2011 |
| KR | 10-2014-0171676 | 12/2014 |
| KR | 10-2014-0192982 | 12/2014 |

(Continued)

OTHER PUBLICATIONS

Enterohemorrhagic *Escherichia coli* | Johns Hopkins Medicine Health Library, 2018,) (Year: 2018).*
Pacheco et al, Frontiers in Cellular and Infection Microbiology, 2012, vol. 2, article 81, 12 pages (Year: 2012).*
Gohar et al BMC Res. Notes, 2016, 9:80, 18 pages (Year: 2016).*
Mani et al, Vaccine 34 (2016) pp. 2887-2894. available online Mar. 12, 2016 (Year: 2016).*
Walker, Vaccine 33 (2015) 954-965. available online Dec. 5, 2014 (Year: 2014).*
Ho et al, Infection and Immunity, Jul. 2012. vol. 80, No. 7,pp. 2307-2315. published ahead of print Apr. 23, 2012 (Year: 2012).*
Laing et al. PLoS One, May 2012, 7(5): e37362. 12 pages. published May 23, 2012. (Year: 2012).*

(Continued)

*Primary Examiner* — Nita M. Minnifield
(74) *Attorney, Agent, or Firm* — Ballard Spahr LLP

(57) ABSTRACT

The present invention relates to a Myoviridae bacteriophage Esc-CHP-1 that is isolated from the nature and can kill specifically enterohemorrhagic *E. coli* strains, which has a genome represented by the nucleotide sequence of SEQ. ID. NO: 1 (Accession NO: KCTC 12660BP), and a method for preventing and treating the infections of enterohemorrhagic *E. coli* using the composition comprising said bacteriophage as an active ingredient.

2 Claims, 1 Drawing Sheet

Specification includes a Sequence Listing.

(56) References Cited

FOREIGN PATENT DOCUMENTS

| | | | | |
|---|---|---|---|---|
| WO | WO-2013073843 A1 * | 5/2013 | ............. | A61K 35/76 |
| WO | PCT/KR2015/014328 | 12/2015 | | |
| WO | PCT/KR2015/014330 | 12/2015 | | |
| WO | WO-2016108536 A1 * | 7/2016 | ........... | A23K 20/195 |
| WO | WO-2016108538 A1 * | 7/2016 | ............. | A61K 35/76 |
| WO | WO-2016108540 A1 * | 7/2016 | ............... | A23L 2/38 |
| WO | WO-2016108541 A1 * | 7/2016 | ............. | A61K 35/76 |
| WO | WO-2016108542 A1 * | 7/2016 | ............... | A23L 2/38 |
| WO | WO-2016114517 A1 * | 7/2016 | ............. | A61K 35/76 |
| WO | WO-2017111306 A1 * | 6/2017 | ............. | A61Q 19/10 |

OTHER PUBLICATIONS

Branko et al, Institute of Meat Hygiene and Technology, (2011), 52(1), 52-59. Abstract only (Year: 2011).*

Los et al, Postepy Mikrobiologii, (2011) vol. 50, No. 3, pp. 175-190. Abstract only (Year: 2011).*

Los et al, Future Microbiology, (2011), 6/8:909-924 (Year: 211).*

Orth et al, Expert REv. Anti. Ther, 2008, 6/1:101-108. (Year: 2008).*

Allocati et al Int. J. Environ. Res. Public Health 2013, 10, 6235-6254. published: Nov. 25, 2013 (Year: 2013).*

Yang et al, Arch Microbiol (2017) 199:811-825. published online:Jun. 9, 2017 (Year: 2017).*

Rojas-Lopez et al, Frontiers in Microbiology, (Mar. 20, 2018) vol. 9, No. MAR. am. 440. abstract only (Year: 2018).*

Cordonnier et al, Critical Reviews in Microbiology, 2017, 43/1:116-132. published online:Sep. 16, 2016 (Year: 2017).*

Saeedi et al, Microbial Pathogenesis 103 (2017) 186-195. available online: Jan. 3, 2017 (Year: 2017).*

Gerdts et al, ILAR Journal, 2015, 56/1:53-62. (Year: 2015).*

Wenzel et al, Vaccine, 2017, 35:6798-6802, available online:Sep. 7, 2017 (Year: 2017).*

Gohar et al, BMC Research Notes, 2016, 9:80, 18 pages. published online:Feb. 9, 2016 (Year: 2016).*

Viazis, Stelios et al., "Reduction of *Escherichia coli* 0157:H7 Viability on Hard Surfaces by Treatment With a Bacteriophage Mixture", International Journal of Food Microbiology, 2011, 145(1):37-42.

International Search Report and Written opinion dated May 4, 2016 by the International Searching Authority for International Application No. PCT/KR2015/014328, which was filed on Dec. 28, 2015 and published as WO/2016/108538 on Jul. 7, 2016 (Applicant—Intron Biotechnology Inc.) (Original—8 pages// Translated—2 pages).

Clements, A. et al., Infection Strategies of Enteric Pathogenic *Escherichia coli*. Gut Microbes. 2012; 3(2):71-87.

NCBI, GenBank Accession No. EF460875.1. Enterobacteria Phage phiEcoM-GJ1, Complete Genome. 2008 (24 pages).

NCBI, GenBank Accession No. HQ259103.1, *Salmonella phage* SFP10, Complete Genome. 2011 (78 pages).

Tomat, D. et al., Phage Adsorption on Enteropathogenic and Shiga Toxin-Producing *Escherichia coli* Strains: Influence of Physiochemical and Physiological Factors. Food Res Int. 2014; 66:23-8.

Tomat, D. et al., Phage Biocontrol and Enteropathogenic and Shiga Toxin-Producing *Escherichia coli* During Milk Fermentation. Lett Appl Microbiol. 2013; 57(1):3-10.

International Search Report and Written Opinion dated May 4, 2016 by the International Searching Authority for Patent Application No. PCT/KR2015/014330, which was filed on Dec. 28, 2015 and published as WO 2016/108540 on Jul. 7, 2016 (Inventor—Yoon et al.; Applicant—Intron Biotechnology, Inc.) (Original—8 pages; Translation—7 pages).

Non-Final Office Action dated Jun. 1, 2018 by the U.S. Patent and Trademark Office for U.S. Appl. No. 15/538,551, filed Jun. 21, 2017 and published as US 2017/0348365 on Dec. 7, 2017 (Inventor—Yoon et al.; Applicant—Intron Biotechnology, Inc. (12 pages).

U.S. Appl. No. 15/538,551, filed Jun. 21, 2017, Seong Jun Yoon (Intron Biotechnology, Inc.).

* cited by examiner

ENTEROHEMORRHAGIC *E. COLI* BACTERIOPHAGE ESC-CHP-1 AND USE THEREOF FOR INHIBITING PROLIFERATION OF ENTEROHEMORRHAGIC *E. COLI*

CROSS-REFERENCE TO RELATED APPLICATIONS

The present application is a U.S. National Phase Application of International Application No. PCT/KR2015/014328, filed Dec. 28, 2015, which claims priority to Korean Application No. 10-2014-0191676, filed Dec. 29, 2014, each of which are hereby incorporated by reference in their entirety.

REFERENCE TO SEQUENCE LISTING

The Sequence Listing submitted Jun. 21, 2017, as a text file named "08162_0030U1_Sequence_Listing.txt," created on May 24, 2017, and having a size of 199,928 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills enterohemorrhagic *E. coli*, and a method for preventing and treating the infections of enterohemorrhagic *E. coli* using a composition comprising the bacteriophage as an active ingredient. More particularly, the present invention relates to a Myoviridae bacteriophage Esc-CHP-1 that is isolated from the nature and can kill specifically enterohemorrhagic *E. coli* strains, which has a genome represented by the nucleotide sequence of SEQ. ID. NO: 1 (Accession NO: KCTC 12660BP), and a method for preventing the infections of enterohemorrhagic *E. coli* and thereafter treating them using the composition comprising said bacteriophage as an active ingredient.

2. Description of the Related Art

*Escherichia coli* (*E. coli*) is a Gram-negative *bacillus* and has a cell wall comprising somatic antigen (O), flagella antigen (H) and capsular antigen (K) composed of lipopolysaccharides. The combination of these antigens contributes to various serotypes. In general, *E. coli* is divided to non-pathogenic *E. coli*, residential flora in bowels and pathogenic *E. coli* acquiring disease-causing factors such as enterohemorrhagic *E. coli* (EHEC).

When being infected, the enterohemorrhagic *E. coli* produces Shigatoxin or verotoxin, a similar kind in human and livestock so as to provoke diseases. A variety of serotypes (026, 0103, 0104, 0111, 0146 and 0157 etc.) have been reported. Above all, *E. coli* O157:H7 was first identified in 1982 because it could cause food poisoning from hamburgers in United States. Afterward, it is recognized as a major pathogen of food poisoning world-widely.

The infections of enterohemorrhagic *E. coli* occurs in human by eating contaminated food (hamburgers, milk and vegetables etc.). It is elucidated that enterohemorrhagic *E. coli* is transmitted between persons under a bad sanitation and causes even water-mediated infections. In healthy adults, the infections of enterohemorrhagic *E. coli* manifest symptoms of diarrhea, dehydration and anemia, and are mostly recovered soon. However, 5 year or less-old children and old people are vulnerable and likely to evoke hemolytic uremic syndrome leading to death.

Moreover, the enterohemorrhagic *E. coli* causes animal diseases in livestock including cow, horse, goat, pig and chicken and the like. Especially in calves or piglets, it manifests lesions of bleeding in gastric mucosa and small intestine and even leads to high mortality. Nowadays, the cases infected by enterohemorrhagic *E. coli* are increasing rapidly. Considering a significant damage in livestock industry by such *E. coli*, it is urgently requested to develop a method for preventing or treating the infections of enterohemorrhagic *E. coli*. A variety of antibiotics have been used to prevent or treat such enterohemorrhagic *E. coli* infections. However, according to the recent rise of antibiotic-resistant bacteria, an efficient alternative is urgently requested.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella disentriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasily achieved.

Therefore, the present inventors tried to develop a composition applicable for the prevention or treatment of enterohemorrhagic *E. coli* infections by using a bacteriophage that is isolated from the nature and can kill enterohemorrhagic *E. coli* selectively, and further to establish a method for preventing or treating the infections of enterohemorrhagic *E. coli* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used for the prevention and treatment of enterohemorrhagic *E. coli* infections, leading to the completion of the present invention.

SUMMARY OF THE INVENTION

It is an object of the present invention to provide a Myoviridae bacteriophage Esc-CHP-1 that is isolated from the nature and can kill enterohemorrhagic *E. coli* specifically, which has the genome represented by the nucleotide sequence of SEQ. ID. NO: 1 (Accession NO: KCTC 12660BP).

It is another object of the present invention to provide a composition applicable for the prevention of enterohemorrhagic *E. coli* infections, which comprises the bacteriophage Esc-CHP-1 that can infect and kill enterohemorrhagic *E. coli*, as an active ingredient and a method for preventing the infections of enterohemorrhagic *E. coli* using said composition.

It is another object of the present invention to provide a composition applicable for the treatment of enterohemorrhagic *E. coli* infections, which comprises the bacteriophage Esc-CHP-1 that can infect and kill enterohemorrhagic *E. coli*, as an active ingredient and a method for treating the infections of enterohemorrhagic *E. coli* using said composition.

It is another object of the present invention to provide a disinfectant for preventing and treating the infections of enterohemorrhagic *E. coli* using said composition.

It is another object of the present invention to provide a drinking water additive for preventing and treating the infections of enterohemorrhagic *E. coli* using said composition.

It is also an object of the present invention to provide a feed additive effective upon farming by preventing and treating the infections of enterohemorrhagic *E. coli* using said composition.

To achieve the above objects, the present invention provides a Myoviridae bacteriophage ESC-CHP-1 that is isolated from the nature and can kill specifically enterohemorrhagic *E. coli*, which has the genome represented by the nucleotide sequence of SEQ. ID. NO: 1 (Accession NO: KCTC 12660BP), and a method for preventing and treating the infections of enterohemorrhagic *E. coli* using a composition comprising the bacteriophage as an active ingredient. The bacteriophage Esc-CHP-1 has been isolated by the present inventors and then deposited at Korean Collection for Type Cultures, Korea Research Institute of Bioscience and Biotechnology in Aug. 21, 2014 (Accession NO: KCTC 12660BP). The present invention also provides a disinfectant, a drinking water additive, and a feed additive applicable for the prevention or treatment of enterohemorrhagic *E. coli* infections, which comprises the bacteriophage Esc-CHP-1 as an active ingredient.

Since the bacteriophage Esc-CHP-1 included in the composition of the present invention kills enterohemorrhagic *E. coli* efficiently, it is regarded as effective to prevent or treat *E. coli* diarrhea (infections) caused by enterohemorrhagic *E. coli. Therefore, the composition of the present invention can be utilized for the prevention and treatment of E. coli* diarrhea caused by enterohemorrhagic *E. coli*. In this specification, the *E. coli* diarrhea includes symptoms caused by the *E. coli* infections accompanying fever, diarrhea and the like.

In this description, the term "treatment" or "treat" indicates (i) to suppress the diarrhea caused by enterohemorrhagic *E. coli*; and (ii) to relieve the diarrhea caused by enterohemorrhagic *E. coli*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Esc-CHP-1 is included as an active ingredient. At this time, the bacteriophage Esc-CHP-1 is included at the concentration of $1\times10^{1}$ pfu/ml~$1\times10^{30}$ pfu/ml or $1\times10^{1}$ pfu/g~$1\times10^{30}$ pfu/g, and preferably at the concentration of $1\times10^{4}$ pfu/ml~$1\times10^{15}$ pfu/ml or $1\times10^{4}$ pfu/g~$1\times10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as a disinfectant, a drinking water additive, or a feed additive according to the purpose of use, but not always limited thereto.

Advantageous Effect

The method for preventing and treating the infections of enterohemorrhagic *E. coli* using this composition comprising the bacteriophage Esc-CHP-1 as an active ingredient, have the advantage of high specificity to enterohemorrhagic *E. coli*, compared with the conventional methods based on the chemical materials including the conventional antibiotics. That means, the composition of the present invention can be used for preventing or treating the infections of enterohemorrhagic *E. coli* specifically without affecting other useful residential bacteria, and accordingly has fewer side effects. In general, when chemical materials such as antibiotics are used, the general residential bacteria are also damaged to weaken immunity in animals with carrying various side effects. In the meantime, the composition of the present invention uses the bacteriophage isolated from the nature as an active ingredient, so that it is very nature-friendly.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
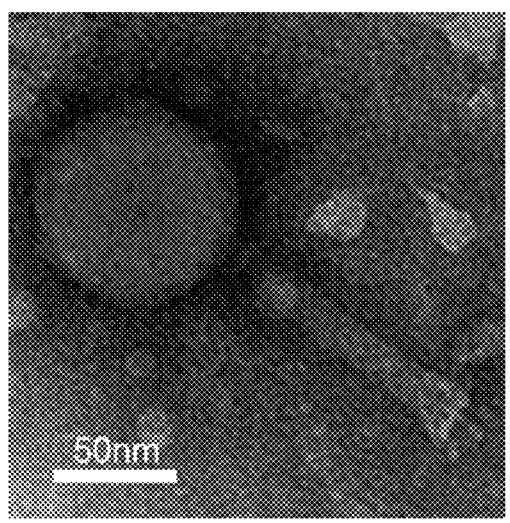
FIG. 1 is an electron micrograph showing the morphology of the bacteriophage Esc-CHP-1.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing Enterohemorrhagic *E. coli*

Samples were collected from the nature to screen the bacteriophage having the capability to kill enterohemorrhagic *E. coli*. The enterohemorrhagic *E. coli* used for the bacteriophage isolation herein were the one that had been isolated by the present inventors and identified as enterohemorrhagic *E. coli* previously.

The isolation procedure of the bacteriophage is described in detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with enterohemorrhagic *E. coli* at the ratio of 1/1000, followed by shaking culture at 37° C. for 3~4 hours. Upon completion of the culture, centrifugation was performed at 8,000 rpm for 20 minutes and supernatant was recovered. The recovered supernatant was inoculated with enterohemorrhagic *E. coli* at the ratio of 1/1000, followed by shaking culture at 37° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for 20 minutes and the resulting supernatant was recovered. The recovered supernatant was filtrated by using a 0.45 μm filter. The obtained filtrate was used in spot assay for examining whether or not the bacteriophage capable of killing enterohemorrhagic *E. coli* was included therein.

Spot assay was performed as follows; TSB medium was inoculated with enterohemorrhagic *E. coli* at the ratio of 1/1000, followed by shaking culture at 37° C. for overnight. 3 ml (1.5 of $OD_{600}$) of the culture broth of enterohemorrhagic *E. coli* prepared above was spread on the TSA (Tryptic Soy Agar; pancreatic digest of casein, 17 g/L; papaic digest of soybean, 3 g/L; sodium chloride, 5 g/L; agar, 15 g/L) plate. The plate stood in a clean bench for about 30 minutes to dry. After drying, 10 μl of the resulting filtrate was spotted directly onto the surface of the enterohemorrhagic *E. coli* lawns and dried for about 30 minutes. Following drying, the plate was incubated at 37° C. for a day and then, examined for the formation of clear zones on the surface of the bacterial lawns. If a clear zone was generated where the filtrate was dropped, it is judged that the bacteriophage capable of killing enterohemorrhagic *E. coli* was included in the filtrate. Through the above procedure, the filtrate containing the bacteriophage having the killing ability of enterohemorrhagic *E. coli* could be obtained.

After that, the bacteriophage was isolated from the filtrate confirmed above to have the bacteriophage capable of killing enterohemorrhagic *E. coli*. The conventional plaque assay was used for the isolation of pure bacteriophages. In detail, a plaque formed in the course of the plaque assay was picked up by using a sterilized tip, which was then added to the culture solution of enterohemorrhagic *E. coli*, followed by culturing at 37° C. for 4~5 hours. Upon completion of the culture, centrifugation was performed at 8,000 rpm for 20 minutes to obtain supernatant. The recovered supernatant was inoculated with enterohemorrhagic *E. coli* culture at the ratio of 1/50, followed by culturing at 37° C. for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plague formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Myoviridae.

The solution containing the pure bacteriophage confirmed above proceeded to purification. The culture broth of enterohemorrhagic *E. coli* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Esc-CHP-1 and then deposited at Korean Collection for Type Cultures, Korea Research Institute of Bioscience and Biotechnology in Aug. 21, 2014 (Accession NO: KCTC 12660BP).

Example 2: Separation and Sequence Analysis of the Bacteriophage Esc-CHP-1 Genome The genome of the bacteriophage Esc-CHP-1 was separated as follows. The genome was separated from the bacteriophage suspension obtained in Example 1. First, in order to eliminate DNA and RNA of enterohemorrhagic *E. coli* included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/10) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Esc-CHP-1 genome.

The nucleotide sequence of the genome of the bacteriophage Esc-CHP-1 obtained above was analyzed by Next Generation Sequencing (NGS) using illumina Mi-Seq device at National Instrumentation Center for Environmental Management, Seoul National University. As a result, it is suggested that the final genome of bacteriophage Esc-CHP-1 has 157,392 bp of size and the nucleotide sequence of the whole genome has SEQ. ID. NO: 1.

Similarity of the genomic sequence of the bacteriophage Esc-CHP-1 obtained above with the previously reported bacteriophage genome sequences was investigated by using BLAST. From the BLAST result, the genomic sequence of the bacteriophage Esc-CHP-1 was confirmed to have relatively high homologies with the sequences of *E. coli* bacteriophage PhaxI (Genbank Accession NO: JN673056.1), *Salmonella* bacteriophage SFP10 (Genbank Accession NO: HQ259103.1), *E. coli* bacteriophage vB_EcoM_CBA120 (Genbank Accession NO: JN593240.1), *Salmonella* bacteriophage vB_SalM_SJ3 (Genbank Accession NO: KJ174318.1) and *Salmonella* bacteriophage PhiSH19 (Genbank Accession NO: JN126049.1) (99%, 98%, 98%, 97% and 97% of identity, respectively). Nevertheless, the genomic structure was different from one another. The bacteriophage Esc-CHP-1 had a linear genome, but *Salmonella* bacteriophage SPF10, *Salmonella* bacteriophage PhiSH19 and *E. coli* bacteriophage PhaxI had circular genomes. The numbers of ORFs (Open Reading Frame) within their genomes were also discriminated. The genome of bacteriophage Esc-CHP-1 was determined to comprise 209 of ORFs, while that of *Salmonella* bacteriophage SPF10 comprised 201 ORFs; *E. coli* bacteriophage vB_EcoM-CBA120, 260 ORFs; *Salmonella* bacteriophage vB-SalM_5J3, 214 ORFs; and *E. coli* bacteriophage PhiSH19, 166 ORFs. Even if the *E. coli* bacteriophage PhaxI had the same number of ORFs with the bacteriophage Esc-CHP-1 within the genome, their genomic structures were different each other as described above and their genomic locations of ORFs within the genomes were remarkably distinct.

Based upon this result, it is concluded that the bacteriophage Esc-CHP-1 should be a novel bacteriophage not reported previously.

Example 3: Investigation of Killing Ability of the Bacteriophage Esc-CHP-1 Against Enterohemorrhagic *E. coli*

Figure 2:
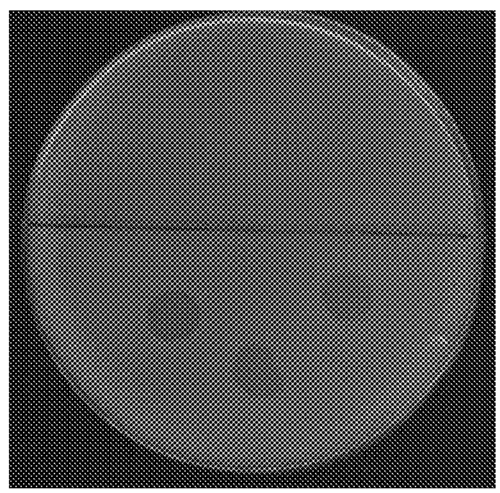
FIG. 2 is a photograph illustrating the capability of the bacteriophage Esc-CHP-1 to kill enterohemorrhagic *E. coli*. The clear zone on the dish is the formation of plaque by lysis of bacteria cells.

The killing ability of the isolated bacteriophage Esc-CHP-1 against enterohemorrhagic *E. coli* was investigated. To do so, the formation of clear zone was observed by the spot assay by the same manner as described in Example 1. The enterohemorrhagic *E. coli* used for this investigation were total 10 strains which had been isolated and identified as enterohemorrhagic *E. coli* previously by the present inventors. The bacteriophage Esc-CHP-1 demonstrated the killing ability against 9 strains of the enterohemorrhagic *E. coli* used in this experiment. The representative result of the killing ability test is shown in FIG. 2. In the meantime, the activity of the bacteriophage Esc-CHP-1 to kill *Staphylococcus aureus, Enterococcus faecalis, Enterococcus faecium, Lactobacillus plantarum, Streptococcus uberis* and *Pseudomonas aeruginosa* was also investigated. As a result, it is decided that the bacteriophage Esc-CHP-1 did not have the killing activity against these microorganisms.

Therefore, it was confirmed that the bacteriophage Esc-CHP-1 has the specific ability to kill enterohemorrhagic *E. coli* and a broad antibacterial spectrum against enterohemorrhagic *E. coli*, suggesting that the bacteriophage Esc-CHP-1 of the present invention could be used as an active ingredient of the composition for preventing and treating the infections of enterohemorrhagic *E. coli.*

Example 4: Preventive Effect of Bacteriophage Esc-CHP-1 on the Infections of Enterohemorrhagic *E. coli*

100 μl of the bacteriophage Esc-CHP-1 solution at $1\times10^9$ pfu/ml was added to a tube containing 9 ml of TSB. To another tube containing 9 ml of TSB, only the same volume of TSB was added. Then, the enterohemorrhagic *E. coli* culture was added to each tube to prepare bacterial suspension in 0.5 of $OD_{600}$. After that, the tubes were transferred to an incubator at 37° C., followed by shaking culture, during which the growth of enterohemorrhagic *E. coli* was observed. As presented in Table 1, the growth of enterohemorrhagic *E. coli* was inhibited in the tube added with the bacteriophage Esc-CHP-1 solution, while the growth of enterohemorrhagic *E. coli* was not inhibited in the tube without the bacteriophage Esc-CHP-1 solution.

TABLE 1

Inhibition of growth of enterohemorrhagic *E. coli*

| | $OD_{600}$ | | |
|---|---|---|---|
| Item | Culturing 0 min. | Culturing 60 min. | Culturing 120 min. |
| (−) bacteriophage solution | 0.5 | 1.2 | 1.8 |
| (+) bacteriophage solution | 0.5 | 0.3 | 0.2 |

The above results indicate that the bacteriophage Esc-CHP-1 not only inhibited the growth of enterohemorrhagic *E. coli* but also could kill them. Therefore, the bacteriophage Esc-CHP-1 can be used as an active ingredient of the composition for preventing the infections of enterohemorrhagic *E. coli.*

Example 5: Therapeutic Effect of Bacteriophage Esc-CHP-1 on the Infections of Enterohemorrhagic *E. coli*

Therapeutic effect of the bacteriophage Esc-CHP-1 on animals affected by enterohemorrhagic *E. coli* was investigated. 4 weaning pigs at 25 days of age were grouped together; total 2 groups of pigs were raised in a pig pen (1.1 m×1.0 m) for 14 days. Heating system was furnished and the surrounding environment was controlled. The temperature and the humidity of the pig pen were controlled and the floor was cleaned every day. On the $7^{th}$ day of the experiment, all the animals were orally administered with 1 mL of enterohemorrhagic *E. coli* suspension using an oral injection tube. The enterohemorrhagic *E. coli* suspension administered above was prepared as follows: enterohemorrhagic *E. coli* was cultured in TSB medium at 37° C. for 18 hours and the bacterial cells were collected by centrifugation. Saline (pH 7.2) was added to the bacterial cell pellet to make cell suspension at a concentration of $10^9$ CFU/ml. From the next day of the enterohemorrhagic *E. coli* challenge, the experimental group (bacteriophage solution treated pigs) were orally administered with the bacteriophage Esc-CHP-1 ($10^9$ PFU/head) via the same way as used for the above administration twice a day. The control group (bacteriophage solution non-treated pigs) was treated with nothing. Feeds and drinking water were equally provided to both groups. After the challenge of E enterohemorrhagic *E. coli*, all the animals were observed every day whether or not they experienced diarrhea. The observation was performed by measuring the diarrhea index. The diarrhea index was set as follows according to Fecal Consistency (FC) score (normal: 0, loose stool: 1, moderate diarrhea: 2, and severe diarrhea: 3). The results are shown in Table 2.

TABLE 2

| Fecal Consistency score | | | | | | | | |
|---|---|---|---|---|---|---|---|---|
| Days after entero-hemorrhagic *E. coli* challenge | 0 | 1 | 2 | 3 | 4 | 5 | 6 | 7 |
| Control group (−bacteriophage solution) | 2.25 | 2.5 | 2.5 | 2. | 2 | 1.5 | 1.5 | 1.5 |
| Experimental group (+bacteriophage solution) | 2.25 | 2 | 1 | 0.5 | 0.25 | 0 | 0 | 0 |

From the above results, it is confirmed that the bacteriophage Esc-CHP-1 of the present invention could be very effective to treat the infections of enterohemorrhagic *E. coli*.

Example 6: Preparation of Feed Additives and Feeds

Feed additive containing bacteriophage Esc-CHP-1 at a concentration of $1\times10^8$ pfu/g was prepared using the bacteriophage Esc-CHP-1 solution. The preparation method thereof was as follows: Maltodextrin (40%, w/v) was added to the bacteriophage solution and then, trehalose was added to reach 10% of final concentration. After mixing well, the mixture was freeze-dried. Lastly, the dried mixture was grinded into fine powders. The drying process above can be replaced with vacuum-drying, drying at warm temperature, or drying at room temperature. To prepare the control feed additive for comparison, feed additive that did not contain the bacteriophage but contained buffer (10 mM Tris-HCl, 10 mM $MgSO_4$, 0.1% Gelatin, pH 8.0) only was prepared.

The above two kinds of feed additives were mixed with the 1,000 times volume of feeds for pig farming respectively, resulting in two kinds of final feeds.

Example 7: Preparation of Drinking Water Additives and Disinfectants

Drinking water additive and disinfectant are different in intended use but same in the composition, so they have been prepared by the same manner. Drinking water additive (or disinfectant) containing bacteriophage Esc-CHP-1 at a concentration of $1\times10^8$ pfu/ml was prepared using the bacteriophage Esc-CHP-1 solution. Particularly, to prepare drinking water additive (or disinfectant), the bacteriophage ESC-CHP-solution was added to buffer solution to reach $1\times10^8$/ml, which was mixed well. For the comparison, the above buffer solution itself was used as the drinking water additive (or disinfectant) that did not contain the bacteriophage.

The prepared two kinds of drinking water additives (or disinfectants) were diluted in water at the ratio of 1:1000, and then used as drinking water or disinfectant.

Example 8: Effect on Pig Farming

The effect of the feeds, drinking water, and disinfectant prepared in Example 6 and Example 7 on pig farming was investigated. Particularly, the investigation was focused on diarrhea conditions by fecal consistency score used in Example 5. Total 30 piglets were grouped into three groups, and each group was composed of 10 piglets (group A: feed test group, group B: drinking water test group; and group C: disinfectant test group). The experiment was continued for 2 weeks. Each group was divided by two sub-groups comprising 5 piglets each. The sub-groups were divided according to the treatment of the bacteriophage Esc-CHP-1 or not (sub-group-①: treated with the bacteriophage Esc-CHP-1; and sub-group-②: not-treated with the bacteriophage). The piglets used in this experiment were weaning pigs at 20 days of age and raised in a separated room placed at a sufficient distance from each other. Each sub-group was divided and named as shown in Table 3.

TABLE 3

| Sub-groups of pig farming experiment | | |
|---|---|---|
| | Sub-group | |
| Item | Treated with the bacteriophage Esc-CHP-1 | Not-treated with the bacteriophage |
| Fed with feeds | A-① | A-② |
| Provided with drinking water | B-① | B-② |
| Treated with disinfectant | C-① | C-② |

Feeds were provided according to the conventional feed supply method as presented in Table 3 with the feeds prepared in Example 6. Drinking water was provided according to the conventional water supply method as presented in Table 3 with the drinking water prepared in Example 7. Disinfectant was treated three times a week with taking turns with the conventional disinfectant. That is, on the day when the disinfectant of the present invention was sprayed, the conventional disinfectant was not treated. The results are shown in Table 4.

TABLE 4

| Fecal consistency score of pig farming experiment | | | | | | | | | | | | | | |
|---|---|---|---|---|---|---|---|---|---|---|---|---|---|---|
| Group | Fecal consistency score | | | | | | | | | | | | | |
| 그룹 | d1 | d2 | d3 | d4 | d5 | d6 | d7 | d8 | d9 | d10 | d11 | d12 | d13 | d14 |
| A-① | 0 | 0.2 | 0 | 0 | 0.2 | 0 | 0 | 0 | 0.2 | 0 | 0 | 0 | 0 | 0 |
| A-② | 0 | 0 | 0.4 | 0.2 | 0.4 | 0.2 | 0.4 | 0.2 | 0.2 | 0.2 | 0.4 | 0.2 | 0.2 | 0.2 |
| B-① | 0.2 | 0 | 0 | 0 | 0 | 0 | 0.2 | 0 | 0 | 0 | 0 | 0.2 | 0 | 0 |
| B-② | 0.2 | 0 | 0.4 | 0.2 | 0.2 | 0.4 | 0.2 | 0.4 | 0.2 | 0.2 | 0.4 | 0.2 | 0.2 | 0.2 |
| C-① | 0 | 0 | 0.2 | 0 | 0 | 0 | 0 | 0.2 | 0 | 0 | 0 | 0 | 0 | 0 |
| C-② | 0 | 0 | 0.2 | 0.2 | 0.4 | 0.4 | 0.4 | 0.2 | 0.2 | 0.4 | 0.2 | 0.2 | 0.4 | 0.4 |

From the above results, it is confirmed that the feeds, drinking water, and the disinfectant prepared according to the present invention were effective in reducing the animal diarrhea. Therefore, it is concluded that the composition of the present invention could be efficiently applied for the improvement of productivity of animal farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for preventing or treating infections of enterohemorrhagic *E. coli* in a subject, the method comprising a step of administering to the subject a composition comprising Myoviridae bacteriophage Esc-CHP-1 (Accession NO: KCTC 12660BP) that is isolated from nature and can kill enterohemorrhagic *E. coli* specifically, which has the genome represented by the nucleotide sequence of SEQ ID NO: 1, as an active ingredient.

2. The method according to claim 1, wherein said composition is administered to the subject in the form of a feed additive, a drinking water additive, or a disinfectant.

* * * * *

SEQUENCE LISTING

<160> NUMBER OF SEQ ID NOS: 1

<210> SEQ ID NO 1
<211> LENGTH: 157392
<212> TYPE: DNA
<213> ORGANISM: Bacteriophage Esc-CHP-1

<400> SEQUENCE: 1

```
ggaacttgca tgccaccgtt gattgtgact acgccagtga caggatagaa cggcaaggaa     60

aggaaagttt ctccaccaac atttgattta tacgtgaaag gaatctggtg aggagctgtg    120

attacgccgc cgaataattc ttctacattt ctggtcattt gaaaataccc cataaaggat    180

ttgccaatat ggggtattta gtctgaacta ataaaattta tgaacaaagg tataataaga    240

accccgccga agaggggtta tttaaatttt aacagcaaca acatcatttt ataatgttgg    300

tgatgtcacg ataaagcgtc cagtccaaca ccaactacag tccaataacc gtaattagca    360

tcatatctta gtgataaccc cttatgtcta cctgctggtg gaggagtaaa attgccaact    420

ctaatatctg atgcccagtt aatgactaat gaatctgttc ctgatgcatt gtgaattgtc    480

aaatctattc ttgctccatc taattttttg gtggcagaaa ctatattaat aggtgttcct    540

gttgcggtgc atacaacata ggatgcttta tatgggtcta acgttactgt ctcacctccc    600

gctataggct gattgcttct tgtgttaaca gggtttgtgc ttacgttaac ttgagcattg    660

ttaagattcc ataatctttc ataagtgttt cttatccctt catcattaac aacaggaaac    720

tcagctaaaa gtgttacatc ctgtacgtgg ttgtcatggc tatctggtct gaagtcgaaa    780

tcgctaacag tacctccaga gaaatagtta cgaaaacctc tgacctgaac tgatggagat    840

gaataacctg atttgagtcc tatgaactcg ttcatgtgtg aaaacttgtt aatcacaata    900

tcagttagcg tgttcacctc aaggtcaata ccaagaaatg tattacccag tgcagtgtaa    960

gtattatctg taggatgccc caatgaaatg cctgcgccaa ggtttccctc gattgttccg   1020

tttataacca ttgagttcat caggcttagt cctacaaacc catcacccgc agtgtgctct   1080

acacatgggt taataaagat atcgcatgat gtaccacgtg gatttgacgg attgttatct   1140

ttatctacta aaataccgtg caggggtttt gttgtgaaaa cctccacgtt attagagcaa   1200

ataaaatcag tgtatgtaca gcattgagtc caagccagat ataacccagc agttgttata   1260
```

```
ttggttgctt gaataccagg aaaaccacca gatattacgc cacgaagtga tagcccgtac   1320
ttagcatgac caagaccatc aagaataacc ctgccaccac caaagaaagg tttatacccc   1380
caataccccct catcttgtcc acgtaaatct atttccacaa catggtcatg tgcaccagat   1440
gtaagtttta ttcgcactcc tacatcaaac catatttgaa caggttttgt gaatctcagt   1500
ggttcagatg tttcatatac tcctgaaggt actgttatta caacacctgc ttcagcatca   1560
gctttcatag cagcgaatgc tgatgcatta tcaaaaccag gaataggctt agccaaatac   1620
tcaaaaacag aaaccctttc actattttta atttgttggc ttatagcaac cgagtttgat   1680
acttgtgact tatatgtcaa aagattcgca cctttaccaa gtgtgccact agccaaatcc   1740
gctctcaatg atacatcacc aacactcaac catgcaccta aaccaacacc gcctgagtta   1800
tcgggtgtag aaccagcggc aactaccttt ggcaaagaac catcccatcg atattttta   1860
tcatcgtgaa caagaagttc atttttcaca ttaatggtat gaccgaaatt aaaagaacca   1920
ggtaaagtca catattcttc gcggcttact gctaattccc caaggtcaac agagccagaa   1980
gaatgagtaa ggatggcttg ttcgttcaga cttatcgcaa tcgttcctga aacaataccc   2040
gaaggaagag aataagcccg ttgggtagac tcatcataaa ttactttaaa tccgctgaga   2100
tcaataccga cagtgaaata aatgacttcg tcttctttga caccgaaatt tcgagcaata   2160
gattgtttgt taacttctat ggaagtggag ccgcgtggtt gattgaattg agaaatcatg   2220
ttaatacccc ataaaggatg accaatatgg ggtatttagt ctgaactaat aaatttatga   2280
acaaaggtat aacaagaacc ccgccaaagc ggggtttgac aatcctattc caaacacatt   2340
tcaaaatata ccaacatcat cccacccatc ataaacagac gaccccgata atcttgatcc   2400
atctatgttg gcgaaataaa aatacgctga cccatcattg atatcaccta taaagttctt   2460
atacccgttt gatgacaacc tgagagagcc aacagcatta tcaattaggg taatgcaaac   2520
agtaaactct atataataaa aatcccccaa aattgggggga tttttatttt tactaccagt   2580
aataccaatc accttttttta cttctgacta gaatagaaca atcggtaaca gctactgtag   2640
ataccccacc aatccttatc tcatacagtt tactaggcaa tcttttctta gttagagaga   2700
ctttaaaatc tgtaccagtt acagtgatat attccgtccc atcctcacta gctatctgta   2760
aatctaggcc gctgggactt gctgggagct taacataaag ctgttgttct gctgtactac   2820
cagcaaaatg accgataact gtagatgtcc actcacttaa agtcaaccct gaacgcacaa   2880
agtccacatt gagcggttcc ttgataagtg cagcaggtgc attgtaatta tgcccgttaa   2940
gtacatagta gttgctacta ccaatctcta ctgtgtctgc tgtgcaataa gagtggaagg   3000
tttttgagtt atcaaaacga tacagacttc tgattaacac acgctcttgt atgcttcttg   3060
ttaagatacc acaacctgcg gagaggtgga gtgtggagat ggtaagcgta tgactttcac   3120
tgttggcctt ggatgacaac aatgacacct taggttcacc ctcttgagta aagtctttac   3180
tattaccctc acaatacatg accccaatgt cccacgcagc agggtccatt gttaccaccc   3240
cagcacctgc cgtattctca gagcaaatca caccaacact agtagataaa ccacgaccta   3300
agataatacc agcacctatc gtatatttac tcgcatcatc tgtgattggg tcataaccaa   3360
gccccataga cttatccgta ccccatgcac taatgtgagg gaagtgtgtt gcgttcacat   3420
aggtatcacc ttgctcacct tctgttgaat aacctaatgc cataccccctt gcacagttgt   3480
ttgcatggag agtacccatt tgaaaatacc agcaagcaaa tattacaata ccatacctat   3540
tagcattata tacatagatg ctacccatct cagattctgc acacagaaga cgtgcataaa   3600
```

```
aaccatatga tgcaatatct gcacagtcta cgtttaagct accgattaag cgtaatcctc   3660
gcacttggtt ctctgtatta gccacatcca ctgttgctgt accaacagga aatttactaa   3720
cacgtacaac agcttttaac gtaggccata cggagccaat tgctttaatt gttgccccgt   3780
ttagattccc acgtaagtaa gaaggtataa caacctcatc cgttacgtgg taggtagaat   3840
tcccattcag atttaatgta cctgtggcta tagctagttt tatagcaggt aaacagtcaa   3900
aactagggtc attggggatt gcaccaaaat tctcaggtga gtgttcatta aaccctgtta   3960
acttaccaac gttagtccag gaagagtccg gagcagcgcc ataactaaca ggtaatgtcc   4020
cattgtactt gtaccagaac ccatctgaat gtagaacaac ctgatattta tcagatacat   4080
tcccaccatc accgaataca ccggtctttt tgtaaagaga cagactaccg gaatcaataa   4140
gagaagaacc tttccaggag gctaaacgtt gctctaatcc aacaacacca actacaagcc   4200
atgcccctgg accaacacct cctgtatcca atggggtaga ttctggaggg actactttgg   4260
gtacagaacc atcccaacga tatttaatat cgttactcac aaccaactca ttcttggtat   4320
taacagttac acctgtatcg aatgaaccag gtaaggtcac atactcctca cgagatacgg   4380
ctaatgcgcc cagatcaaca ctaccagcag aatgcacaag tacagccgaa gaactaaggc   4440
tgactgccgt ggttccagtc ggtagctctg gaataaaata tgatctctgt gttactttat   4500
catagataac tttatacccg cttaacacag caccaacact aaaataaatg acctctgtat   4560
ctttaacatt ggttacacga gccacttccc gcaaagtata atcaatttga ttatagatgt   4620
ttggcgttcc attgataatt acaacaactt catcctctgc atccagttct tgcgcaagag   4680
tgattttact ggttaatgga tcgaatgtga accccagatt tttatactgg cgacttccgt   4740
ttatatcaat ggccggaaca tcatcaacaa cgatgtctaa cgtgatttcg gtttcaccgc   4800
caatcgctga acccccatta tagacccaag taatcgtaga agaaccagaa ctaccgccat   4860
tacccaattg aataggagta tattcaatca cctgaagttc tgtgttggct ggcaaagaag   4920
gactgaaagt gattacattc ccatctagtg aatatttgga ttccgcaaga cgttttccgt   4980
cagcatacac gtccacgatt gttggtggag tattgagagt gacagcactt gtttcagacg   5040
ccaaaatttg tgtaaagatt tcacgactgt agacacggcc ttgaccaaga ccgacgccgg   5100
atgtgataac ccaaccttgt tcaggtccag accaagtaaa cgttgctgat acgttatcag   5160
ttgttatagc catgtcttca gtggagccat acaaattatt tccagaagga gacacggtca   5220
atgggtaagt ggcaaatttc ccataagcat cacaaatagt aacggaatcc ccaatacgcg   5280
taggggaagg gagaaccact gtagatgtcc ctgtggtatt attaatgaga tagccacgac   5340
cttctaacaa attgctagag ggagcgtgag ggagcgtttc ccagcgtatt ccaccgcccc   5400
ccaaagacaa ccaaccaccg ttttcgtaat aaccttcaaa ttcatcacta tcaggattgt   5460
aacgcacaga agatggaaga cctgtaactt cagtatcttc aggaaatgtc attacggcac   5520
caggggaatg ctcaatagtg ccggagttgt tgaagccttt tatgttcgaa gactcagaag   5580
tttctaaacc caaagggaaa agaggctgtg ttggtttgtt ggccatttgt aatacccccta  5640
aatgtattca tgtcatctag gggtatttag ttttagaaag aagctgcaat agaataatca   5700
acagaacaag cagttgttgt attcgcatta acaacggaaa ttctcaattt accgcccacc   5760
acagaccctg tgaacgtcac tgtaccactc gtacttttct gaactaacaa ctctgatttg   5820
atcgttccgt cacgagttat ggttactcga tatgtgtcaa caacgttacc tatcccccat   5880
tgcgcagtta ccagtatttg acaaaggttc accaaatcaa aatctggaag agtcgtcgtt   5940
ccagaagccg aaaccgtgta tgacgacaaa ttcgttttgg tacgataaac ggcgttcccc   6000
```

```
aaactattgt cgatagaggt catcttggca ttatacgttg atacactaac tttatcactg   6060
gaaagagaac tgatgctgtt atccagagat gccatcttcg tgttgtacgt gctgacctcg   6120
actttattac ccagagacgt attgatattg gagatactca aatccaatga cgccatctta   6180
gtgttgtaag tcgaggtgtt gactttcccg ttcaacgacg tgttgatgtt attaatctgg   6240
gattctagac tcagcatatc tgcgtcatac gctgtcgttg tcacatatcc attaaatcgg   6300
ttgtctgcaa acaacgcatc aaaaaatgca gtcattgtcc aataacgcgc tccagaatct   6360
gtttgtactg gaactgaagt cggcaacgtt ggtccggtat acgcagacaa cctggtgaag   6420
tccaaattga atttgtaata tccggatgtc aacaactccc cagccaaacc agaaccaggc   6480
ggggtagtgt cttcactgac gccatgcttt ctcaacatgc tcaggttaac accatctgtc   6540
gagttcgttg gttcatctgt gattgaaacg gattttccgg cgggaacttg tatgccccca   6600
ttggtcacca acaacgcatt gaaagtcttt ttgccattga ttgtttgttc accactatct   6660
gtacgaataa ctttgttggc cagagtatca ttgattgtgt caacagatct tttcaactca   6720
tatgtcaggc gagcagatgg tggaaacaat gggtcgttaa cttcaaaatc gttaataacg   6780
tcatttttac ttactttgtc gtcaacagaa cccaatatct gatctatctg ctgacctgta   6840
tattgactca ggaaatcggc catttttagc tccttgaact ttctaggaat acagtaaacc   6900
cagcaggatg gaaatgctga cggaagacac gttcaaatac gccttcgaaa tcagatacgt   6960
cgcctgggac tcttatcacg taagtgtact catcataaata atagtcatca cgcatccctg  7020
tcataccgtc acattcaaaa ttgccatcca gaccgcctat ttcctctttt gggaaataga   7080
cactgactgg acaaccaaaa tatatccaaa agaacaattc aattgctttc ttggttccgc   7140
ggattttata gatatgtttt aacagtttca accaacgtgg atgatctagc gttctccgtt   7200
tcgttccttc gatataaaca gagaacgtat cgcccgtggc cgtcaataaa gaatccgaac   7260
cgactgggat aaaatgtcca aattcttgaa atgatttatc aacagttcgt tggaaaccaa   7320
aatcattata ccagtcatct atctgtttgt tcttatcttc tattgacaat agcggccttc   7380
cgtcggcatc taaaagttct tcggcatcca gagccatcat gttctcaaat gttctgacca   7440
aaaatttatc tgacaaataa tccttggcct ctgagcctgg ggtcttgtca gcctttaaat   7500
caatcagctg tttaaccgga gaatcttcac tctcaggatt catccaacta gacgtatctg   7560
ccagatatgc caagatctct tcttgagtga acccctgctg tctatacaac caattgaaga   7620
acgtgtccat aaattctatg aacagaggga aatcattctg gtagaacaac ggagtttcat   7680
acttaacccc gttgtgtcca ttattaagat ctttggacat agcgcacctc tggcgtaaca   7740
accacatcac caatcttgaa tacttggttt tgtgtagcct gtatgttctg gttcagtcca   7800
tccggtaaca cgactatggt caccccttca gggttatagt tagagaccgt gatctgctga   7860
aggtctacaa ccccatttgc ataatccaca acccctgttt tttgaactaa aaactctttt   7920
gtcgtgtcat tgttattcac tttatacatg ttcagatcgc cattatcgtc gcgcatgtag   7980
taagtgaaat ccacctcggc aggaagcggt ttgaaccccg ttattttcac agaaccaggt   8040
ttgatacttc gtccataact gaatgtgaaa ctgtctaaga ctccataatc aggtttgaaa   8100
tggcgtttat aaccaactga agtaatattc gagttgatag aacgttccat ttttgtaatt   8160
gcttcctgca atatttcttt gtcaaacaat tggtcaaatc cgccgagatt attttcaccc   8220
catttaacga tactgtttcc aacaacaact ttcatctgtt cttcaacgta gactgtagaa   8280
gtaggatccc aaaatatagt cgttgagact tggatatatg tgatctcgga gtctaccact   8340
```

```
ttgggggtaa tagatcccac attatacttg tccagagcag caacgatatc ggccttctca   8400

gcgtccgaaa gtgtctcacc aacagaaggt ataacagcga tgtaaacata gccagaatca   8460

ggaggagaca gcgtgtcacc accatatgat ttagctcggg agacgttgga gaataacctt   8520

tcagtcaata caccataatc tgtttctgta accgccgcac catcagcctg ataagctaaa   8580

ggagccaacc gtttagtgtc ctcaatagat tctggatcgt ctccacctgc gctacgttcg   8640

gaaaccaatt ctacgtcgac ctggttaaac ccgcctatgg atgacgctga tgacaggctt   8700

gtgatatcat tcccatcagc accagaagtt tccaagtatt gaaggaatat gacgttccca   8760

tcttctactc gacgcgaaag ataaccatcc ccgaattcaa acacatacag accgtcaata   8820

cccaattcta cgaaatacag gtaagcatat tggctcagat caaatggact gttgtaacgt   8880

tgatatgtcg tcgaaacgtc ggaagactct gattcttgta cttgcacgac catatgattg   8940

atatcgacat tcccagaagg aatcgtatat gttgaaatcg cgcttccttc aacatcatat   9000

gtcttgtaca accaattccc ctgtaccaac tttacattgt tgaacatgta ataaccgtct   9060

gcagtcaacg ttgctgacac tggtttctca acagtaaagt tgtaggaact gccgtctttt   9120

gccccaacga acattacgcg ccgatccatg atgatctcat tgggggctgt gctggcgtca   9180

taaggcgtaa ctttgatgtt gacatacatg tatgctgccc gatagttgtc aggcgtgtag   9240

gaaagaaatg cagcagataa accgacgttt gaacgttgat ttgctgtctt caaatggcct   9300

tcaccattaa gcatgttttg cataaaggct atggcgttcg cgtcagatgc caacaaacga   9360

ataatcgcac taagaccaga accttcaaag tcataatctt taaaggtggg atcagctttc   9420

attcgctgtt taataatgta ttcaaatgct ctgacgtcga gtgaaggaac tgtttgcgtg   9480

gccatgataa tctccatcac ctgagtttga atatggtgtt gaagatattt agccaacggg   9540

aatcaaaacg ctcgcgcgcg tttaatttat tcgaatatac tcgcgagggg gctgacgccc   9600

tcgctcgtaa caccgccttg acaggcagtc ccattccaca gccatggagg ctgcttctcg   9660

ttgttcgtta acactcacaa ctcgaagggc accgcgttaa gatacagttt cttgatgttg   9720

tagaaaagta gtttttacct attaataatc actgtcatta ttttattggc cattcctgcg   9780

tttatattca ataaacgtat ctccaatata ataatggaga catttaatca attcggtgag   9840

gctccggaat gcacattaac acagcaatca tgaaacacat tattccttta ttggcaaaat   9900

acgaagggga acgtgccacg aaaatccctt ttggaacaat cacagatgaa gtgaaacgcc   9960

tgacgggtaa aagtatcaat ttccgtcgcg ttgttgaatc tgcgttagag ttggcccgtt  10020

ctgatttaca aaatccaaca ttttcattta atattgacgt aacttcttca cttcgacaag  10080

aattggaaga atcatcacaa gcgcggcgcg atcgtttccg tcatttatat gttcgtaacg  10140

aattttccga aggtcgtgtt ggtatgaaac tggagtctat tcgttctgat atttgcttca  10200

ctgtcaacta tgttttagag ccagagagcc agcgcattta ttttggcgcg attatcggtt  10260

tctatgggaa ctctattaat ggttgggcag aacgtgttgg attaaaagaa acccagaaca  10320

atcattccac accttctacc cattatatga cgcatgaagc tgctggcgaa tatgtttacc  10380

ttctgcgtcg tgttgtgaag ttagaagtgt taaaataacg ctttattcaa taaataattg  10440

tagtaaagtt agttgcatgg aagggaggga acactatgtt ttacatgatg ttactcctca  10500

tcctcctgat cgggattacc tgctctctcc tgggtctacc cgatcagtcc ggtaaacagt  10560

tgcccacttc ggcgcatccg gttttgagtg aaggttcgtc cgcactgctg tgggcagtgt  10620

agctcaaagg ggagaggact tttcaaatta gctgggctac ggtaaagtat taaacacgag  10680

ggaaataaca cagtgggagt cgggtttgca gcccaaaacc agttaacccc tagtctcagg  10740
```

```
ggcttgtgtg aatagaggcg taatagccac ctcgctggtg tcagtggacg cacttgaccg  10800
tcggagaacg aaactccctg ttgtagcgtg attagctcag aatcagagag caccccgttg  10860
gcaagtcgac accaacatat aaggggaggt cgggggcgct aatctccatc acgccgacaa  10920
cattatgagt cttccacaga gggttcataa tgttgcgtca aagggcaaca aggttcctgt  10980
tggttgaatt aacttgattc atagttcctg ctgatcttcc cggattcaga agaacaccga  11040
caggacgagg ccggatgcgt aagttccggc aaatcgatgg tgaggtggtg cattggtgac  11100
acggggtagc gcccagaagt gtggttcgat tccacacct ctccaacaaa aataaaaggt  11160
tttatcaata acgggttaca aagtatagtt aactcactga acggcaagct gtttgagtcc  11220
tggccactca tagcgatgtg agaccaagac aggtaggttt aggactcaaa caggttttcg  11280
ttctcgttgg atgcgacttt gcgggttttt agaaactgac cacaaagata aatgcaaacg  11340
ataacacgtt cctggcagta gcttaacagc catacaccag tgaggtcttc cgattcctca  11400
tcaccaaatt cggcgcacta aaataggcgg gagggtgtga ttaataagct cccgccgaac  11460
aatgagcgga gcgtgtactt aataggtcga tgggagcaga ctacttctga gaaatcagga  11520
gcgtacatga gaaggttcga gtccttcctc caatcccaaa gccgttatat ctgactgtcc  11580
aaaggggata agctcctgag taagcagagg tgggttgcct aagtcagatg ggatgtaagg  11640
tcagcgctgg ctaagcattt gggttcgact ccctaaagcg gctccacatc tttgagggca  11700
ttccgcgtca gacgcgagac tgtatggagt ttcaggagaa aggcaactta aatccgaggc  11760
agtaatgccc tatgaaataa cggagcctgt tgtacactga gtgccctcaa agatgtgtct  11820
cacagcgcat cagtttgcag ttatgcaagc ttcaataagt taaaacgcgc ctcgggcgtt  11880
atgggataaa gccttaaaca gtggaatccc cagggctagc aatccctgtc aaagaagtag  11940
ccgtgtgggg gtttgccccc acaacgcaaa tcgaagttct ttgggtatat cttttaaccc  12000
tcaaggtctg tacacagaag tggccgtccc atgagtaagt taggcgatat acaacatgtt  12060
gggtcgaacc tgttaagccc agagaacttc gatttgcgta cttgagagag cgttgtatga  12120
aatagggcaa tgccttgcag acctcgacac ctacatattc tagacactag tgggtgctgg  12180
cgaagatctc aaaataagct ggtcatcaag ggtagctccc tgacctgacg aacaatgaga  12240
ggccgaacta aggggaaacc cgagacaggc gcagtattct tgagttcgca aaatgaagag  12300
cattaaagaa ctcgcaaagg acctgaaaat tggtatccct ggcttgtacc actgagtgtt  12360
cttcatcttt gggtgattct atgttgtcgg gctatcaacc catgcttgct ggagcaacca  12420
gtggctctga atcaaccagc cagcctcgtt tggtccgagc gatagaggac aagtattctg  12480
tgtgacgaag acattgaatg cgagttgtaa catttggttg caactttgat ggctctggat  12540
tttataaacc atgtctatgg gtgacgcggg atctttagta ccagagccat caaagttgtg  12600
tccaacccga tcttgcaagc ccgtatccct gtatggtcaa gacttgcaag tggaaagccc  12660
tggaaaaata aacgcctgtg gtgaggctac ggtgcaagcc aaagacccac agaagcgcgt  12720
tgccgtgagg cgcacaaaca ggcatgcatg aactgatcat gcacaaacgg gataaagggt  12780
tgagagacct tggttggtca cacaataaat tatggggcga tagtttaagg gacagctgtc  12840
cggacagcga gtccccagag agaacaggct ggcggccaaa ccagcaagga gaggtgaaaa  12900
tcctcagacc ccgccaaatt ttggccccgt agctcagtgg ttagagcagt cgactcataa  12960
tcgattggtc gctggttcaa gtccagccag ggtcaccact aaataaacta gttgttcaat  13020
aaacaattgg tgagtatgat gaaaacgttc ggtgattttc ttactgagtg ggatggtctc  13080
```

```
gctaccgaca acaaagagat tgttgagttt gttgaaaagc gaggcgataa gtgggttgtc  13140
cttgaccaca ccaagactaa agttcttggg acacatgaca ccaaagctga cgcggacgcc  13200
caattaaggg cgatcgaagc gaataaacat agttgaaggg ttctatatta tgaagaatat  13260
ttgggcggtg atttccaaca gaattcgcgc tagttgggaa ggtcggatgg tgagcatcaa  13320
gaacgggtct catccaaaaa cttacgatcg ttatgatcct gccctggatc ttcatgcaga  13380
ataaagagtg tttacgaaag taagaataga gacgatgtag ttcagtcggt agaacggtgg  13440
actgttaatc catatgtcgc aggttcaagt cctgccatcg tcgccaaatt gaagtagagt  13500
atctcgaagc gccttcggaa gtgcgaatcg cgcgatagct gccaatgtaa ggctgcagga  13560
tacagatacc caggggagtg agacctactt catacaattt cagagtgtag aggctacagt  13620
agtgcgcacc tcacggaaag ctacaccgga cactctgata caaatctacc accgcgtgga  13680
ttagctgagg aaggatggcc gatgtcctca agcgtggccc agcacgtggt ggtagaccaa  13740
acacagtaag cgttgcagcc agctgtgtat aaaatggggt gactccacat cggaaacgat  13800
gccccaactt ccagaaatgg tcgggcgtga agcctgtaaa gttccaggag atcgaaccag  13860
aaggcactgg tgtcagttaa ccaatcggcg ctgataagcg cggggagttg ggctacggca  13920
gatcaaatgc acaatcgggt gtgaagcccg tccaaattac gctcggtcaa gcagtctgtt  13980
tgtagacggt cggtgcgggt tttgcaagac tcgtttagac taacaaatgg atgaggcgcg  14040
actctctggg ttgatcacca gagtgctggg gttcaaatcc tctaacgagc accaaacaac  14100
gtgagtgtgg cagagcggtc gaatgcgcct gactgtaaat caggtatccc acgcggtggt  14160
tcaaatccat ccactcacac caataagtcg tttcggtcag gtcaagaacc cagatttagg  14220
tcatggcttg gaaattcttg accgaagcgc agtatacgga aggttgcccg agaggtttaa  14280
gggactcgac tgctaatcga gtggggcttt tagcccccga aggttcgaat ccttcacctt  14340
ccgccaaatt gcttcatagc tcgagtggta gagcgcagga aagtttcgag agaacaaggt  14400
gcctgaggtc actggttcga atccagttga agcaatcaga ataatgagtg tgacttcctg  14460
aagatgaaga aggtgtgcat gccgacttca taacaatctg gggttaagga agttaagaaa  14520
gtcgcaggat atgcaagtga aatgcaaata gctttcaacg tcctgacgat ttcgggttcg  14580
attcccgacg cactctccca aacgcctaat actagaaatt gctgtgagta gtctttccat  14640
ccccacgatg gtttaacata gcccgatcag gaagatcggg cttctttttg tctataataa  14700
atagatctga cttgtaaagg aggtctatta tggcaactgc taagatcaca ccaaacgcaa  14760
gtacatggac gcaagtctca gacggcacat ctttgaaaac tcttcaagtg actcacggtt  14820
ctgtgtatct gtgtgatagc cccagcgctc caacgggtaa caacgcgcat atcatatatc  14880
aaggaaatat ggtcgtttta accccgccga cggtgggttg ggttaaggca attaattctg  14940
atgcgacagt tatcgtttct taaggagggg gtatggctat tttgacatct ccctatttgg  15000
ggaatatgct tcagacccac cgcattaaaa cagaagtcag attttctggg ttgtcacaac  15060
tgctaacttc tggggcaact ggaatagatt tattaactgt gttggatggg aagactccga  15120
acccttcttc tcctactggt ttggctccgt tttttaaatt atcagatcac aaatttcatg  15180
cgtttcccta tgattctatt cttcctgtga aggttaatat tgtcggatca tggtctgggt  15240
ctacttctaa tagaactatg atattagatt ttgtgggttc tgtggggaac cagttatcaa  15300
gaagtcgtga tgctagcgta ccaccgccgg acactttgtc tttcattaca ttcttcagcg  15360
ttgacaagga tgggaacctg gcgaccaacg gagcgcaaat gaaactgtac tcttatggtg  15420
gtgactttac cattaccgag gtcgtgttga tcgctgagca ggttgtccca ctctatatgt  15480
```

```
ctagtatttg atttgttcaa tgaggaagag gggtttaaaa tttaaccgtt tataaacccc  15540
ttcattgatt tgaggaaaca acatgcgtaa tgttacgatt tgggattaca acgatgtagt  15600
ttgtgacctg cctccatttg ctcgcctgta cacatacaaa gggaacaaac gtactcttaa  15660
tgagttcttg tatccggcat atatctatcg ggacgggcat cttgctccgc gatcacttga  15720
agaaactggt gtgtgtactc cttttgatat caacaagaaa gggcaagcgg tattcattgg  15780
ttattccagt gaagacgaca tggtaaatgg tcgacgcggt ctgtatatgg tgttcaacac  15840
atttgagcaa gccgtgaatt ggttattcaa aaatggttat gatttctatg gtgaagagag  15900
ttctactgct cgccgccgta aagtaaagaa tgttgatttc tactcagagc gcaagaaata  15960
tctggacatc gctcatcagt atgagcagtc taagaaatcc gttctgatca aaccatgcgt  16020
tacggtcggt gaagaagtgg gtgtcgtgga taattccgat ttgaatcagg caattaaatc  16080
tttgaagcca actcctctgg ccagtggtgc tccggttgtt aaacatgaca gttcaatccc  16140
gacaccgcct actcctccgg ccagtcgtgt tctgaatgat cagggcgctc cggtaaaaca  16200
aaaggtcgag aagccgactt tcatggataa catgatgaag ttccttcgtc tgttcaagaa  16260
gtaagccgag attctccttt tctatactcc tgtagatacg ctatgataag ccaatgtcta  16320
caggagaaat acaatgaaca aaaccatctt cgataccctt tccctcgacc gtaatctggt  16380
tcactgggaa gattatctct acaaacacac cccgtgcgaa cttattgcca atccagaaac  16440
caatcagcag gtttggttca aacgtgaaga ttacttcgcg cctttgtcat gctatatgga  16500
tggcaagcag gggatcaatg gcagcaaact ccgtcaggcc atctggctca tgatggagca  16560
tctgaaagct ggaggatccc cagatcttat ccatggtact gtcgttggta gtccgcagtc  16620
ccctatggcg acggcagtct cacggcattt cggcggcaag acaaccactg tgctgggtgc  16680
cactaaacca accacatgca tgaatcatga tatggtttca atgtcagcat ggtttggtag  16740
tgagttcaac tttgttggat ctggttacaa tagcaccatt cagccgcgct gtaagaaact  16800
cattgaacaa ttaaatccaa aggcgtatta tctggaatat ggcattacat tggatcatac  16860
cgttcattca ccagaacgca ttgctggatt ccatatgctg ggtggtgagc aggttgccaa  16920
tatcccagac catatcactg atctgatcat tcctgctggt tcttgtaatt catgcaccag  16980
tatcctgaca ggtttggcga tgcatccgaa accaaatctg aagaatgtct atctgatcgg  17040
gattggacca aaccgattag atttcattga aagtcgtttg cgcattatcg gtaagcaagc  17100
aaacctccct cacataactg atttcactcg tcgctatcac gacaacccag actatgtgta  17160
tggtaagaag gatcttcagc atgcctctaa gagcgtttcg ctggctggcc tcctaagtgg  17220
tatcaggcca aagaacgagc cggatatcgt gcttcctcgt tttgaggtac accattggga  17280
tcttcatacc actaattggg ttcgttacaa cgacctcatg gattaccagt ggggagatat  17340
tgagttgcat cctcgttatg aagggaaggt gatgacatgg atacaggaac acaaaccaga  17400
attgcttaat gagaactcat tgttttggat cgtgggtagc aagccatata tggaagcgat  17460
gaaagctgct tgccctgaat tatcaatacc tgaacatgtc cctgtgaatg agtttgtccc  17520
cagctaatcc atcctaaata ccccatacaa ccagtgtggg gtatctatga aaacctttct  17580
agaattttat cgcgaatcaa cgttacctga ttttacgaat atcgttttgt atcatgggtc  17640
taatgttgaa ttcgatatct ttgattttga aaaatttggc cagactgact ctggtacgat  17700
gggtgctggg ttttacctga cgggggatcc agaaaaggca cagatctacg cagaaaatgc  17760
cgtgcgctat cgtcaatctg gtgaacctat tgtcatggca tttcgtgtca aggccaagaa  17820
```

```
gactcttgta atagattcca acaatgtttc ggtgtgggaa aataaaatgc gagagttggg  17880
gataaagcct ggtaagatac atgataatgt gaaagaactt atcaacaaag ggttcgattc  17940
tatagcctct atgagtgcca ataacgttga ggaaatggtg gtgtttaagc cagggctggc  18000
gaccagagaa gcctaaatag tccaaagcgg tttattcaag aggacattac catgccaatt  18060
tcgaaattat ttgaagcgga ttccccagca gatatgccta tctggactgg tgttcaagac  18120
gggacaacga ttgaattctt tgagcgcggg gaaacaggcg ctgaagagat ttatgcttcc  18180
gtacaaggga cagacgtcgt ccgcgccgct gtagctcttg ctacattttt agaggacgcc  18240
ccgattgacg gtatcccgtt tgaagcccat gtggacccag aagacccgac gtctatcatc  18300
attacagtcc agggtgctga atatacatct tacagtattg agcacgatga agaaacaggg  18360
gcgctgttta tagccacgga tcttcaattg gaagatgacg aaattgaata tctgaaacag  18420
aatggtcgtc ttccagagta ctctgacgaa gaattggatt ctgcgtttga caacgtagac  18480
gatgatgacg atttctggga cgggaaataa acaaaggggc ttaagcccct ttgttttaga  18540
tatcgtttgt gtgtactgtg aatctcattg ttacgacatc tgttctttca tccttgtgta  18600
attcgaactt caaaccttcc ttcagaagac tcgccgccaa caatgttttg aacttttcga  18660
cttgcttgtc tgttgggtat ttttgagact tatatgcctg ttgaaatgct gttaatattt  18720
cgtcaaacct gttgccacca acagcgtaca ccatgtcatc aatttcaact ccgcgatttg  18780
cttgggaaac gagttgcttc ttcattttgc aaacaaagat atcaacggct ttttcaacta  18840
tccccatggc ttcccaaatc tgagcctggt caatcgtagt ctgtaattct tgtgcgaagt  18900
ttttcatcat ttcaccttcc tcgttggata ttggttaaag agtttgccca gcttggacac  18960
attgataatc gtctgagtct tccagcgctc gatcccctct ggtgtagtca cggttaggat  19020
tgaataaccc catatatggg aaccattcag cacagccgcg ctgtgcccac caattttgtc  19080
ttccagttta caaatgaaag actcatattg catcgcagcg tttcgacgtg cttctttgac  19140
aaacagagca tggcgctcag gatcagcttt gacaatatcc ggcttcccag gtatgtaaga  19200
aggattcact gcctgggtca aagaacggta gagcgcatgt tttgatttca ttcgttggta  19260
atctggatca ccaaacttga caccaaccga agatggccac ggagcgcact tctcgacgtc  19320
ccagccgttg gatgccagat cgtccattat gttcttgatg actttgttcg cgtactgctc  19380
agcagcattc tcagcatcaa ccagcagagg ctcaactgcg atacggacag gagtttttgg  19440
catattcatg atatagtcct tcagttcaaa gtaagccccc gaaggggctt tgtcatatta  19500
gaggcgggaa tccaaccatg cgttcttttc attctgccat tcccaagcgg cctgaccacc  19560
agccataatc acttccagag aaggagtatt gtcatcctcg ccgccgtgaa gatctggatc  19620
aaatccatca tcttccggat catcttcaca ttcgttctga tatgcggaat attcaatata  19680
atgcgcttcg gcttcgcaat ccatgtctcc cagagcagtc tcaagagtca ttttaccttc  19740
ggcaatcagc tcagccgttg cgtcgtccag acctgcgtct ttcgcttcaa caaagagttc  19800
atgacgtttc tggaagagaa agaattgcat ggcggcggaa cgtgaatcaa agaattcttg  19860
acgaggagcg gtgatatcac gcccatcaat tttacttacc atcacgacac gagaaccgta  19920
ctcaaccagg aagcgaccgc cttttacggg gttgctgccg tcaactgtgc ccaaagtggt  19980
gattacacgg ccttcttcgg tgccgaacaa tacagttttg ccggatttag attgagcgat  20040
aatttcgatt gccatgatgt atttccttct cttcagattg ttgtttgttc gtactacaat  20100
tagaagtata cgccagttat tgaagaagta aactttattc aataaatatt ttaataaatt  20160
ttgaattctg ctcctttgta cactgctttc cctcgttcta taaggccgtc ggggacaacc  20220
```

```
acctttgtgg gccatccacc gtccggtgcc ttgacagtca ggcgtgtctt atgatcacca  20280
agctgaatct gttcataaat ccttcctctt actatcgtcg ccccgccttg ggtgacaagc  20340
aatctcttgt ttaccacttt cattccttaa caccaaaaga aaggggagtt tcctcccctc  20400
taacttattt cttcagatca ggccacgcac cagaggtcgc agtagaccca gctgggggag  20460
cagactcaag atcgggagaa cccgactgag taacaacagt gggatctttg ttaaccactt  20520
tgaccccaaa ctgcttgaga gcatccacag cttgcgcctt ccggctgttg cttttgtaat  20580
ggttataccc cttgataccg aatgatgcac taattgctgt caataatgaa gctgtatacc  20640
aatcaggtgc tgtttcaagg gcttgcatac caccaattac tgctttgatg aaatcccctt  20700
tatgatactc ggtggggaac attagaagtt ctacaaccgg agcgatcatt acaaggatag  20760
cgggaacagc taatacgata gtccagaatt catctttcca agacccgccg acttcggtga  20820
tcttagacag ctcccaatct gaggaggact tgatagcctc cagctttaca tcgtgtttag  20880
cctgaacaat ttcccgcttg tattgcacca aatcagtccc aagattccag agttgcttta  20940
gcgcccctgg gatcatactc acaaagggga ttgccataat aaactccttg gtcattgaac  21000
gttcctcggc taaattacgg ggacgtgctg acggcacggt taaccggaga caaacaatga  21060
ctgttttcta tacgaacgtt gcccgacagg gtaacgacct tctgattcgt attgcagacg  21120
acaacggcaa tcgccgtatg ttgcgtaaga aattcgaacc caccttgtat ttacccacag  21180
ccgattattc caaagttgaa aagattggcc tcctcaatga accgttggtg tctaaaaaat  21240
ttgcatcaat gcgtgacgcc gacaactatc tggaggagta taaggaggtc gaaggcgctg  21300
ccgtttacgg gcaaacggat tatgcatatc aattcatagc acatagtttt cctgggatga  21360
ttacccccga ttactcaaat attcacatcg ccaacgtgga tatcgaagtt ttctcggctg  21420
ggtggcgcga tggagaaatg actaaaggtc catttcctca cgcgacgatt gaatcccaca  21480
cgtttaaggg gagcgaggcg cgtgttcgcc gattccataa gcaagtgttg gccaaccatg  21540
atttcgttcg agagcatttc ccaggttcct ttatttccaa caacgtgact gaccagttcc  21600
ctatcattga tagtaatggt aagatcacac agaacatgaa tgccgccttc cctattacgc  21660
tcatccagct tcaagacatg aacaccaaca agttctatgt ctggggtatg ccgtgttcta  21720
aggatcgcca taaattcaaa tatgatccaa atgatgaaga gataggtggt cttgaggttg  21780
aatacaaaga atacacgact gaacaagaac ttcttcgcgc cttcttagat tattggtctg  21840
aacgtcaatt tgatggttgg actggctgga acatcgaaac gtttgatagc ccgtacttgg  21900
ttgaacgtat tacgcaggtt ctcggtgaaa cccaggcaga gcgcctcagt ccttggggca  21960
aactcaagaa acgtttcatc aaagaccgta aaggcgacgt gacttcttat caattcgtcg  22020
gttgtcctat gatggactac atgcaagttt acaagaaaca cacgtacaca acccgcgaaa  22080
aatactcact ggattggatc gcttattgtg aactcggtga gaagaagttg gattatagtg  22140
aaagcaaatc attgtatgat ctatatttta atgattattg caaacacacc cgatatggta  22200
tcaaagacgt caaactcgtg tggcgtttag aacaaaagct gcgtttgata cagctgatgt  22260
tcgtattggc gtatcgcacc aaatctaact atgaagacgg tctggggact gtagcaccat  22320
ggctggcgat gtgttactat cgtctttatg aaaaggggat tgtccctaaa atacagcgtg  22380
tgtatgatgg tccaacggac tttgaaggcg catatgtcat ggaggttgca ccagggatat  22440
atttctgggt attctctgag gacttaaact ccctgtatcc ccacatcata cagcaataca  22500
accttggtcc tgagactatc gtatctgaca agcacacacg tcgcgatatc attgagtcca  22560
```

-continued

```
tgtgtgagga attaaccaaa gcgatgaatg atatgacaac gcctatgaac aagcgccgtc  22620
atctcaaaaa tcttcacgac aagctgcagc gtgctattga tgaacgcata caagttgttg  22680
atgaattggt cgcgctgggt gaattccatt ttgaaacgtt acgccgttat aacgtttcgt  22740
ttaccccgaa cgttcagttc ttcagtaatg agaagatgtc tttcctttcc gaaattatgc  22800
gaggcatata cgctgaccgt aaaggcgaga aagcaactgg tctgaagtat gagcaatggg  22860
ctggttggtg taaggaaatg tctaaaggtg atttccacct tgaatctgcc atgaagtctc  22920
gtttctacga tcctgaatgg tatgaagaac acaagcatat cgaccttgat cacctgactg  22980
aagtcatgca caagtgggaa gatttgggag ttgcccaaga tacgttacaa caaggtctga  23040
agatcttgat gaacgcagga tatggtgcaa tttctaacgt ctggtttaaa gaatacttca  23100
acatcaacat cgctgaagca attaccactt ccggccagct gatcaacaaa tggaataaac  23160
gacacacaga cgattacctc aacaaactct gtggcaccac tggtcaggat tttgttatcg  23220
cgggtgatac tgactccaat tatatttgca ttgaacgcct ggtcaagcaa ttgtggcctg  23280
aagaaaagga ccatcacaaa ctcgttgata acattgacca atggatcaaa gagaattacc  23340
agccaaaaac cagtgaatgg gcgcagttgt tgtgtaatac catgaacggg tttgagcagc  23400
gcatggtctg ggaacgtgag gtcatcgcat cgtctgctgt atggcgagcc aagaagatgt  23460
attgcatggc agtatacgat agcgaaggca tcaagtatga gaagccaaag atcaaattca  23520
aaggtttgga agcgcgtaaa tcaaccactc ctgagtggtg tcgtgagcgt ctggttaaat  23580
gttatgagaa agtcctgctc ggtactgagg cggaggttca ggaattaatc gctggataca  23640
aaaaggaata tatggaactc accgtggatg atatcgctca ggcatctggt gtaagcgata  23700
ttgagaagtg gttagacgcg aacgggaatt acatcagtgg cacgcacttt gctgccaagg  23760
cttgtattat gtacaacaag ctgatcgata agcacgaaga tctcggtctt ccgcctatcg  23820
aatccggtga taaggttaaa atcattaacc tgaaacctgg caatcctgtg ggaatgatc  23880
gcatagcctt ccctgacttc cttcctcctg aattgggatt ggataaatgg gtggattacc  23940
acaccacgtt tgaaaagacc ttcatagagc caattcagtc tatcttggat gtggttggtt  24000
ggtctcataa acgtcgagtt aatctgttgt ccatgatggg caagaaaggt tgattcaata  24060
aaccaaaggg ggatataatt ccccctgtta tccctttgac aacaggtatt gttatgaaac  24120
tcaataagat tcttctggtg tgtgctctgg ctttctctac cactgcatgc tctacccttc  24180
tggacgttgc gtctaccgtt gacctcgatg cgccgacgtt caccaatcag caagcggtga  24240
ataagatgga agacaccatc aaggcacatg cagctttgga caacaccact cctggtccgt  24300
tgcaaactgt ttgcaattat gatgattcca tccaggaaga tgaaacctat cactgcacca  24360
cttacgtgaa ggaatcttct gtggttctgt atgcagattg cacagaagag caatgcaccg  24420
caactggtta tgatcaagtg gagaagtctg atgaataatc atgttggtct gtatgatgcc  24480
aattctaaaa tcggtggaat gtatcgtatc ctggtagacg tagacttgac tttggttgat  24540
agcctctccc cttgggtgga ttggtttaat atttccaatt caaaagctgc tgctgaaaac  24600
atgggttgtc atgattatcc caatgatttc cagcgtatca ccaaagagtg ctatatggct  24660
catgctggtg atttggcgat cctcatgcgg gaacgcgcgc atccggcctg gttaacgcgc  24720
cgtgtattcg ttgctggtca atggatggat tcacctacag gacgtgatcc tatggattgg  24780
tggcgcatgc cggacctgta tgccaagatg aacccgcttc caggcgctta cgatttcctg  24840
gtgaatctga agaagatcct tctcgaagac tttgaaaatg ttgaattgat cgcagtatct  24900
aagtgtgagc cagaacacga gcgcagcaag cgccagtttg tctatgacaa gttccctggc  24960
```

```
atcttcaacg ggtttgtcag caccgacgaa aagcatcttt tggcaggtga tgttttaatt  25020
gatgataacc cgaaatacgt tgaaccctgt gcgatgaaca atatttttgt catctttgtt  25080
cctcagggaa attatgaaaa actggatctt tcgaactcgg aagatatgct ttatattaaa  25140
ccagtagaag gccagaacca cttcgacttc ctgaaccgca atattgtcga agtggtgaac  25200
cgcctgattg gccattatca atacgtccat tgaggaggac atcgtgcaag aacaatccaa  25260
gtttggggaa accccagaca agcgttccgg tgatagcgat atggatggcg ttattatcca  25320
tgtgaacaac ttcattcgta aacaaaccac acccacttcc gttggtgcgg cgctggagtt  25380
aaagcgtgtt ctgatagaaa acggtatggc accagatgac gatgaaattt tctataactt  25440
cgaagaccag tataaagtga agtttgaaga gaatggccgc ccgcaggttg ctgtgttctg  25500
ggcaccatgg atgggcggtg tgagctggcg tattgaggaa gatgcataat ggctaaaata  25560
attgtagtga aaggcacctc ggccacgggc aagggtacga gagtggtcca gttcatcgaa  25620
tggctccgaa ctaagctgga gcctactgaa ctcacctaca ccattggtga caagacgcgc  25680
ccattcggcc tgaagttcga agagctgaag ttaatcttcg tcggccagta taccgtgtcc  25740
aacaaatccg gtctggcttc ctggacttcc atggacgcca tccacgccgc cacaggctcg  25800
ggtgatatcg cccgtgatct ggtcaaaggc tggctggctc agggttacac tttggtgtgc  25860
gagggtgaac ccctcatgct atctgataaa tggcgtcctg aatggatgtt caagaactat  25920
ccgattgaat ctctggcgtt gctttatttt gcatacccag accgctatca gtatgatgca  25980
cgcatccgtg gtcgctctgg taaggaagca ggggactccg gctggtcacg caacgaatct  26040
tactccaagg agtttgagaa gtcgaagact gaaatgctgg cgctgggttg ggaagtggtg  26100
gtcaatgatt acagcggtca agacgtgttg tatcgccaat cgtctacaaa cactcaagaa  26160
ttcaaaacag gaaatgatag cgaattagcc atgatgccgt ttgatgcacc tttgtgggtg  26220
attggcaacg ctattcatca tcaaatgcgt ggtgagtttc acgccatggg tctggacatc  26280
aaagatttct acggattctg tgaaactgac ccaatgacgc gtgaagtcgg tggggatgat  26340
cctctagcgc atcgagtccc tgagaaggcg accaaatcta aaaccaaggc gagcgccaag  26400
ggagaggtaa caaagtcctc tgtatccctt ctcggcctgt tgagtaaggg ttagaaatga  26460
aacagatgtc taaatatttt gtgttcgtcg gattggtgat gtgtatcaca gctgtgcttg  26520
tcggtgtcat gaaatatttg ggcatcgttg agttggattc aaccgaaata ttgaacgttt  26580
acgcgttata ttatttgggg ggtgctatct tattaacgcc tttcgtctat aacataattc  26640
agagtttcaa aaggaattaa aatgaaaatc ctcattccac gcaacgttgt cgctgttgct  26700
attgattacc gtggtgatgc gaagatgatt aacgctgtcc gttattatcc ggaacagaat  26760
aaaatcgtcc cacaatttca actgaatacc aatccttctt ctaaggattt cggttcttgg  26820
cgtcaggtgg gtttggctcg tacccaagtc aatgcccagc attttatttc cgaaaagacg  26880
aaaaccgcca agcaaatttg gttggtgacg aatgatcgtc gtttcctgcc tatctggtct  26940
ctgggacagc ccgtagtaag ccccgaagaa attcagctgg ctcccgaagc tgagcctgaa  27000
gttgtttctc ctgtagagga agtgaaagat gaaaatcaag catgttgatt ttatcttcat  27060
gatgctgatg ttcgttatct ttacggtttc gctggtcggc gtcatggtca cagaaggggt  27120
gcaacagcgc ccattcttgg tgatctgtcc agtatcgatc gccactttct tctatctggc  27180
gttccgtgtt gaactcggga gtaaaatcgg atgatacaca tttctaaaat gccgcaggga  27240
tataaagccc ctgaaaaatg gaaatacccg attgatctgg cagtagatta tcgtaagcca  27300
```

-continued

```
gaaaatcgca tgtacctgct caaggcatgg gtggaggcgc tatcctacac tgaagagcat  27360
aaccagcaag tccgtctgat ggattatgcc atcgaggtta cagaaggcat cacacagctc  27420
gaaaagatcg agcgcaagat ttggatggcc tttttgtggg gttgttgcta taatgggatt  27480
ggaccatgga caatttacag tgaatttcct gtaccccac aatctccgaa agagtttcag  27540
cgattttctg attggtataa cctgaacttt gatcgtatgc gcttcgatac agattgtcgt  27600
tatcgtaagt cgaagatgat tccgtgcgtt cagtcctata tcgattggtt gggtggtaaa  27660
acccaaatgg attcttttcg ttggatgttg gaatgcacta ccaaggaaga ccagttcacc  27720
gaactgtgga atacggcgat gtcatggaaa tacttcggtc gcctgagcgc atggaacttc  27780
ctggaagccc tgaacatggt cttcggtaac atatgggata tagacgtccc tgggttcatg  27840
ttgcgtgacc gtgatggtag cgaatccaat cgtaacggcg cggcgttctt atccaaccgt  27900
gatgattggg tgaccaagca cgggaagaaa aagatcaacg gttgtcctat tacagacgaa  27960
gaatgtgata tactcgaaac cgaccttgag aaagcgtttc aggaatgcgt tgaagagttt  28020
ggccacatca cgtttatcaa tcgtctgaac tttgagacct ccggtgcttg ttggctgaag  28080
aaattcttcc gactgaagaa tacccgttac atcgggtggg acgccgagcg tacatgggac  28140
gagatcgatt atatggaacg tatttggcct gaatactcct gtacacctct ctgggaagcc  28200
cgttcactct ggctaccaga taccctgtta tgtgagaagg ctcctgcagg gcacgttcca  28260
ggcgtccaga agtggaagat gcccgtgttc tttgagacgg gtgttcctct acatatctgg  28320
catttacagc agggtacacg ttgggaacca tctgaggttt acactaatct gaaaatgccc  28380
gtccggaaga tagaggacaa tccgaagtcg accagtgtaa acctcatgac actcttgaaa  28440
cgctgatata aatatcctcg ctataaagtg aggatattat catgttacaa gatctgttgg  28500
tttatgtgct tcctggtgtg gttgttggct tcatcgctgg cgctctggtc ttccgtaaac  28560
acgcgcaaga cggtgaagtg attgttcaga agggtaaaga catcctggaa caaatcgaag  28620
ccaagctgga agagctgaag aaaaagtaat ctgactgcga ttgcgttctt caataaaggg  28680
gaatgggtta ttattagccc gttccccttt ctttttgcaa ggaaataaat catggcaatg  28740
caacgaattg aagacatgtc tgtgctcgat atggaagcga catttggtga ctattttgaa  28800
tctaccccga aacaaaaaga ctctcgagtt ggccgtctgg tagtttctga agcgttcaca  28860
cagaaggttc gcgaaggtct tccacccgaa tatggatgct tccgtaatgg cgcttccgtt  28920
atcgtcatgg gagaatctaa atgacgcagt caggatacaa acaatatttg tacgatctgt  28980
tcatgaaaga aacagacggc gcattacatc ctaagaaagc gaatattgtt aaattgcatt  29040
ctgaaggtga tttgtctata gcatatatcc gaaaagaact cgatttgatg ggaatcgaat  29100
acgaagacca catcacggat acgcgtgctt taaaaagagc aacagcaatc gttcttcaca  29160
ccgttacaac aattatgcat cgccaccatg tttcttttga cgatgcaata actccacagt  29220
atcatgaaga acgctgggaa ttgctcaaat tgaacggggc gcacagttct cataaaaatc  29280
aacttcttgg tatgacgaag gaacaactcg tggatggtgt gttatgattt accttctgtt  29340
tgcggttcct gtaattttgg ccatcttgtt tgtgatatat caccgcaaga ctcatgagcc  29400
aaaggagact ttgatcgcca cggccattgt tatcgtattg tcttgcctta tccagtcggg  29460
attatatgct gctttctccc ttggtagttc tggggacgtg gaaattttga atggatatgt  29520
aactgataag caacggaata aggtgggttg tgaacattct tatgaatgta tgtgctatta  29580
cacaacatct tgctctggtt caggaaataa ccgatcttgt acacaaacgc gtcattgcag  29640
cacatgctat gagcactctt atgacgttga ttgggacgta ttaacaaccg tcggtgatct  29700
```

```
gagcattgat cgtattgatc gtcagggtac tgcagagcct ccgcgttggg cacaagttaa  29760
aatcggggaa cctgcggcac gtgaacattc atatatgaat tatgtgctgg gcaacaaaga  29820
ttcattattc tctaaatctg accagcaatt cgctgagaag ttcaaagagc atatcccttc  29880
atatcctagg gtgtatgatt attaccgagt aactcgtgtt ctgaatatgt cagggatgga  29940
cattcctgtt gattactgga atgactatct gaacaatact ctgaaaacat taggtgcttc  30000
acgtcaggtt aatatcgttt gggttgtgac ttctggccag cctgttgaat attttcaggg  30060
acttctatat gcatggtctg gcggtaaaaa gaacgatgtt attgtagtca ccgatatttc  30120
aaaggatatg aaaattaatt ggggtaagtc tacgtcattt gccgacggca tgaacaacat  30180
ggaactccat tctcgtaacg gactttcatt gactgggaaa ccaatgggca tatccgtgtt  30240
ccaagaagtt gcggtcaata tcagtaaggg atacaaccga gttgagatga aggaaatgga  30300
atatctgaaa tggcgagatc ttaaaacttg ggaagtgatt atcgtcgtgc tgtttggatg  30360
tatcccattt accgcagttt tcatattagg ccgcatgcag tacaatggtc gaacttataa  30420
acgtttgttt taacaagagg atgtaaagat gtcacaacgt aaaggtattt caattggttg  30480
gatcgttggg ttggcgattc tagcatttgc tgtaattggg attggtagtg tggttagcta  30540
tttcaatgaa ttcaaccgca ttgaacaaca ggtcaaaaag ttcaacaaag attctgaaaa  30600
ccacctgagc aactacacgc tcaaagttca ggagacggcg cagattcctg acatgtacaa  30660
aaacggtttg aaggaagtga tcaaagatac tttccaaggc cgttatggcg cagacggttc  30720
taaagcagta atgcaatgga ttcaggaaca gaatattcag tttgattcat ctttgtacaa  30780
agagattcag gttgttatca gctcaggtcg ggatgaattc cgcattagcc aaactaaaaa  30840
attggacgca tgtgcgatct atgaaactaa acttggccag ttccctggtt ctctgatagc  30900
aggaatcttt ggatatccgc gtatcgatct tgacaagaca tgtcaggtgg tgagtgacac  30960
ccgcacccag gccgcatttg actctggtgt ccagactccg attaacttca aaggctgaca  31020
tcatgtctgc gcgagacaaa gagatcgtcg agaacaccaa caagttggcg gaacaactcg  31080
gcattgaaat tgaggtcaag accatggatg atgtcctgac tttcttaaac aaatgtttgg  31140
ggtacgaata atggctctga aacttactga atcactgacg ctggaccagc agcaggcgct  31200
gttggacgaa gtggtgatct ccgctattaa acagggtatc atccgtgacg acacgttgct  31260
tacccgtccg gagatgatcc atcatctggt cgtgtgcctt ggcgaggcca acaaccctcg  31320
caagaagatc cggatgttta aggcggggt gatttatcca aatggtcgtt tcgccttcct  31380
ggagccagtg ctgaagtctg atggcacccc aaataacgat ggttatcata tcaaaacttc  31440
agttccggta actccataca ctgaaggagt tgatgaacta tcttggtttg agacaattaa  31500
caccatctac atcatgtcgc cggatggcaa acccgtccag gatctgcgcg gtgataaagt  31560
agaatccaaa gactaatcgt ccttcaataa agggggatag ggtattattg ctctatcctc  31620
ttttttatgg aatgtattat gtctgacaag ccaagaaaga ttgcaattat tggaggaggg  31680
gtgggcgctc gtactatggc cattatcctt caagaaaagt tgaaaggcgt tgaagtagaa  31740
tgtatcagtg tagacgatat tcctaaacgt cgttgtgaac caggtgaacg catgataatt  31800
tgtgatgatc tggtagaaag tgaacgcaaa acattggtat ctcaagcggt ggctcagtta  31860
cggaaggcag atatttcgta ttgtgaagca gaagccgatg acagagatat aattgcgtca  31920
caacgttatc aaaagccgcc gcgcctatat ggagccgccc aacataaacg tcaggctaag  31980
aaatataaaa atcggagcaa acgaaaatga ctactcaaaa accaacttat gaagaattgg  32040
```

```
ccactgcgtt gatccacatg gacgatgcct tccaagatct ctttggccaa gtatgctcta  32100
atccagtgat gaatgcttgg ggcaagcccg ttaactttgc tgttatgaac aaacaccgcg  32160
aacaggcaag ttcaactatt agcaatttgc gtcaaacgat ggatgtaaaa caaccaagca  32220
tccaacggta tcttgaaaac ttcgatgagt attctttcaa agaccttctg ttcaaagatc  32280
tagtcgagca agagcaacgc agacagagta agaactgctc tgaagtacaa tcttctgatg  32340
aaattcgtca gaacatagaa caagaattcg acaatgcata cgatcctatc ggtttggctg  32400
ttatgatcgt aaaagctctg tcgtatgcag caaaaggaga aacaaatgtc taaaccatta  32460
tctgctgcgg ctgtagcaac ccttgctttg tccgccatgg ctgaagatat gacgcataat  32520
ggtcgtctct gggatgatca tcgttatgca caagggtgta cccctgggga acctgggcat  32580
gctcgtcctt ccgtcagtcg tcctaaaaag gccaagaccc atggaaagaa caaaaagaaa  32640
cgccgtaaat gatgtcatcc ccgaatatcg ccttcacgca ttatcggaag gtgaacccag  32700
atcatcacga tgtcatgtta tgtttcaaga aggtaaaatg atggccgatg aaatcctctt  32760
ccttcgagca gaggtgatcc gtttaagtaa caataaaccc ccaaagaaat gaggatatgt  32820
catgagttct attgaacagc tgatcacacc acaatatgtt tacagcaata ttgtagagca  32880
cctccgctct caattgaatg tgaagcagtt gaacagctct gaattgagtg gtttagaaat  32940
aacagaagtt gaagttgcgg ccttcggtag tcgttatcat tttgttgtca atcacactca  33000
ggttgaacaa gtcacttcga gcattattga cctcggcgca acgaagcctt cccgcgcaga  33060
gccgaaatct gtgacacgca atattgtggg ttatctggaa gagacgttag agccaggtgc  33120
cacccacccg atattcaatt tcaacgccac cgttgtaaac gttcagggaa gttaatcctg  33180
attaaagcct ccgattggag gcttttctat tgaaccaccc gccagtatca taaccttacc  33240
caataatgtg ttcttctttg atctgaacag gaattctata ctatgaaaat gcgcaagtcc  33300
gagcatttcg tgcgctcttc ttctaccatc gtcggacaga cattcaatgt caagatgacg  33360
gataaattat ttgaaacatt attttcaagt ctctacaaat ataaagaggc ggcgtctttg  33420
cgtgagacgt tgtgtaatgg tatagactcg cataaatatgc gtgatcgcca acaacgctgg  33480
atgccatcgc attatgctcc tctcactcct atgcctcaac gatacagcaa acatcttgcc  33540
cccaagggaa ctcctgttgt tgtacattta ccggatgtta tggaaccctg gctggaaatt  33600
aaagattatg ggttggtct tccattagaa atgatcatcg gcgagcctat tacagcgcgt  33660
gaagatgaag tgctggttga aggtaatatc gtcgtgaagg aagacgaaat ccctgatagc  33720
actgctgtta ttggtacacc tggttattat aatggggtac tggtattccg cgctgaggat  33780
ggcgagatca ttcgtggacc tggtttgtat acaacactct tccatagtac aaaagaggac  33840
gacgacgggc aaataggggc gtttgggcta ggttctaaat ccccatttgc ggtatctgat  33900
tcatttacag tggaaagtcg ctatgaaggg aaactgtatc gcttcctgat gtatctgaat  33960
gcggacagaa tcccaactgt agatctcatt accaaagatt tagatacccg tgatcctaaa  34020
ccggaagaca ctgatgagtt caacggcctg actgttaaag ttcctgtaaa gaatcagcgt  34080
tttaccgcct ttgaacaaga gttggtccgt ttgggtcgag tgatgcgacc ttcaatgcga  34140
ccgaaggttg aaaacgccag ttattctttc cgttggtctg acatcaactt cgaaaaccgt  34200
gtaggcaaca catatatcca accgaagtca gattccgaca acatccacta tgctgtcatg  34260
ggcggggttt cttacccgat agatctcgac caattggact ctgaaatatg caccgtgctg  34320
gaaaaattcc cgagttccta taccttcttc gaacttggag aactgaatgt accgccgtca  34380
cgcgaagact tgtcatacga cgaattcact cgtgaaagcc tgaaccgcgt gttcaagcat  34440
```

```
gtggccgaaa atatcatgca agcgaagatg tatgaacttc gccaagcgga gtcaatgggt  34500
cctcttatgt tgtatatgaa aaagactcag ctgactgata tgttcggtag tggtttccgt  34560
aaattggtcg aacgggaatt tcctgtagac aatcgttttt acaaaggcaa gttccgttat  34620
gtgggaacac ccgatgtcgt gcgtgattat tctatggatg cacctttccg ttcattgggt  34680
agcccgtatg atgttgaagt ttatgatgaa ggaagagtgt ttgatgaaat ttatgtcact  34740
tctgttggaa attggctgaa agctaaatca aagatcgctg tcattattga caactccaac  34800
cgcgccagaa atttaaagat acagacagca cgtaataatt tcgatgtggt tatcgtagtc  34860
aaattgaatg aaaattacgc cagtaaccgg aatcagctgg aaattcataa agaggcatat  34920
accaactatg aagagttgaa gtcctatttt gaatcatgga ttggtgtaca agaatcgacg  34980
ccggactatc tggtgtttgc agataaaatg gttgacgttt tcagtgactt attcaatccg  35040
gacgaagtat attttatgca tgaaatggaa tatgttcgcc ctacggttga aaaagatcct  35100
ggaatgtttg gtttccatta caattctttt aattttgata aagtttatga attggacgga  35160
aagaccattt cggatattat tgattccggt aaaaagatcg tgtatatcga aatatccggt  35220
cgtgaatgta ttcatgatat acatggatca gttttacgag agagaacggc gggtaattta  35280
cgggaagcca tggagaggac tatatttggt cagaatgaaa atatgttcgg tctgctgggc  35340
gctcatccga cgatcgttct tgcgcgtcgt aaatctgttc cgatgatgaa gaaattccca  35400
gaagtattca tccccattga cgcagtgttt gatatgttgc ttgagcatta taaagatgaa  35460
tttcaggcgc ttgaatctaa gaaactcctg aaacttcgca agggcataaa catcatgtct  35520
catcgcattg attatggtgc caagctgttg attgattccc atggaaaagt tacggatggc  35580
tatgcccatc atcaacatag ggcaaaggca atcatcggtt atgcgaaaca acaaatcact  35640
gaagaagaat ggaagattgt tcgtatgctg gccaaacgaa acccgtctgg atcggggtac  35700
ggttatttcc gcaaggctgt tgaggaatta cattatcgta tagaaatgcc tttctcaact  35760
acgagatttt tccgcgcctg taaccagtta actcaagttg ttgatttatt gaatgaaaaa  35820
ttaactgctg aaggatttga tgagataaag gtcactagca ctatatctca aaagcaaaag  35880
gccaaaaacc gataccgagt tgaatgtcat cgtttggtga aattcatgat gtcaacatat  35940
cagccttcgg cacacaacgc gattgaagat gccactagat ttgtgaaggc tatttcaaaa  36000
cgtattctcg ggcataata gccccattac cccacagtga gaactacaag atgaatgcta  36060
tagaaaaacg tattctcaag ctgttgaatg agaacagaag tcaaagttca atagccagtg  36120
aattgggcgt accgcgctca atgatacaac gcgtgtcgga taaagaactg ggagtggatc  36180
cagcttcgat taagtctctg accactgaac agattcaaga aatacaaacc aagagcagca  36240
aaggtgaaag caattcttct ctggcatcag tttatggcgt cagtgccaaa acaattgccc  36300
gcgccctgat ggttcgtatc atcaaagaat ctaataacgt ggtcgtgatt tcgccaatta  36360
aagaattgac tgaagaaggg aaaatccccg acacctatga agttctggaa ggttcggtgt  36420
ctgtcgattc tgaaggcgaa gaatggtatg ttggccgttt cctggaaaac caaacagtgt  36480
ttatctgtat gcgttacgat agctctgctg ctattcaggc caaacttttc agaagcgaag  36540
aactgaaacc gttagaaact cggtcaagcc gcttcaatga agaaaatatt tcgccgttgg  36600
ccgaattggc gacagcactg gttgatggcg ttaccaaagt caatgatggc gtggtaatca  36660
gtgtacaaca tgacggcgaa acatacccga tgcgcggttc ccttgatgcc cgtcggcgcg  36720
tgggttactt tgatgtaatt ttaggccgta cgcttcgtct ggcgttgtcg tctgttgttt  36780
```

```
tctcggttaa gacaacggct gttgagaaag agtctggcga caaacaaact caaaactcat  36840
ttaacgaaaa agatctgtcg gtgttcttga atgagcacca gatcatgatt ttaccggaaa  36900
gcatcgttat cgtaatggat ggtaaaccgg aaacgataac cacaagccat caggcgtatg  36960
accgtattgt tgaagcgatt aaaaatcgtg acgtcaaaac agcgtacact ctgatgaaac  37020
cgcgtgaagc catcaaacaa ttcaccacag gcatggttga cctttcagac aatcgtgttc  37080
gctggggtgg ctatgatatc accggaactt ccgttgccaa acgcattttg gctttggcat  37140
taaaaggcga ttatccgaac ttggaacgct tgggtcgttt cctggacaaa atgttccaaa  37200
acccgagcgc cgcgctggtt cagtccggtc gaatctatga attcatggca tattcggata  37260
tcgaaattca tgaagacggt gatatcgtcc tgtataaatc cgttcgcggt aactacatgg  37320
acaagcgcac aggaaaagtt agtaatgctc ctggcaccat tgttcgaatg gctcgctcat  37380
ttgtgaacga taacaacaaa gatctgtgct cttacggtct tcacgtttgt tctctggctt  37440
atctgaaaca atgttttggt agcctgggac aacgcgttgt ccgttgcaaa ctgaacccga  37500
aagatatcgt gtctatcact gatgattatg gctccagtaa aatccgctgc tgtgaatatc  37560
tggtattaga cgattacacc acggaataca accgccaaca taaatctatt gatgttgacg  37620
gtctatacaa gtaaccgcga actgacataa aagagggggc ttcggcctcc ttttctttga  37680
ggttgatatg gaaaccagag atgtttactt cgtgtatgag caacaggcat ttggatcact  37740
gcgccgaaaa acaaagttcc ttgttgattc attccaattt gagggtgaac tcagagaata  37800
ctcgttcagg aattttcctc ctagagaagt cataggcgac cagttcgtga aattattttg  37860
tcgttgtggc ggctgtgact ttaacgacga cggatattcc atgcatgttt attgctgcaa  37920
ttgttgtggt aaatatatta cagtctatag gagaactgat catggcgaag acacaaaaga  37980
aaattgaaaa cacccaaacc attcaagaaa tcactgcaca ggaagaaaat aaacttccca  38040
gttatctgca acgcgtggtg gataacgtgc ctcagggtgg cgacggcggt attgtctacg  38100
ctggtgacta cggttgggtg tgtgaatata aagacggctc taaggagctt ctagaggaac  38160
tcaccggact tgccggaact ttgcgccgtt acgggttaga taaattcggt aagccgatga  38220
aaccaggtac tgtggtatca accgatatta cagttgaagt tcttcttttg cttgatatca  38280
atgatcttaa aacgcttgcg gaacccctgg gtatcgacgc gactgaccgt aatgaaataa  38340
tctcgcaatt gactgaaaaa ctgcagatta aataatccca gtgtataact gctgattata  38400
attcaatatg gctatcgttg acgaaagcaa tttgatggag tacgctctaa gacattatat  38460
cacccctggt gtctcaagag atgatttgat ggtagacatt cagcgaattt cgctaattaa  38520
tcaatcattg aaaagatttg tgccagggaa aagtcctcgc gtacttatca atcaattgat  38580
tattcttttc aatacctttg aaaccgaagc cgtgtgccga atgttggtgt tgaaaacgga  38640
taagaaccaa catcctcgtc ttaaagcagc gctgttgacg ttaggagttt ggcgagatga  38700
tttatgttcc ggttcatacg aaccagataa cgagctgatg atggctctga acaacgattt  38760
ggatgagtgg aggaaaccat gccaacaatc acagtattag tcgcgccgga agttgtccgc  38820
aacaaaccgg aaaccgaacg caatcatgtc gtgacgggtg ttgcaaaggg ttggcaaaag  38880
accagcctca accaagatcc tgatgagatc ctgaccgaat gtaaaggtct tgacgctctg  38940
ctcaccaaga gcaatttaca agcggacggt gtcaccaaag tggatcccac caagcctatc  39000
ggctttcaag tatcttatga aatccacgat ccgaatgcta ttttaaccac cggacttgtg  39060
attactccag ctacagccag cggagagatc ggacaatttg ttgaattgct agcgacggta  39120
tcccctgcca atgccacata ccaaggcgtt aattggtatt ctggtgatat tacgaaagct  39180
```

```
gtacatgtcg gtggtggtaa attcaaattg ctggcttcag gaactgtaac ggtttatggt  39240
gtcacggttg aagggaatca cacagattct acggttatta cagttgcagg cgctctgtct  39300
ttgtctactg atttacctgc caccaaagac gtaacttccg gacaagacgg aacctttagt  39360
gttgttgctg cgggtggtac aactccatac acttatgtgt ggcatttctc tgatactcct  39420
gggggtgcgg ggtcagttat cgatgctggc actaatgcca ccgccgccac tgctaacctg  39480
gttatcacag cagttgaagc cgcaaatgaa ggcgaatatt ggtgtgtggt ttctgatgca  39540
gatggccatt ctgtcacgtc tactcgttgt gaaatggctg tggtgtaatt tatgaagagc  39600
ttccaggatt tccttgaaga ctcttctgct ccggcaacca cgaccgccga tgtggggaaa  39660
cccgaaggcg gtatggttaa ggagcctgtc aaaaaaccaa aagatcttga agaagagtct  39720
gattttaaaa agatctttgg caacattttc aaagatttgg atttatccaa ggcgcgaaaa  39780
tggaatttca ggacaggcca atacgacgat taaagaggct tcggcctctt tttcatttcc  39840
agcattgggt gtataatgga cccgttcccc atgagcggaa cctaactgag gatataccaa  39900
atgcaatcta tgatcaaacg taaaatagaa atctccatga atgcccatgt cgatatgatc  39960
caacagcttg tggcagatgc gtatgagata caaaaggaac gtcaaattag gggagtgata  40020
gaccctattt gctccggcaa catgctctac tacagaatgc tccgccagac cggacataca  40080
gccgctctga agaaactact ttctaaaaag tttcaggtcg aaaacgacgc atatgtgttt  40140
ggcgtcttcc atacttctcg tgaacgtgat gcattcttct atccttcccg caaccctcag  40200
acgggcgaag aattacttat ccctgatgtc gataagaaag agagcacgac gacaatcacc  40260
catttcatgg ggaccaggat cgataaggct aacataatcg tgttctctga cactctacat  40320
gatgtaaaac gtttagccgc tgcccgtgaa atgttgcagg atgctcggac cagtctcaca  40380
aatttgactt tagtagtgtt tctgggctag atatctgtgt ggggagagaa ctccccattt  40440
tgaatcggag gtgatttatg ttacgttgca agagaggttc caactccttt aagttgggca  40500
tgctgactgg agtaacgttc atgattgctt tagacagcct tgtgggactg ctttcccttc  40560
ctgattttag gatggaacga ttcatattgt tagttctatt tggcggcgtc tcggttatta  40620
gtgctttgaa agcgtacaaa aagatctgat ttaactcaca cacagcaatt ttgatttgag  40680
accctatatc atgctcccat tactcaatgt tccaaaagaa cgtatgacgc cggatagtga  40740
aggcaagacc cattacaaca tatacagtcg aagccgcaca gaactaggca gattcctttc  40800
ccatttgca taccatccca tggatactgt tgatggtaat ttcaactcaa tagaaggcta  40860
ctggtattgg ctaaaatatc gccacgacga cttgcgtagt ctttatggga acgacgccaa  40920
gcaatttgga caaaccctgg ccaagtcacg catcgttgta ttgtcccctg atgatcccaa  40980
atttaaacga gacattatcg cagcgacgag tcaaaaattg ctgacaatgc catccaagtt  41040
gagattccaa ttggcccaca gccgtcttcc cctgattcac gcttatgaac atcaggggaa  41100
atacagtttt caaaactcta tggattttat catacagcat attaaccgct tccgtctaga  41160
aggatatttg aaatgaattt tctaaaaact atcttcaaca catcatatga actcagccag  41220
cgcgatccta atcgttctcc tgtgtttgta tattgcaaac tcgtggaaga gtcttgtgaa  41280
ctatcagatg tgctttatgg aatcgctgca tccgaacccc tgaacggtga agtggcggac  41340
gttatcatct cggctctgga tctattatat gttgtggatt atcaacaagt tcaacaacat  41400
gggtctatga ccaaagaaga aatctttgac tccatggtgt ttgctttggc tacggccaat  41460
cacacaactg atctcagcca acatacgttg gaggattatt ggttctgcag tggtgttgaa  41520
```

```
actatagaca aatatcttgc gatggttaat cattacaaag gccgcatcac tcgtttactg  41580
aaccaacctc aacgttcaga agataatatg gtggacctgg tttcaaatct gatacgcaat  41640
actgccaaat tggcgtgtgg gtataatcaa aaccatatca acacgatcgt taaagtagaa  41700
catgccatag aacacaaagt tgaaaagtgg cgtggtaaat ttggtctata agccaacccc  41760
atacataatc ttgtgtgttt accattgacg ggataggccg atgtccaaca aaattgatat  41820
tgaacgcaaa tacaaaaagc tcactcacat agagcatatc ctacttcgcc cagagcgtca  41880
tctgggcagt atccgttcgt ctgtggggac ggtgtgggtg tatgacccaa ccaaagacaa  41940
agtcatcttc cgtgacaact ttgagtactc ccctgcgctg atcaaacagt ttgatgaaat  42000
catcaccaac tgtgttgacc acagcaagac ccctgagggt aaaggcttga cggaaatcac  42060
cgtcacggtc tcccctatga acggtcaaat catcgtttct gacaacgggg gtatccctgt  42120
ggtcaagcat ggcgtcacca atgagtggct ccctgagatg ttgtttggct cgctctatgc  42180
gggcagcaac ttcaacgatg aggacgagga gtacaacaac cagaagtccg gcggccagaa  42240
cggtgaaggg gcttcgctcg tcaacgtgtt ctcaaagtgg ttccgcgttg ctaccagtga  42300
cggcaagaag tcttatactc agctgtttga agacaacatg agcaagaagt ccaatccggt  42360
catcggcaat acaccgaaag agttcggcac cactattgcc tggatccctg attatgcgcg  42420
cctgggtgtt aaggggcttg accagaacaa cctgctcatg atttaccgtc gtgcattcga  42480
agtggcggca tgcaacccgc gcctgaaggt tgttctcaac ggcaagcaaa tccgcattga  42540
tcgctttggt cacttcgttg attacttcta cgctggctcg gctgttgatg aaacggatga  42600
ttggtctgtt gctatcactc cctcatctgg tgtgttcatg catgcgtcat acgtgaactc  42660
aatcgccacg cacatcggtg gacctcacgt tgattatgtt gctgaccaga tcgtggcggc  42720
gatacgccct cagctggtta agaagttcaa gaccgaactg aagccagcga tgatcaagaa  42780
ccacatgtca ttgttcatcg ccgccgacat caacaaccct cgatttgaca gccagaccaa  42840
ggagcgcatg acgactcctg tgagccagtt tggtacgtcc tacaagccca gcgataaact  42900
gattcgcaag gcgcttgagt tcgtgacagc agggctgagt aaagaactgg cttcattacg  42960
caatgaacaa gaagatgccg aatttgaaaa ggcgaagaag gatatcagca aacgggatta  43020
tcgtgagatt gaaaagtatt atccggcgac cgccagaggc gaccgcagtg ggtgttcgct  43080
gctactgaca gaaggtgata gcgcatccaa ccctatcctg aacgctcgtg ataccaagaa  43140
aattggtttg ttcccgcttc gtggtaagtt catcaactgc ttgaacgccc cgcgctcaaa  43200
agtgatggcg aacgaagaat tcaagaattt atgcaccatt cacggcggtg ctgtgccagg  43260
ccagccgctt gatatcagtc gctatccaca gaccgtcgtg gcaacagacg cggatgacga  43320
cggcattcat atccgtgggt tgttaataac tctgtattgt acgttctggc ctgaatacgt  43380
tcgtcagggt aggctgaagc tccttcgtac tccatacatg cgcgtgtggt gtggtaatat  43440
aatgcacgaa ttcatgaaca atgccgaata tgaggagttc ctgaagacac ctgacgccaa  43500
gaagataacg aagaagaaat atctgaaagg tcttggcggt aacagcactg aagacttcaa  43560
gcgtattcta aacaacctgg atgcgtatac tacgacggtc acgctggacg atggatacaa  43620
gcagtcactg aagaatggtt tcggtgatga ggctgctgat taccgcaaaa cctggtttag  43680
cgatgtttgc ctatttgaaa ccgaggatga ataagatggt tgctaaaagt attaccgtaa  43740
cagaatttat caacggggat cataaagagt tttccgtggt taacagcatc cgtcaaatcc  43800
ctcagctgat tgacagcctg aagccaagcc agcgcaagat actctttgct gctcttgaat  43860
acaacaagga ggagattgtt gaccgccttg gcatgttcgc cgccgctcgc acgaattaca  43920
```

```
aatccggtgg tgagaacatg agcggtacga tcgtgaacat ggctcagggg ttcccaggta  43980
cgaataacat cccatacttt gaccgcgacg gacagtttgg ttcaatcatg gggcgcgaag  44040
cgtcttccgc tcgttatatt tcagtggcag tgtctgaagt tatccgtaaa atcttccgaa  44100
aggaggacga tgggatattg gaatacaatt atcttgggga agagaaactg gagccgaaat  44160
tctttttacc catcctgccc atgtttctcg tgaatggtat aaatggtatc ggctcgggtt  44220
atgccaccga caccccatgt cactgcgtta agtccgtgct cagtgccctg agagcacttc  44280
tccgtggcga agacccgaag gacttaaaac cgtactggaa tggtttcaaa ggagagacag  44340
gctatactga ggaaggaaga gcatacagtc gtggtttgtt cacccgcgtc aatgcaacca  44400
ctctgaacat caccgaggtt cctattggtt ggttctctaa aacctatgag accaaagtgt  44460
tgttgccgtt gtacaaatcc ggcatactca ctgaatatgc taacgatacg accgaagatg  44520
gttgggatat tactgttgta ttcaagcggg gtgaattgtc taagttgaat gacgaacagg  44580
ttgaacaaat gttccgtctc tactcagcta ataagcccgt gtggacagct tgggatgaag  44640
atggtgttat tcaccgttat gatggttgga aagatatgtt gcttccattt ttcaattatc  44700
gcctgagtcg ctatgaagat agacgtcagt atcttatcaa ggaattgacc gacaaaatac  44760
accgtttgaa caatcgtgcc atattcattg ggtgggctgt cgttacagat atgcgccgga  44820
gcctcacgga actgaaagcg ttattccaga cagactatcc tgattttgat ggcgatctcg  44880
atgatttatt caagatgtct ttatcatcaa ttacactaga tgcccgtgaa cgtttgttga  44940
accagataaa gaatttagaa gttcaacgag aagaattaaa taataagcaa gacatcgatc  45000
tttatactga agatttagat gatcttgaaa aggcattggg cctataaatc cggagggtga  45060
attccctcca aacaagcaag ggttcacca tgtttgtata tttccgcagt ctctcattgc  45120
tgactttctt ctattggttg ttcgatatct tatgccctcg ttttattaaa gaggaagttg  45180
cttttgtcaa tcatgaaggc caacaagatt tatggatacc tctttgcgct ctttctgatg  45240
taaccgaatc ggatgaagtg ggtatggttg gcaccatgcg ttcatttaat ttatttggat  45300
tcgcattatt ccctaagtta attggagaat tacacccata caatcctgat gaagaagtgg  45360
aggcgtgata tgtcaaaatt attgactcca aaattattat caatgggtgg ttccatatat  45420
tttcattgtc ctggatgtaa tatgcttcat ccttatcgca tttcagggca aatgcctggc  45480
ccaatatggc aatggaatca cgatctcgaa tcaccgactt tcactcctag tctgttggtg  45540
aatcattctg atccggcgag tcgttgtcat ttgttcttga ctgatggtaa attacaattc  45600
cttggagatt gtttccacga attaaagaat caaaccgtgg agatggtcga tattcctgaa  45660
cctgaaatat ggatagatta gattatgaaa ttacttggat attttcgttc tttgcctact  45720
ggatctccta atgggtgtca attatactct gaagtgaaag gggacgtgaa cgacactcac  45780
atcgccttgt atgctcgtga tatacctgac ccaaccaagt ttgatcggcg tgttgtggct  45840
gctgccaaca aatatggtga tgtgatcgtt gtaagcgccc gacatcacga caaattgatg  45900
aacacgcaac tcaaacgatt gaaggaagca ggtattatcg aaaccaccca cactcgtgaa  45960
caagggttta ttgataacta tgggcaatgg atgtcccgtg aagaggccgc tgtggtcgct  46020
cgtgaagccg gacaaactaa tcaggtccgt ttgaagaaca ctcctttcaa agaactcttt  46080
tccgaagacc tctattgaat aaattggcgg tataattgcc gcctaacccc ataatgagac  46140
aaataacatg gcaaatgaaa ttggtgatat tgcccagttc cgtgctattt cacgccgcct  46200
gaaatcgtat ggactcgtca tcgaagaaat agatgaagat gttcagggtg tattggaagg  46260
```

```
gatgtttggg agtaccgttg gaacggaatt atttgaactt ttaaagatgg cagctgataa  46320
ccaattcgtt gaatatattt ccgaacacgc tattgatggt ctgaataaat gaacgagtta  46380
tatgaatttg aacgcgtgta tgagtccgct tcagtttcag gatacatgaa acgattatat  46440
caagaaatct gtgttcgttt gataatgcga ggaatatctg tcaattgtgt tatggcacag  46500
acagacagtt ttattatgac actcactgac catcgccaga atatgtgtat catccaggtt  46560
agctgtgtca acaacgaaat tatacaatgg agacgttacg catgaccaca tatgttatca  46620
caaacggcga tttactgaaa gccgctacga gttttaatct catcaatgct ttcgctcatg  46680
gcgcaaattg ttggtctgtg atgggcgcag gtatcgccaa ccatgttcga ttagatttcc  46740
cagaaattta ccgagccgac caattagatg aacgtggtcc ggaacaacgt ttggggaaca  46800
tgtcctatgc gtttgatcat gacactggtg tctggggatt caatttgtac actcagttct  46860
accctggtcc taacgcacgc atgccttcca ttatcagttc agttcagatt atgtttgaac  46920
aagttcacga tatcattgag gcaaaaactg acgaaacagt ctatgttggt ttacccgcca  46980
tcggctgtgg catcggtgga ttgaaactgt ttcatgtggt gagccagatt aataaaatcg  47040
cggatactat cttcgaagat accaggcgtc gtgtcgtacc cgtcttttat atccgacagg  47100
gtgacgggtt tgaacaagat ttacaagaac tttcccagat ggtagactac ggaatctctg  47160
tcgtcgctag tgaagaagat atcatcgaag aggaaggtat tggatgaagc gtgaaataac  47220
agaagagatg ctcgccaaag ccgttcttca tcccaaggtg cgttttgcat ttatccctac  47280
acgtttacac gatggaaatt gggtatggct ggagcattat gttcgcgctc ctatcggcct  47340
atatgcccaa ctccgttatg gcggcgaagt cgagttgaaa caatatcgcg tcggcggggg  47400
attaggcggg ttggatgacg gggaatattt cccacatcga aatttcgcca tgaacgataa  47460
ttcatatttc aaagtcgagt atgccgccgc ttgtgggaca tatcctttga aactcctttt  47520
agagaaagca ggggaaactg atgtataaat ctaatttctt ggccgtcgct gatagcgaaa  47580
ctctcggtcg ttgggatgat gctgtcatgt tgtcttgggc acagactatc gccgacctga  47640
caaagcgtta tactcttcag cagcttgttg tagagcgcac gacatttatc aaactgaatg  47700
tcaaagaaca gattgaactt ggccgtgtga aagaccaggg cactgtggaa tggtggctgg  47760
gtacaggtaa acgcaacccg tgcgacgccg cccgagctat cagtctatat ccgaccgaca  47820
aggatatttc tattttcaaa ttggccgatg aaattcgcag ggatgccat cgccttggga  47880
tcgacccgcg atcggttgac tggtgtgata ggaatctgtt tgacctacgc aaggctcagc  47940
acatcattga ggtgacgtgt aagcaagatt ccaacgaacc ttgggactat caccacacat  48000
ttgacatcgt aagctggctg aagggtgttg ggcagcagga tcgatatgct ggtatcaagg  48060
cgtgggaact ggaaggcatg gtctatcatg atcctcgtta tgatgcggcg cttgactggc  48120
tacgcattca gaaaaccatg gaagacctga tggggctgaa ggtagaagga tgattctttc  48180
cttgttttca tggttgttta caatcatagt tttcttcata gtctgtgttc aatattttgg  48240
aggttcttaa atgttctttc aaattgtcgg ggtgatcacg accattgttt ttgttaccat  48300
aacgctttgg atattgtatt cttcatttat ccatccgatt tttcaggctc tcagtattac  48360
acgttggctc acagcgtgtt ctttgaaatc cggaagcgaa tgtccttctt tatcgtccaa  48420
atggaaattc ttcaaatggg cgtatgaagt cggaggagtc cgaacaacca gatattcaaa  48480
taatgtgggg gaatggttta gcatcggcaa ttggcgtttg tacgaatctg aagacaaata  48540
agccccttc ggggcttttc tatttgtata atgtattatc attgtaccat catatcttta  48600
tggcgcacaa caaatgattc tttaagagga atattttaat ggaaattgtt gtctcagtat  48660
```

ctgattgtga ttttgtatac cgtgttcttc aaggggatgc tccattgccg gagaataatc 48720
aagaagtgac gttgttctgg tctggtgggg tggatagcac atacatgttg atttggttgt 48780
tatcgaaagg atattcagtt catactgtgt attgccacct cgaaaataat aaatttaaat 48840
ctaagcgcga aaattgggcg aggaataaaa tacacaactg gattaataaa aatgccccac 48900
ttctcatgta tcgttggaca catcatcaag aacctatcag tagcatcaac gtcccgaacg 48960
gtggttttcg cgcttgttta gcacaagccc cgatatggtt attaaacacg caatttaaag 49020
gcattggctt gccgtccacg tatatattgg catatgttaa cggcgatgac gcaatacact 49080
ggatacccgc ctttaataaa gttattgaag gatacaacat gatgaccaga gacggggaaa 49140
gacctattga aattttatat ccattgatta gtctcaagaa atcttggttc tatcatcaca 49200
tgtccccaat acatgactta atgacatggt gtgaattgcc aattttgaaa aagaattgtg 49260
attgtcctgc gtgtgttcga catcgccatg agttatcata gagatgaaac gttcagttgt 49320
tgtaaatgac atcacgagat tgataaatct tatcaaagac gtcttcccac aacaggtgga 49380
tgttgagtat gttgggaaga acggaaagtg ctatcaggtt gctctggttc tgaagcatgt 49440
gtatcctcaa gcagagatcc attacagtca gatcgaaggt catgtataca ctctgattga 49500
tgggaattat tatgacatcg aaggcattca cttcagtgtt ccccccgata cgtgcttatt 49560
ggaacataac agaggccaca aaccgcatcg ctggcataaa gggtttgtga acgtaccgat 49620
tttagaatgg ctgaggaaac cataatggcg ggaatcgtaa agtaccttgg tgacactcac 49680
cttgggcata agaaggtctt taaaccgcgt ggatttgata cacaggaagc ccatgacgct 49740
gcggtcattg acacgatctt ccaaggattg aagtctcggg acgtccttga actggctggt 49800
gatatatgct tcatcggggc tgaagggttc attcgcctga tgcgggaggg tgccaagcga 49860
aacattgatg agttcaaacg ccgccccgtc cccgatgact ggcgtccgaa ctttatcatc 49920
agggtggcac aaggcaacca tgacagcttt aagatgttgt tgtctctgta tctggacggc 49980
tggattagct ccttcggcgc tatgtatgaa cgtgacacgc ctgttggccg tgtgttgaca 50040
acacatgttc cttatcaatt agaccgttgg gcgtataaata tccatggtca tcttcacgaa 50100
aatattcgcg aagagcgcga atacctgaac tgcagttggg aacaattcaa gcgtcctgta 50160
accctggctg agttattata cacaaattta ggaattgtgt tatgagaata ttctttcctg 50220
gtcagaaagt acccgaagaa atacaaaagg tcgagttatt tggttataaa agcggtgatc 50280
cgttcctgcg attttcttca ccatgtatcg tgaagcgcaa tcatgaaggg cattatgtgc 50340
gcccaatcat cctcatgggt tctgtcatga cgctgagagc caaaacagac tccgtcgtta 50400
ttaccggaag tcccaacata cccaatggaa agactacgct aaattgcaag cccatcctgt 50460
cgtcttgggt gttaattgga tttctgtcta taatcttgtt ttatcgttac cttactgact 50520
tggggatctt atgaaaaagc cacgcatcac aggacatcaa ctctgcgtcc ttttaggaat 50580
gttgaatttt gaaaaaggtg aagctagacg cctttgtcat tggtatttca atcccaaatc 50640
ttggacgaac gataaaggga aaacggtttg gacttttcat gcgccaccga tatctggcgg 50700
gtttcgttct gtaaagggtg atccatggga tacgcgttca ggtcaatcct tgttgtctaa 50760
aggtctgata gaacctgcgt ttacaatggt tcatgacaac tctgaagagt ataagcattg 50820
gccgaagtct gaagtaacat tctataggct tacagacctc ggtaaagcat gtactgaata 50880
atattttagg ttattgaaga aaggggaagg tatacttccc cttaatttat tgggagagac 50940
aaacatgatt tcattaaaag aaatgtacga acgcctcgaa gaactgaaat ctaaagaacg 51000

```
tctgtattca gaagagaatg cagaaatgtc agatcttatc gaaaaaattg cgttgcgtga  51060
aaagtatctt caacgttata tcaatcaccc acctcacatt gttgaacgtg tgaacgttga  51120
actggaaaaa ctgtccccaa tcacgtatga caaattgggt atggataaag tccacacggc  51180
tatctctggt gttgtgaact ctatgttggc gttgggacaa gtatttggtc gccaggacca  51240
tgatgatctt attttctaca ttgagaaaaa tgtggtggtc aaatgaaacg ttatcgcctg  51300
aagtttgagt taactcgaag ggaagacaac gaactcatat atggggaaat tttcatatat  51360
gatccttatg atacggaata cactgaatgg ctgaagataa tattggctgg tgaagtcgat  51420
aaagtatacc gtgccattga aaaggacgcc aaaggggtat taagttttgg tcatcttcga  51480
gtcgcggcca tgattggttc agctttagaa atagtgtctg aagcgatagc catagatcta  51540
ccaggggaac atatcttcat ccgtgaatct aaagttgata tggcaacgaa ttatgtgatg  51600
aaattgacct tgacagaaaa tatggaaaat aacaaaccaa gcattttccg ccgtttcatg  51660
aacaaattaa agggtgttaa aaatgattaa accacgtatg atgttcgccc atatgcgatc  51720
agctgcagca tatggtgtaa ccagttatgc tcggcgtctg caagtcggtt gtgttatcgt  51780
aaaccctgaa actgatcagc ctgtggctat cggatggaac ggaacgcctc ctggtatgcc  51840
gaatgtttgt gagatggaac aacacgggca aattgttaca aacccgtgtg tcattcatgc  51900
ggaggaaaat gctctaatgc gtatccccga aaatgcagat gatttcacag ggttggttat  51960
gtttgtgaca catagcccat gccctgattg cactcagaag atcatcgaca acggcaagat  52020
cgataaagta tattatcaag agccatatcg tatcatggat ggaatcaaaa aattgatgaa  52080
cgctggaatt gaagtttatc ggatggtaga cgatatggcg atccttaaac acgttttcga  52140
cgatcaaggc gaagtcggat acgaacaaat cttatccaac ccagacaaag taaggaatta  52200
aaatgcgtta tgtagaccgc atgctcggcg aaaatgaaca tgtcatcgct ttcacccgcc  52260
cgacttggtg gagcggtttt tggatttatg ttctggttat tttaacgatt atcccaacat  52320
ttggattcag cttgttattt ctgataccaa caattttaaa tgtattgaca actgaattcg  52380
cagtcaccaa caagcgtgtt attgtcaaac ggggatttat tcgtcgtgat gctgatgaac  52440
ttcgtcttgg taaagtagaa accattaagg tggaccagtc tattacaggc cgtatcctga  52500
agttttcgac cattagtgtt attggtacgg gcggtactcg cctgttggct acaggttgtg  52560
ctaaagggaa cgaattccgt caaaaaattt atgatcatct gggtgactaa atgattactg  52620
caggatacac cgtcgatttg tattgtgagt gtgttgaatg caaatcttgt aattgggctt  52680
gggaagaaca tcaccccaga tgtgggatga agtcttatgc tggtgaatct tggggagact  52740
gtgctagaca agcccgtgct gatgggtgga tgatatgcag ggacaaacaa acttgctttg  52800
cccctggaca tccaaggaaa tcagggtaat aacaaaccat catcttccga ttgcgttggt  52860
tgtttattag cagtttcctt cttcatttgc tctttcaacg cattaatcct ttgagcgcgg  52920
cgtcgatctt ccatttcgac ttcgcgcttt ttcttagaac gaagagcaaa ttgtttttta  52980
acttctgggt cttcacctgg caccaaatgt tcttctgtcc agataatgaa tttccaacct  53040
acctttgcgc aatgttcttt agttgctgtc cactttgcct gatttaccaa ccaagtgcgc  53100
attgaattat tgaatgttga ttccttcatc gttttagttt tgcgaggttc tttaatctgg  53160
tctttgggtt ttatttcaat aagagtaatt tgtaattcat cggaatcctg ccgacgagtc  53220
caaaccttca aatccatgaa ataacgatgg gcgcggccat caaccggaga tatgtaaggg  53280
attacagttt cttcgttttc ccaaaaaatg atggcgggat tcatatcaca aaatttaaag  53340
gcgacaagtt ctagcgaaga acgaaatact attttgttca cgtcgccttt atatttcttg  53400
```

```
ggatttacgg gaacatactt cccctgcaaa tacatagcca tattctagtc ctaaatagtg  53460
tcatcactct attctaatta aagggcttca gaccatggcg aatttcaagt cgaccatcga  53520
taagatcaaa gttctgaaca caaaaggctt ggccaagtct cagaagcaat tggtctatcc  53580
attagacata acaggggggta aaaccctcgg ccattatgtt ctattcaaca tcaaccgaat  53640
atctggttct tcatatgggg acaccacaac ccaaaccgtc gaaaatccga tacaaaatcc  53700
attgggtaag actcctgtgg tttatggttc taaatcgggt tctattagca aatatgcttg  53760
ggcgcgtcac gtccgctcta acgaatcaat cgtgttgtgt atgcccgaat ccattacaac  53820
caactatggc gttggctgga acggctccga gttgggatta gcaggtatgg gtgcccaatt  53880
cttatcacgc gccgcccaag atatgagtca attcaaactt ggggatgctt tgaatgttgg  53940
gaaagaaatg gggagatttg cggcaacaaa ggccattcaa tctgcttcgg aagcaattcc  54000
tttcttgccg acaattaatg ctcatgatac attagaattg tttacaggta cgatgaccaa  54060
cccgtatgtg gagatgattt tccaaggggt gcgcaaccga gaaatcccgt tcacattcaa  54120
attcactcca agatcgcaaa aagaggcgaa aatggtgcgg gagattatcc gtttattcaa  54180
gatgcacatg tatccagaat acaaatacaa caagaattcc agcgcattct atcttcatcc  54240
atccacgttt gatatcacgt tcatggtcca gggagaacgc aacaaatggt tgcatcggat  54300
atcgacttgc gtcctatcaa atatgtttgt caacgagacg cctgactctt catatgctgt  54360
acacaaagat gacagcatcg tgtcgacaca aatcgacatg acgtttatag aactagaacc  54420
gttgcacaaa ggccgctttg ataccgaagg cgacagcttc taaggagaag atgccatgaa  54480
atattttgag aaatttccac tcgtgtggca tcaattaatt ggtgtcaaag aggatgacca  54540
agtcctgttg cagaacttaa cacgacgggt tatggttgtt aagaaaatta gggacataga  54600
agggcttctc ctgccgtata ctgtttttga tggggaaacc ccaaggtctt ttgccgaacg  54660
cgtctacggt tcctttgagc tgttttggat cccatgtctt atcaatggta tcatggacat  54720
cacagaggac tggccaaaac cagagcgccg tatcattgaa gaactgacgg ctcgatacgg  54780
ccttgacgga atgtgggatg tgaaatacta cgttgacgaa ttcggtcatg aaacagaccc  54840
tagagcaata cgtttagcat atggccttgg ttctatggat gattccacga ttatcgccaa  54900
ctatggtctg acaggtatta catatcatga tgatgctata aacaaaaacg aagccaaacg  54960
gaatattcag gttctagacc cagattatgt ttcttccttt gttaatcagc tggaacagga  55020
gctgaccaaa tgatcgaaaa taaagaatcc caggacggaa ttttaactcc gtccacaaca  55080
tttgatttga aatatatggc gatattaccg cacacacctg aaggcggtac tcccaagcct  55140
tatgaccttt catcgttgtt tcaagaattc aacgtatatc aggatcttgg tctggaaggg  55200
aatgcttcac cgtcgctgac agctaatatt ctgatcaaag aaggctggga tatattggat  55260
acaatgccaa tcctcggagg tgaggaagta gtggtatcgt tcaaatcacc tgcggcttcc  55320
gactacacta cgctttcatt gcgagtcagt cgggtgggga gagttgctga cgaatcgaac  55380
tcttcttcga aaaaggcatt ctggttgcac ttggtgacaa cagacgcgta tcgagatagc  55440
atgttgcgta aatctgttgg attaagcggt tcttattctg agatggcagc taaaatcttt  55500
gagcaactga attcacgcac caaatttgaa gacatagatc cttcatatgg gatacaagaa  55560
aggttcgcta cccctctttg gcctgtactc cgctccatag attatatggc cagccgtgca  55620
tatgacgaat tattcatgcc attcgttttc tatgaagact ttacgggtta tcacttcaaa  55680
agcatgacga cgttgttcaa ccagggcaac cagtctatga ctgctgaaga gaagcaagag  55740
```

gcttctattg aaaagaaatt cttccgagac cctcaagacg cgccgttgat gcaggataac 55800
aatttcaact cagaacgttt catgcggact ataatcaagg ctgaaaagaa actggcgcgt 55860
gatcaataca tggcgaatta tcgggatatc ttggcagtga acgagcgcgt gtatgacttt 55920
agtacaaaat ccacgacagc gacccaacgc atttattcag aatggtttga cagcactgct 55980
caccttgatc ctttcccttt gttctctgat caattcgacc gcgagaacgt taggtacatt 56040
gaagcgcaac cggatggtgc cgaacaaata gattacgcac gacgcgttat agaattcagc 56100
ctcgcgtcaa cggttatgcg tttgctggtc gtgggggata accgtctgaa tgttgggcag 56160
gtttattata ttgaagattt gtcgaaccgc ccgaaatcta atgaaaacat tgccgagtta 56220
agtaagttat caacaggcca ttatatcgtc acaaagatac gccataagat ttcacgcctg 56280
acaaatgatt atcaatgcgt cgccgagatt gccaaagata gtatgatcca gaaggtctta 56340
ccgcctcaga ctggtcaaac tgtggcttct acaccaactc cgacgccaat agagaaagga 56400
caagcccaga aggtctgaga ggtgacaaat ggcagataac aatcaaccga caccagggca 56460
gcaagacatc gtcaaggttt tggataaaat caaaaaagaa atgatggagc gcaagcaatt 56520
gcgcgcccaa tccgagacga ataaacagct cgcagatgtc aacaaacaac tgcaatctct 56580
gaagacacgc caggcgtcta atcaggagca gaaagtcccg ccaattaaat tcccatcggt 56640
gaatgatatt gttggtgggt ttgtccgcgt cagtcctatt ttcacaaggg attacagcac 56700
ttggatgaaa gacaccgtca gtctttccaa ggacggaaat gaagaactga tgcgaatcgc 56760
aaccaaaata gaaaaatttg gcgaagcggc gaatggtccg gttgacgaca tgtcagttga 56820
atatcttgac atgatatcag atcaattggg cgcggccaac gaagatagtc ttgaacgcct 56880
tgatggatta aaggataagc tggcgttggt cggaggggag atcgtaaacc tgactgacat 56940
aatgcttcaa acgcataagg acacgctgga tttcaataaa gatgccagta acgaaactgt 57000
tacccgcctc gacagcattg atgacaaatt gggatacatg aacgaagatc ttaatgatac 57060
tctgacacgt atctatgaaa gtgatcaaaa atatagagaa gaagagaaat tccgtcgtgg 57120
cgaagaaggt aaggaaaaca agaacaaccc agaggctggt tctatccctc cgtctgagcc 57180
taaacaagat ggtcaatctt ctgggttagg cgcggcgctg gggggcactcc ttggactggg 57240
tgcgttaaaa ctcctgatgt ccccattaaa acttgttggt ggcttcatta aattattcat 57300
ggggtttggt gctgggatcg gcgggttgct tgcgcctctg aaagcagcaa ccaagatgct 57360
tcgagttgga cctctggcgt taataacatc tgtatttgaa ttcggtaaag gtttctttaa 57420
tgctaaagaa atccttggta aagcgcaagt atcgatcgtt gatcgggttc aggcagggat 57480
aacagagctg gtcggtagtt tcggggatct cgctgattgg gttgctgaaa tattcggatg 57540
gaacaatgct gggtttggaa aggcgttccg tgaacaagtg ctgaaaatga ccgaagcgcc 57600
cgtgcgttgg ttgaactcga ttgttgattg ggtcaccaac gatttgtttg cgggtatcgg 57660
gaagagtaca tcactgaccg aaatccctgg taaacttgca gacaacttac aaggccaatt 57720
gataaaattg gttgattggg taacgggcgg gatatcagga ttgattgatg atggcatggc 57780
ggctgcaaat aaagtcgttg aagatatgaa gaaaggattt gcggaaaacg tgaagaaacc 57840
attctttaat atgttgaatg ccataaccaa tgccatgttt gatatcgtgg ataaattcgt 57900
gagtatcata cctgatgctc tgggtggtga agcagccagg aacaaaatgg cggaagcaag 57960
acagtctatg ctaatcagcc aagacgataa ggctcctgag aatgcgtcta cgccgccaag 58020
cagccaatca ccagcacaac ccaatgccaa tatcagcacg ttaactccaa tgccttctgg 58080
ggtgtcctca gacgctgtca acgttacgga tagaacttca caattgaaag acgcatacgc 58140

```
agggattggg ggaggtactc tgggcggggc ttatccggtt caaggaagag cagccaataa  58200
catcgaagaa gttaaatccg cctatgctaa cccgccagcc agtgttgtgg ttccagtaca  58260
acaaaatgtg gacaactcga agaaagtcag tacgacgaac aacttcaata gttcacagtt  58320
ggagccgtcc aaccgtactg atacagggcg cattctctgg gattggtaat caaattccgt  58380
gggcaaggat tagctcacgg agttttcctt ttgtgtattc tgtgttttca tcaggaacaa  58440
ctgaattggt tttctttaat aaaaaagact cagagttcca atagatgtca tccttgagta  58500
ttgtatcata taaatggatg aaccccacta ctttattcaa tccaacgaga aaccaaattg  58560
gatagcgttt aacaataata tctgtcagta aaggtggatg cccattacca tttcctttga  58620
tatattggat aaaattcacg cctctttctt ttatctcagg gatcatatat ctctcaaaat  58680
gttcaagaaa attatatgag aagttgtcat acaggcggcg atattcatta taattttctt  58740
gagcctgacg ggtgagtaat gttgtcaccc atgtttttgg tgatttaaca aagttggcga  58800
tgatataatt ttccaccact tcaccctggg aagattcaaa ccgacgagca agtttggcaa  58860
attgtttggc cacaccctgt ttagaataga acgtttcaaa cttgtaattg ttcatcggcc  58920
catacaggcc ataatcaaaa tctttggtgg tgaaatgcaa cttgatcgcc atatatatgc  58980
aataaacgtt aaatgcacgt tcgtattgca ttttctccca ctcagttatc atggcgtttc  59040
tccctgcttt tctgtttctg taatctgcgg cgttcagaac agaactgatt gaactccgtc  59100
accaagcctt tctcctttat aaagagaatg gcgtttcgaa aagcaattcc aatcttggca  59160
tatgacggcg gatttttacc aaccacgtga tctctcctct gtgcgaacga aacgttgaaa  59220
ctcttctgtc ttcccttgtc ggtgaataaa aaccaacgcc agaataaaac gccgaaaaga  59280
ttttgggata agacgataac cgtttgtcca attatagaca acgtcagaac aattcatcat  59340
cttcatcatc tgtaattcag aaactcccaa ttccctcata atgtttatga gattaagaga  59400
atcattgtct ttccttggtt tcttatcaat aagtttcata ataacacctg gtaatgattt  59460
cttggaatta tactgctact gtctttattg aatggggttc cgaagaaccc cgattttcat  59520
gccgcttcca acaacaccaa aatattttcg atatatgctt tctggatagc atagacttca  59580
gccagtgtat tagcgacttt cttgtctgtg cgtacttcaa cgagacgtgg aaggaataga  59640
gacttcatgg cgtcatcggt tttatcctgt acgccattag agagcacggc ggcaatctta  59700
ccaatgaagt cctcttggtt ttcccacatt cgtagtctca actcatctga gatccccgat  59760
acgccaacaa ctaagaggct atcagaggtc ttgcagagga gagatccaaa tgtcttggcg  59820
tgcttccctt tcttatcggc ctcgttgaag ccaacgattt caaggtcaca ttctacttcc  59880
atttttagct ttaacccttc agatgatgtt ccatcttccc aaggcatatc tgcggcctta  59940
caaatcgtgc cttcttcccg acgagccaaa gcgtctttga agtgttcgac agcttcttca  60000
aatgaatgaa caacacgggt ttcttgaacc tgaaccagtc cgtcatcccc ttcgaacaac  60060
tgttgtatga tatcaaaacg gcgctcatat ggggtgtcca cacgctgagc attgaaccaa  60120
ttatcatacg gcacaacgtc ccatacccga tagatcacct tgtaacgatc ttccaggggt  60180
tcacccgttt ggataacact gttgagctta ccattgccga tagcccgagg caacactgta  60240
ttcgttttca gatcaatgac gagcagttca ccatggaaga cgctttcacc aatccccgca  60300
tcgtagatca ggtctttgaa aaccaatgat aggttatcaa cggaaccacc cgcaataaga  60360
gaaccggaac gagaacgaat ctctgggtct cttccataac gacagatgat gttggcaaac  60420
atgccatctg acttcagctg gctgaagacg ccgcgcttga agtccatctt cttcagcaag  60480
```

```
tcaatcgtca tgttatcata acggtgatat ggaaggatat taatcagacg ccctgtacca  60540
cctgctgcgt tgaatgctgc gtttatacct ttctcggcaa ttcccgcttt gatgtctctg  60600
tcgagtataa tttgtatcag ggtatggtaa tccggatgga tgttggtcgc ggccttcgca  60660
agttcttgat ctgccttcat cccaccgatc ttgcgttcgg ccatcatatc aagaacgtca  60720
taaacctgat cccagctacc aacaacgccg cgcgagagca tgcgagggaa tgcgtttaga  60780
ttgaattgag tgcggtaata agaacgcatt gggtcgtaga cgtattgaag gaaatcaacc  60840
aattctgggt tgtttctgaa cgcctcggtc agcacagctt tcttggcgtt ggtgcctttg  60900
gtatcgcgaa gattttgaat tatttctaaa agaggaagca tcatgtgtct ccagggttat  60960
tcgtcatgct attataaccc tagagacttc aatagattta tttgctgcgt ctttttctgt  61020
tgttcggtgg tgtggcagag gtgaaagatt ccttccaact cttgaatttt tcaatcaggg  61080
attctttccc catctcaccg ttggaaacat catggatata agcaaatgcg tcatacccat  61140
atcctggtaa agcagaacag attcgaaggt gaaccaaaga ttctcccaca gaaaccaaat  61200
aatgatcgcg acgatcattc agagcataat gattgtcatg gaatttgtcg ataacaacac  61260
agttctgggg ttcggcgtca attgccagcc cgttggcttc gctaccgccg cgcccaaggg  61320
tgtatcctgg gaataatgtt tctacaagtg tggtcatagt ctgatccttc tgtaaagttc  61380
ccatgcatta tatgggtaaa tcgtttattg aaaatcgtga tggccgtatg cgccctcttc  61440
ggcttcatcg cgttcagctt ctcttatctc agcctttgaa gccccaagga ctctgagctg  61500
gcgagaactg aacagaggat agtccattcc gtcgaatcgg atatgaccac aacccgcctt  61560
attgagtttg tccatctgct cttcagtgag gccagcagaa aggcggacag actctttccg  61620
caaatcagaa aggattgcct gcgccgattt aggtcgcttg ccattcaggg acaggtctgt  61680
tggggtatct ttacgacacc caaaggtctt ccagtaggcg gcgcaagact tagaacagaa  61740
caaccccag ccacggtcaa tgtcggcctg gcgaaccatc ttcttgttcg gacagcattt  61800
gcattggatt tcaacttttg acattgtgac accccagagc tttgcggact ttttcacggt  61860
catatgtatc gacctgaatt gcttcacgat taatccgacg cctgtgatgt cgggtgagcg  61920
ctttatacac ggccttggcc tcatggtatg gcagacaatc gaaacaaaaa ccgatatcga  61980
ctctataccc tgcgctgcta ttgactgtat atgcacatac ccttacgccg ttatagatga  62040
cagcatcgat accgacaaag cgttcaccat tccattcaac gtcatcagcg tcgatggcat  62100
caataagaca acggatttcg acgcttaggg gtttccccaa caaccagtta aaatatttgc  62160
gcatgtcatt tactcatcag tgaaagaaga ttgactttat ctgaacgtgc gtttggtgag  62220
taatgcacgt cctgagagtg cctcttacag cacggacaat ccttggtggc aattacacag  62280
ggagccttat ccacggcata tccggcttct tcggcttcct tcacggtgtt aaatggcaag  62340
tatgcacttg tgccttgccc tccgcatgaa cattccatta gaaatcctcc ttggtaatga  62400
agagcaaatc agatttcaga ttttggcgct tgacgcggcg gacatgtcga tgctcctttt  62460
taataccgtc tgaacgtttt gatttagagc ggcgattttt gtatgtgtcc gctgggtact  62520
tgtcatggcc tggacaacaa gatccagggt agtaaacatc caagatttcc cgtttcatta  62580
acgtttcctc ttaaatggga tgatcagggc tatgattaac agcatagctg tgatcactcc  62640
gcatgcgata agaccgaatg caaatgcttt caaaacaaat tgtaaaagaa tcataatttc  62700
ctcagttttg cccttgtaat ctgagtttgt ttaatacctt tgaattcggt caattctttg  62760
acacgacctc gaatgatcat atcgccttct aaaaactcgg tttccatata ggaagtcttc  62820
catgtaatgg tattgccttc cttggttttg aaagtataca gatacgtgtc accataatca  62880
```

```
gatgaataca ggaaaatcct tgcttcaaat ttgacctgtg cttctaacat ttcaccaact  62940
tcaccaaccc aatttgatac agtgcgcgtt tggcgggggg tgtggatata atcataatac  63000
tttgctgctc cccaacgaac tgttgttgag tctttaacaa ggtgataacc aggttcgcac  63060
atacgtttca gccggacgtt gaaatcgtta ttttcagaca acgatgcgat gaaaagcatc  63120
atatgataca tctctgattg agcatcttca cgggctttaa cagccttgtt atagaatatc  63180
tcaatgtcag aacctttttc cggacgagta ccgctagaga tatgaccaag aactcgacca  63240
aaatcatcac ttttaatgct caggccggac agcaaaacct gaaagcattt acacaaatat  63300
ccttctgtgt caacataatc tggttcatta acccgataaa ttccttctgg gtcatcttca  63360
tcgggggtaa acatttcgtg aatagacatg taataagaca taaccgcatc aagggatttc  63420
tgatgcggga cataatgatg catacagctg ctacccacga gcatctgtgc accagattgt  63480
tcgttacgaa cgacatatgt gttatgacga cgcacagatt tgttgcaatg ctcgcaccaa  63540
gatacgtttt cagcttcaaa tctttgaatg aaatttgggt ggatgtcatc tgacagttta  63600
ttcagaatga cttttggata ctggtggttg aattgtccaa tgatactcca cccaccataa  63660
gaaacggggc ggtcgatgcc ttcaccagtt agagtacaat cttgccacca acgataaaat  63720
ttttcgccag tgatagaatc gcggtgttgt gttttgtatg gttcgctgta ttcgacaaga  63780
gggaactcga gattcaggcg cttggccgtt ctttcaagtt tggccagacg ttccttgaca  63840
cgaccaatgt tatcaattgg gatgctgaag gtcttggctt tcatttttgc ctctcatgat  63900
gtagtgaaac ttttcaatgt aggttaaatg atagccgcaa gttttattga agtaaagttt  63960
tattgaatta aagcccaaca tttgttgggc ttttaccgat attattcagc agtgcgatca  64020
ggtgctgcgt taggatacag cgactcataa agatcttggt atttggcgct ggtctcgatg  64080
gtcttggtat aagttccacc agcgcgatcg gtaacgactt tgcgcagatc aacggctttg  64140
atgcctgttt cttttgccaa ttcagccagg gcttcggtaa caaatgtctg ttcagacttg  64200
atacggatct gggcggcgcg acaattttct aaagtctgca tcatcttttg acgcagtttt  64260
ggatcagaag ggagttgata aaaaccaatt tgttcaactg acataatata tcctcattaa  64320
tgacgagaac cgagtggacc gatactggtt cccaaacggc gcaggaagaa ataaacgata  64380
ctgtgaaaac caaacttagg aataatatca acgccttcaa cattgtaata ttcctgagtg  64440
ttggtctgta ctggcaatgg aaaagacgga agatcaagct gaaccaattc acctggttcg  64500
caatgtatct tgacattctt accccaatgc cgacgattct tataaaattc tagagtctgc  64560
tctgtagtga gtttgagact ggtttctcca gactggcaca cctgttgtgc cgcccgaatc  64620
aggtcagcta taaatgcaac atccgacatg atgtgctcct gggttaatat tcagatcata  64680
gagattatac cctatgatca ccattattga agttaaccga aattccaatt gttcacggtc  64740
tcggctttct tgacatcatt tacgtcgcct gttttgttta agtcatgttt gatatgaaca  64800
ttctcaacat aacgggcttc ctcttctgtc agatctcgct tgacttcatt ccaatccaag  64860
tcaaacaata tctgtttatc ttgatccata ccgaacaaga acgatttgag tttctgttta  64920
ttggcataac ggtttttcaa gatagacgct ctggctttct taacagccgc cagttcatca  64980
ggggcataga acgccatgat gaagtctgca accttcggaa taccgatagc atctgccagg  65040
tcgctaatat caccatcagt cgccgattgt ttttcacggt taaattgcat acctgtccat  65100
acagggcaat caaattcaaa tccaagcgca cggaattctc gcgccacgga tgtataatac  65160
acgttggtgt tttgcatcaa gtgagcggga aggcgagaag atgcagattc ccccaagtag  65220
```

tctataataa tgacgtccgg cgtaattccc gtggatgtcg cgtaatcaag gatatcgcgg 65280
cgatacagtc ctgtatgccc agcgcctgaa ggatattcct tgataacaat atcacccttc 65340
atggaaccgt cttgacgagt tcgcaacttt tgtatcgtag cgacatattc atgtcgtgag 65400
agcttctcta aggactcgaa gtccctgcgc atcatacggg catcaaggcg gtgacgccag 65460
acgttctcag ccacttctag ggtgaatacg aatacgttca acccttgctc ggagtaacca 65520
gcagccaaat caatcagagt tgttgtctta cccgcattaa ttgcacccgt cacgatgttc 65580
agcgttttct taccaacacc accacgagtc gctttgttga atatctctac agcgaaagga 65640
atcttcgctt cattagagtt catgtggtcg tattgttgtt cagccatttc ccaatagata 65700
tggccaagat aagaatcaaa acttatcgcc aacgcctctt gtaggagagt tggaatcgtg 65760
ttcatctcat ctttacgttt ctcatcacca tagatgttga cggcgtgttt gatcgcatta 65820
tgaacagctt tctgccgcgc ccaactttct gtttctttta caagccattc ctgatggaat 65880
gtgttgtcat tgatattctc aagagcagaa atagcttgtt caaatacgtg ttcgttgagc 65940
gaagtctttt ccagcataat agacaacgct tcaaccgaag gacgagcatt atattcgcaa 66000
gtgtaatggt caatgagacc gaatataatt ttctcgcctt cgttatcgaa ataatcggct 66060
ttcaaatacg gctggatctt tctttgatat tcttcgttat agattaattg ggaaagcacg 66120
acagattcga gtaacattgg taactacccc accaaaattt tgttgtaatc ctgagcattt 66180
tgctgtatca gatcaactaa gatatcccca gacaccacag tgaacaagtc attttctttc 66240
aaattaacaa ataacaaacg ccatggtttc ttcaatatat ctgttgtaaa ggataaccga 66300
ggctctccat tatctaaatg gacacccact ttccctatac gaaattgaac gccacggaat 66360
ttgccttccg ttatttcgat tattgctaac tgatcagaac cagggtcgat gatttttgtaa 66420 ttaacggggg agtctcctcc ccctgcaata ttactcggtt gttttgatga cattatcgag 66480
gcgctccagc atatctgcag gcataaccga actctgagag ataccgaaca tgttgttcac 66540
atcgtcaaca aagtctgggt tttccagcag cggataccag aagtcatccc ccagctctgc 66600
cttacgatat ttcttttctt tttctggatc aaacccgcct ttggcagtgc gttgatacca 66660
agaaccactc accaaatcca catacccccag catgcgcgca atttctaaca taccggacca 66720
acggtcaata ccgccttcat acaacacagt gacagggaat ttggcttttt cacggacaaa 66780
gcggcctttc ataatgttga ctgtaaactg ccatcccaaa aggtctttgt cttctttgac 66840
ttgagaacgc gtgatgaacc acaattggtt agaagacagg aacccctgtt taccgccttt 66900
gatgttcggc tcggcgtatt ggttcccgat ttcatcatag tacgagttga tccataccaa 66960
aacgaatttc ttttcagtga ccaacggggt gataacacgc caaaaactat tgagagcgcg 67020
agcgcgggtc atatcttgtg tgtctttgcc cgcgatggca tcatcaactt ctttggtaga 67080
cggcaactgg ctgattgagt caatgaatac gatgatcttg tcacctttct gtgcatcgtt 67140
cagaagctgt gtcagcttga tcttcgtctt ttcaacgttt tcaatcggca gatacaagac 67200
acggtccatg tcaataccca tagatgtcca gtagttttca ttcgcaccgc cttctgaatc 67260
cgcgaagata caaattgcat caggaaactt atccatgtaa gccttaacat ccaccagccc 67320
aaacatggtt ttgaatgtac gagaatcccc caccaactgt ttgatgcctg atatcagacc 67380
accatcaata cgaccggacc aggccaaatt cagaatagga atacccgtac tgcaaataat 67440
gtcaggcttc agcgcatcgg tctttgacag cacttcggca ttcgggtcca gtttctttgc 67500
tgtcttgagc atgcgagcca tcaatgaatc ggccatttcg tttcctcttg cttgttgatc 67560
gtaattaata aatcggtgcc caagactttc ttggacaata tattgattgc ttcatgaatc 67620

```
gccattattg acgggagttt ttcatcgtta atttcggaac ccccgcgttc tgttaaatac  67680
atattacgca gacgattgtg ctgtgccctg ttgacacaag aaacattcaa tgcgatattc  67740
aggatataca tcatttgttc agttgtaaca tcctttggaa tagcatgaac ataatatatc  67800
gcatcttcaa aatagatatg ctgtaatgac tctggaattt cttccccgcc aaaagcaaaa  67860
tcttcaatgc gtttaaaaag tgtttccggc tctggtgttg taatatgttg tgttacagta  67920
gccgcaccat ttggcccttt cttgaaattg gtcgcaataa cgacatgacc gcctggttta  67980
ataaactcag cgaagttctc tgccatgtac ggggcatgtt ccgcataata tgatacgacg  68040
actgtaaaca ttagaactcc agagtcagag ggtttcggc agacttgtca tagttcgcac  68100
cgccagcagc acgtagacga ttgcgatcgt tcttgcgctt gtgggccagc atataggttt  68160
cggtgtccag atccaaataa ccacaagcct ttgataaaaa ccgcacaaaa cggataacat  68220
ctggttgttc cataaatgac gtaaaacatt ctgtgaccga ttccagattg gccgatttgt  68280
ctatcactcg tccgtccttg aagaaaaggt caatctgcat ttcaactggg aaagcagaac  68340
caaatccaga taaaatggaa gacaacataa aatgtaccac gtccaccaat tcgtagacag  68400
ctgcttctcg gtcatattgt atcccaccgc catagatttt ccagtcctgg gttgtttcgt  68460
caagaaactc tgcccactca cgatagatgg agttcaccac cgccacatga gtccaatgtt  68520
tacgccactc ttccccaaaa taggccacat tggtggcctt ttgaagttcg agcagacttt  68580
tgatatgctc tgctgtgatc atttccgttc cctataaaat ttgacgaatg gttgccaacc  68640
ttcaaatggg ttaacaaatt cataatcaac tttcatctca tcaatgaaag cctctatgtc  68700
gtcctctatg ataccgccgc gatctgcctt tgaaatgcgg gtgatgggac atttagtgct  68760
cagcgcccat tcatattctt gaggcgtccg tagatcactc acaatataat gaatgttagg  68820
attctgttca actaatggga gttggtaacg cttaaagaaa gacaaaaaca gatccggttg  68880
gacataacga agccccgtat cgctgccgag atgaagccag atctgccttg ggttaatcc  68940
cttggggtta tctgggtgaa catatggcaa gtccttgata tcgtcctcta cttcctctgg  69000
caaccaagga tagatgtaat gagccacccg acgcaactcg tctgagaaag ataagcgctg  69060
gatgtccata tcaccctgta aatggtgata gctgatgagg gactccaaac agaagtcctt  69120
accggagcgc ttgcgccccg taaagaattc aaggttcgga tacatcatac tgcaccttcc  69180
aagaacttgg gatcaacgat cttgcggtca accggagaat gggcgagcgc gatgttcaaa  69240
ccatgatcct gaatcaggtt catgttgatg agcttgtcgt tcagtttgca gtacaggcag  69300
tacgccatct gcacgatcag accgcgatcc gcgccgtact ccttcaggtg agcgacaaca  69360
gtttcccacg ggctaccgat atcacagtga tgaagcacac cagtgaacag attgcggata  69420
tggttctggt tggtcacgtt cgtgaagtag atcatggagt tgatgaaacc accagtgact  69480
tttgtgtctt tggtgatctt gccaagctgc ttctggctga cttcattgtt gtagtaatga  69540
agattgttag agaatagctt gtactgaccg acatcaacat ctaacacctg agcaatcact  69600
tcctgaagaa tagagaactc aatgaagttg attgaactca tcccccacag aacatcctgt  69660
gagcggttga tgaccgtcag gttcagacga ccttcaacga tggagaacaa cagagccagg  69720
ttacacacca tgtccttagt ctttgcttcg ccgctctcgc tgaacttcgc cagaccagca  69780
tccgaatcta gagccggatc atagatggtg aggtacgctt gacgagtatt tgggttcttg  69840
cgtaggcggt tgataacgct atccagctgg ccatgggcgt acagacgcgg accataagcg  69900
gctcgccatg tatggccatt atcagagaag ttggcggcgc gagggaggac acgggacaag  69960
```

```
aagcgcacat catcgcgccc agacagaacc cagaaggtct cgccgatggc agcaatagcc  70020
gatgagttgc gtccttcaac agacagccaa cggtcgcgga tgtcagagac ggtgatcgtc  70080
acaccatcaa taaaacgagt gccgtctgtg ttgatctccg cgttaccagg gtcagattca  70140
atcccgtgct cacggatagc caagacagcc tgtttcagca tgtcgttgtt gttaattgct  70200
ttgatttcca tcaataaata ctcccaaaat cacgattgag aaacgcaaaa acagcctgct  70260
ctacagtcag gccatcggac ttcatcatac ctgcgggaac ggtagggaac aagcctttat  70320
gccgttgacg gtgatcatga actctctccc acttctcgac caccagactt tcattgaagt  70380
ctgcgccacc gttacgcgat ttaacacggg caatacaggt ttcaagaggg gtatccataa  70440
agaggacgac caattcacgt ggtgggcgtg tcaggcgggg aatccaagaa ctcaataatg  70500
tagacggaat gatgccttca aaaatcacat catatttcag gtattctggt tggtcagcaa  70560
tagacaacgc gaacaacatc tgctcagtat ccttcagaga atcaacccct ttggacttag  70620
acttgtcata tttaccgaca cagacaatat tgtaagatgg acaaaccgtg agcatgatct  70680
tactgttatg ggttacgaca tacgcctgag gatcattctc cgccaaataa gaaggcacag  70740
tagacttacc actaccattg gagcctttaa tgtaatacaa ctctcctcgt gccgaatatt  70800
ccccttctac agcaggtggt ttgacaaaca aatgcacagg gcgcttcaac agccctttga  70860
gcgaataaga catgacatgc tccaataaac aaaaggagct gctattatag cagccccttt  70920
atctattgaa cgcttctgaa ttaaattacg cagcagcttt cgcttcggcc aacgcctgtg  70980
gtaaccattc attgattgct ttcaccagag attcggcatc agtttctttg attttctggc  71040
gtttggtgaa tgatttacca ttcacataca gactgaaccc ccagccgccg gaaacgattg  71100
gcgccagatc aacataagta ttggtgcggg cgtgtggatt ggcttcatct gccaattcgg  71160
taacagggaa ctggaaccag cgcatatccg gattcacata gctcaaataa accccaggca  71220
caacccccga ttcaaccgca gccaggatag gaccataatt ggatgcgcga gccgcttcaa  71280
ccatttcttc acgcttgtta tgacgacgct tgcgttcttc ggtagaagat gcagggcgca  71340
tttcagaaga tttcttggcc agaaccgcct tcgcgttcgc taaagcctga tcatccttcg  71400
gattttcaac gtcggcgatt gcttcagcaa cggttgtgcc cagcatacga cggcgaactt  71460
cttcagcacg ggcttgcgct tcttcgtcaa gaacttcttc gccttcaact accagggaaa  71520
tggaaccgtc tttgttgact tcaagagaac cgtcttcgac ggtctgggaa ttttgatcac  71580
cgacaggttg cccaaccgtt tcttcggcgt caatcaccgg atttgattca ccgtcgccct  71640
gtttaacccc cgcatcttcg gtcggtttaa ctttttcggc ttcagcgcgg tcaagagctt  71700
cgagagtctc ttctttctct tcctggctca gaccttcaat gagttcaaag ccgttggctg  71760
actggaggac gccttccatc atacggcgta acgtgacgtt gccgatgata aggtctgcac  71820
ctttgatttc tgcttgaaga tcagcagcgg ttttaccatc aatttcaaat ttcaggccgg  71880
actcgatatg aagaatatag gacataataa aaacccttttt gtgtagtaac cttctttggc  71940
agtttaatgt tcaactgtgc gtctggaaca ttaatatact gccttttttag aagatgtaaa  72000
ccacttttta ttgaaaagtt ggttaacact tctgtgttag acaacggaac gctggaacag  72060
cgcggactga cgtgaatatt aactttgtat atcaatattg aaaactgttt caggtggcca  72120
catggcagac aactcgattt gtgtgaattt gggttgaaca tactggtcca aaacttcgtc  72180
ccagagagca tgttctatgt tggcaatcaa caattcgtcg tccactattt cgacggaatg  72240
aaccactatc cggtggtcat aagtcaaagc atcgctcaca tgatcatttt ctgctctcag  72300
gtgctgcatt atgaaatatt cgattacaga ttccagtacc gtgttcagac gaacatattt  72360
```

```
cttcatacag cccctgctt gtgctacaga tagaaattag ggatttcgcc ggattcacaa  72420
ccaaacccgt taaaattctg ctcaacgtgt aagcgaattt tgttcaccac tacctggcga  72480
tgctcttctt ccatacaacg ttcaatcaaa gaatacgctg tatatgacag actgttgaac  72540
aatctggaaa taacaaggca attctcttca ttgtaaacga cttcagtatg gattgcgaaa  72600
gcgtggtctt cgtcggtaag aattttacag cctttgacca caaatggttt ttcaaagaaa  72660
tcacgagctg aatcagtgcc agattccggc attaaacgga aatcgccttc ttctccgaaa  72720
accgctttca gattttcttt actgaattcc gcttccatct gtatacgttt gtcggcaaga  72780
tatttcgccg caaagtagaa tttacccact gcatcattag cagcgcggcg gttcgtagcg  72840
gcttgggtat aaccagaaac gaaatcttca atgaattcca atgcttctgg tttgccaaaa  72900
cgaatttcgt cgcccagatc caagctggct tcggaatcaa gttcaatgcc cataacccta  72960
agaagatccg tttcattcag cctgtgttga ttgaacaatt gttctctgga atatcccaac  73020
tggctaccga gttcatatcc ggttttacca cccgaatctt tatgggtgcg atcatagcga  73080
acgcaattag aactgaattc aataccaaaa atacgatgta gctgtgacat atcataacct  73140
catgtttata gaaagccgtt cgcgaattat cacgtagaac ggcttttaga actaaccatt  73200
tttgtgttta cgacgtgcgt ccttccaaac agacatctga ctctgtttct ggaatcgagc  73260
agtgcgcata aacaaaacga cctcccaata ttgcggttca atttcataaa gttgtgaacg  73320
aaattgatct gcgcggtata atttgacaca atgattgtac aaagggtgat tcgcaaaccg  73380
ctttagcgca tcccaggtaa gtctcaaacg tgttttagaa cgatatgccc gttcatttct  73440
caatttaatg agatcttcaa ataccaacaa tctgagttta ggcggtaaat aatggaggtt  73500
taggccataa agataggtca caccacgttc accgaatttc accccatccc ccttcacaaa  73560
attgaagaag aacaccagag gatacatatc ccaatacggg agttcatctt tagtcagcgc  73620
gtcatatttg aaataataca tgcggccaac aatataacga acgccctgaa caggacgttt  73680
attttcagcg aatgctttca tcatgtgatt cggagataag ttagcatctt tcgatacgcg  73740
ctccataaac cacacatgag aacgacggat attacgcttc gcttccggac caaaatgttg  73800
acgatatttg cggatgtaac gcttgaccag ttctggggcg tccatctcgg cgggaagcaa  73860
caacgggtct tcttcaccca tagcgttctt agccatttgt caactcctta taaatatcaa  73920
cagatatatt atttaaatgg agtcctcatc gtggaagact atcgcaattt tctaacgcaa  73980
ctgcttcaac ggggtatttc ccgcaagaac agatttcgtg ttacaattcc attgccgcct  74040
gggatatttg attccaatgc aacactagca aatgatggga acgcgtatcc ttcatcttca  74100
ttcggcgatt tattcaaaca aagcgcccgt attgtaaacg cattctttgg agggacaaac  74160
caaacatctc gttccctgca aatgatgtgt atggtcgcat ctttacctgg tacagggatt  74220
gacactactc ccatgaccaa caacggcaac cacattaaaa tgccgaacaa caagacgaac  74280
attgatctgg agttgtcgtt cctcctcgcc aacgattatt atgaaaagtc ggtcatggac  74340
aaatggaaga atctgatatt cgacccatac acaaccaaga tgggttatta tgaagatttc  74400
gtgaccgata tttgtataga acaaatggat acagaagatc aggttgttca tcgcgtttat  74460
gtgactgagg ctcaccccat caacttcagt tctatagatc tggataaaag cgccgccgat  74520
caatttaatc agtacaacat ttccttttct tataacaaag tattatcgga gactgaatat  74580
gaaacgcgca gcctcgccag cgattttctt cctttgggta ttactgatgc tcttgcttcc  74640
ggagactggg aaaccgctgc gtcaaaagcc ggacagctgt ataaaaagat caaagaagga  74700
```

```
aacttcacag gtgaagccct gctggcttat aagcaactcg atcagcttgt aaacaatctg  74760
gctggtatca gcctggctga tttcgaaagg atctctatcg gcatccagag ggatatctta  74820
ggcaatgata acctgacggc gtctgagaag agtagtttac tcggattgtt acaggacgtc  74880
gttaaaaact aaaaagcccc cgaaggggct ttagcgaaat tagtcttgct tcaggaactg  74940
ctcgaactca tcaatggtag ccgtctgttt cgcatcggca ccaccattat tggctggaac  75000
agattgctgt gcattagaag gctgagattg ttgttggttc agactttcct gcgctgttgg  75060
gcgctggggt tcctgagact gggtaggcgc atgtgccata gtagaagcac caccttcaac  75120
cagaggctga ttatcaggga tggccagaac tttgcgcaaa cgtttttcca gatcttcgta  75180
cgatttgaag ttggccggat taaagaactc aaacagactg tgttcttttt cccagatctc  75240
ttcaatgtat tcgtcggttc ccagcggtgc cggagtatcc cacttcacat tggtgaagtt  75300
ggccaccaga cctttccagt ttccgaactc tttctcttca ccaaagaggt tcagaatcag  75360
gttcgcgcct tcccacatat cgaacgggtc gaatttaggg tcagttgaga acttaggatt  75420
ctgagccgaa tccaggattt tcttgacggc attaccgaac tcaagcaaga agaccttgcc  75480
gttgttttcc ggattgttgc catctttgat caccaggatg ttggcgtagt atttggtgtc  75540
cggcagacgt tttttgagaa ctgttttcag cttttcatca ttcgtttctt tctgttgtgc  75600
ccacagagga cggtcatggt cacgaacagg atcatcgtta ccgaaagtct gaggagagtt  75660
ttcgatatac caaccaccag caccctggaa tgcgtgtttc atgatcatgg cacacggagt  75720
taacacagca tcttcaggga tggtgccttc ttcttgagcc ttcatgtcca ccaaagggat  75780
cggcaggaaa cgaatgatgt tttcagaagt acccttgtca ttccaggtcc acttccagat  75840
gcgcgggtca cgaccgccac caacacgctg gccttgctga gcgagtcgct gttgcatagc  75900
ttcggcttgt tggccacgag attgtttaag acgatcaaat aaattaccca ttttaatatt  75960
cctctataat ccgccccttc gggctattct gtaaatgtat ttgtcaatta ttccgacggt  76020
gtaattatac tgcgttttgc tattgagtta acccgcaatc atttgtttta ctgggtctat  76080
ttcaataatg tcgtacacat ccgagaaggt tttgtgtcct tccaagaatg tatggtattc  76140
gatgacatag gatttacctt ccggcgtcgt gtaacgtaca cgatccatat catcagcatg  76200
ttcattgagg ctaccgtgac gccagcggat agaacctggc agatactctt gcgccttcaa  76260
cattttatag atttgctctt tgctcatgtt acaaccttaa atgagttttt tagatttcaa  76320
ttcacccttc aacaaccgag catcagaaca ttcagctgtt agccttgaca gaagaggagg  76380
cgtgatcaat tttttgacct ttgcttcttc gatgtcatac tcttcacaaa cactggccat  76440
cgtttcaagg attgattcct tgcgttggct tgctctcatc aacaccaatt cggaaaaaga  76500
atctggtgtg agcacttgtg ctatttgttg atcagacatc gattgtattc cccttccctg  76560
attgcttctt aatatgacgc aaaacgtctt tgaagccatc aggcgcggac tgaggaccac  76620
gaacaccaga tacgatcttt ggtgctccga taatcatttt tatttcgccg ccacattcag  76680
aacatggctc taattcaggc gtgtgacgtt cagcacaaga ttttcgagca ctaaacgaat  76740
ttccacaacc tgtacaggca taatcataaa acggcatgaa tcgcctccaa tacgtgtcgt  76800
agaaatataa taactgctcc caccagcgta gaaaacagga caatcctgct tgctttatca  76860
cgcagcaaaa catattcggc caacatatca gattgatttg cagctcttac attgacgtca  76920
ctatgggggg acacagcata gaaagatatc atggcactta atgaatgaag gaatgtcaga  76980
aatcccttaa cccaaataaa tgccgttatc aacagcaagg cgaaaagcag tatgtctgcc  77040
aacagccagt aattaatcat ttcttacacc tctattgaaa tcgggataat tttctatgaa  77100
```

```
gtaaggtcca gacaccatgt ttgcgaatga gtctacaaga tcatcgatag gctttggatc  77160
cttcacgtcc aacatgtcca ttataccacg catcttaacg ttgaacagct tctcaaagtg  77220
atctatcatg accaatttgt cggcatttcc tttaccacaa aaatgtttct taacaaaaga  77280
cggggtaaca atctgaaatt ccatattgtt acggcgcatc gcttgtttca atagagatgt  77340
gttctcggcg gtttggcata tgttgttgga gttttttgaa ttccccatag catagccttc  77400
tagggtgatg aaatccggct tctctgtaag aagtacggct tcagcccatt tggaaatgtt  77460
ataaaaccgt tcttcagggg attcatattt gggttgacgt aaaataagaa tattgtgtcg  77520
cacttgacga cagtgcttct caacggtatg atgtgcatag aaatgaagat gatcaaaatc  77580
cagaggatct ttgtcgtccc agaagcacat ggctggacag ccgtaagaat agtcgattcc  77640
gcaaaatttc ataaaaatac ccataacgaa gtttcattgt gttatgggta tttagaccgg  77700
attatctggt gacgattttg ctttccggta aaatcaggcg aggtttggag tccatttctt  77760
cttgcatctg acgtatctgt tgcagtaatg cagaagtgtc cacatgacgt ttgatccctc  77820
gcgcctcatc accatacgac acatggccgt tggcgtccac ataatgcgcg gtgcaaacca  77880
tcaaaacata acccagctca ccgacggcaa ctgtcagatc gaccacttcg gaagccaaag  77940
actcaccatc aacactgaga ttgggagaat aatggatttt accatcagcc ataaattcgc  78000
tattcagcat aatcatgcca gcgatcgttt gtacaacggg gttcccctga tcatcggcaa  78060
cgaaaccgtc gaatgcgcct tcaaaccctg gcgcaatttc tccctttca tttgtgataa  78120
cagcacggag gcgttgaagg ataacttttt gtacttgctg gatatcagcg cgttctacgt  78180
ttggcattat tgttctccag ttcataatcc cgttctttaa catattcata aagacgagaa  78240
gtaattcggt cggcgttgcc tgtggtattc ttcacaaccc aaccgctcgt aaggacatcc  78300
attttatatc cgtcatcgct atcttgaaaa taacttttaa ttgattcaag ccgacgacgt  78360
ttatgaaaat atggtattaa ttcgccaatg atgacacaat cgggataatg cttatccaga  78420
gtgtttatgt ctcgttgcac ccaaaccgga ataacatcat cctcttcaat tgggctgtac  78480
gttggatcaa cgataatcac attgaatcca taattcaata aatctttaac tcccagccgc  78540
ccgaatttca tatcggacac ggtcatggcg acattcttta tccccaattt atttgcaaaa  78600
tctgtgagta atacaaaaaa gtccgtgttt gcatccggat aattaattgc gagttgctcc  78660
cccactttac tgaaacagaa cgcgtgcatt ttcagtcctc gttataaata caattacaat  78720
ataccgtgga gatacattat gaatttacca tcattgccca aaactgagag aacacataaa  78780
agtgatttct ggccgactgt gatcaaatac cgcgccttta cagcagggca acagaccatg  78840
ttacttcagg ttgctgatcc gaacactcct atgagtgagc gcgtggcaac attggagcaa  78900
ctatttgaca gttgtgttga tgctggcgtt ccctttagta aactgccaat cggtgttact  78960
gaagaagtat ttttaaagat gcgctgtata tctatcggcg aggtcatgaa gatacgttac  79020
aaatgtaaca ataaagttca agccgacata aatgaaggtg aagaaccagt ttctggtgtt  79080
aaagattgtg gtcaagagct tgtgttaccg atcccgctca atcaggtaaa atgcgtgtcc  79140
ccagaaggct tcagggagac gtttgatcta ccaggtggtt atcatataaa gatgcgccag  79200
ccgtccttct cggatgcctc agtgctcaac gaagcatcct ctgttgaaca aatgattgcc  79260
acttttatcg attgtctgta tgacgacgat ggtcaggttt ggaaggtgga aaatccggct  79320
gaacctggta tcgatccaga agttgctaaa gaacgccaac gcattaagga tgaatttgtc  79380
aaatgggtcg gggacaatat tgaatctgag attgttcagg acatttcgaa tgatttcttt  79440
```

```
aaaaagattc cgcgtattcg ttacgcgaca aaaattaaat gcccttcgtg tgggaaagaa  79500
cacgaagtca aatttaacag tgtcaccgag attttcattt aatttttgaa attgatttac  79560
tctcctattt tgtgatgtgt gacgaattaa aggcacacgg ctatagcata tttgaaatca  79620
gtgaatcgat gccgtggcat cttgatttgc ttaccgagac actgaaaatt agattgtcta  79680
agaaatcttc caaccccacg taatgtgggg ttttctttgc ttacctgttt tataggttaa  79740
gacaggaacg tttaacctta aattgctata acaccgttgt tgctgaagta agtgttgtgt  79800
aattggggtt tgaatttgtt ttgaagcaaa aataatcctt ttctacgcat gttctgaggt  79860
gtacagtatt ttcctcgcct ttatgcctcc atggcattgg aatgggactg cctgtcaagg  79920
cggtgttacg agcttcagcg agtaggaacg aaaagaataa aggttgaacg gaagcagagc  79980
ttcctataat atattattcg acagatttca aatccccgcc ataaatatca catgattcta  80040
attgactaat gggtttcaat atgttagaca acttgcgttg gttttacggg cgcgttgaag  80100
acgtgaatga tcccgatcaa aacgggcgcg tcgcagtacg catctatggg gtacacacgg  80160
aggataccac tctcctgcct acagaattat tgccttgggg taaaatgctt atgccagcat  80220
ctaacgcatc ctcggcaggt ttaggctggt ctccgacggg tatcactgtc ggctctgacg  80280
ttatggggtt tgctttggat gaagcatatc agaacatccg tattgcatgg gtatggccag  80340
cagcaacacc aacagatggg tcagatacaa acccattggc gctgggccag gtcgttcaat  80400
ctatagaaag gcagaagtat aatgccgtcg agaatgttcc tgttaagatt gaggatgaac  80460
cacaaccgga tccacaacca ccagtagacg gttatgatcc tgagaagtgg atgaccgtgg  80520
ctcgtgggga attgggcgtc aaagaatatt ctggtaagtt caataacaac ccaaggatat  80580
tggaatatca taagacaact tccctggggg cgtcagaaga tgaagttagt tggtgtgcgt  80640
cgtttgtcgg atgggttctg atacaggccg gatatacatc aacacgttct gctttggctc  80700
gttcatattt acaatggggg tctcctctgt cagaaccacg ttacggcgct gttgtagtgt  80760
tccggcgcgg gaacaacccg acattcggtc acgttgcatt cgttcagaaa tttgacgcca  80820
actacgtttg gtgtatcggg ggaaaccaat ccgattctgt gaaggtgagc cgttttagcc  80880
gctcatccgt gttgggttat cgttggccag gtccagcaac tacagcttca gcagctccgg  80940
cacaacaaaa cggtaaatgg tctgaaccta ttccagatcg taccccgaaa gtccaagaaa  81000
caccgcctcc ttctggtcgt gttcaggata ttgacaacac aggagaggta tcggttcctt  81060
cggctggagg gtctcgttat ccatacaaca atgttatggc ttctcgagct gggcatatta  81120
tggaggtcga tgacactcca ggcggggaac gtctccattg gatgcactcc tcggggtctt  81180
ataagcagat gcttcctgac ggggacgtgg tcaataaatc agtcaaagat cattatgatc  81240
tgacgatgtt tgacaaacgt tattatgtgg ggcgcgatca taacctgact atcggcggga  81300
ctgaagtaca gcgtaagaca ggagaagttt accacttgca ctcttctaac tactccaatg  81360
tggtcgctgg cacggcgttg atgaaatttt cccaattggc tgagatacag gcacagaacg  81420
tgttgcgtct catctgtgaa atgttggaag tttccaatac tttgaaagtg cctaaaatac  81480
tggctagtga aatagtttgt gataagttgt cggtggcgca gactattgaa ggcaacatca  81540
aatatgctga aggcgctggc cgcgccgcct cacgtgcggg ggcaactcct gtaacaacta  81600
caggcccagg tccaattgat ataaaaccgg agttagagga taacggtggc aattttggtg  81660
gtaaaggcgc atgattacac tggtgagggc agataatgcc ctctcgtgct ggagaggcaa  81720
tatccaaagg ggtttaacat gaaagagtac aaggacattg acctgaagtt tggcatgcat  81780
ccggtcacca aagatgtcac taagaaaaca ggcatttatg ctgtactaca atctgtgcgt  81840
```

```
aatatagtga tgtcgacggt aggtgattgg ccgacgtatc cgagtattgg ggcggggttg  81900
tataccatgc tgggagaaaa tacaaatccc acgatacagg tcgacgtgaa gaacaaagtt  81960
gaagatgcca ttgctctttt tgagccaaga gctgaattgc aatctgttga tgtatcattg  82020
tcggacgatt atcattctct gggcgtaacc atcacgttct atgtggttaa caacccagag  82080
ccgataacag acaccatatg gttaaaacgc acaaactgat taaggtgcgt tggtattgga  82140
gcggttggta attatttcaa aatgcgtcag taaacggtac agtaatttcc cacctattct  82200
atggactatg gtggttggct ttaggttaac caccatacca tctagtctcc ccgtcaacac  82260
aaatgttaaa cgaatgcgca ggacatcact gccttcagaa cgcattattt gacagtcatg  82320
gctgtaccct atttctttcc ctttgaggac aagaggaata tgtgcgcttt cctttaacag  82380
gatatctaaa ttttcaaata aaggttcttc tttgttattg acggaataca ccgtctctaa  82440
tatcgggaat ttatacatat catggcacca acgtaatcac aatcatgttg agtaccgtat  82500
caaccgcgac accagaatct tcttcatgga tagttgatgc acgtaaatga atgtcagaaa  82560
tataattgtc tatatgcatc gacgtcaaat aaggacggtg ttgatacaca ggacggttga  82620
cctgaacata ttcacgcaga atgctgaatg aaaagtcttc acattgagtg gtgtcaatgc  82680
gcaaaaatct ttgagcatgg caggtcttta actcggtcac tttccccaaa taatggaggt  82740
ctccggatga accgatgcgg aacatcacgt ctacttcaga tttgaaaatt tcgcgttcaa  82800
taagggtcgc tggtgcccaa caaacttctt ccttgtcttc tgggaataac gtatcgatca  82860
cttcaggcaa ttggatgtaa ccgaagttgt gacgagggtt ggtcagtaat ttgttagaca  82920
ttttgtgccc ctattacgtg ctccgaggct tgttcataag ctgtacggag ttcaagataa  82980
gaatcggcta acagaggaga tttttcattg cttcggttca tgattatttg atgattaacg  83040
acagcgcgtc gtaatctgag ttctgctacc caaaatgcct tttgttttgc gtggccaggt  83100
ttggctctta gattatgata atgcatagat gcatgatata tttcggagtt ggtcatgatg  83160
tagtacccgc tttcaatttg tggcgttggc caatgaatta ttgggaagta taggtgggaa  83220
ggtttcaaaa gtaaagcccc tcattgaggg gctttgaaag atcagcgttt caaacttgcg  83280
gcgagtccag taacgtcggt cacggtttgg tcagccagaa caatcacggg catagacatg  83340
cgttgcttac cagtgatttt ctgtaattct tccagcttgt aatctttgtc tagcttcaga  83400
atttggtgtt caataccgcg aatgcgacag atgttttcag cttgtaaaca ttgcgcacaa  83460
ccttgtttgg aataaatcgt aatcatttct cacctttagg caaatttcag accgtcggag  83520
actgatccag taaggacacc agtcagataa tcaggggctt ccgcttcctg taatgcatat  83580
tgcattgttt tattatctag ccactcattt atccatggca ctggattgtc tttacgggct  83640
tgtcctgggt atgggtggcc aatagccccc atacgatgtg ttgccaacca gtccaccatt  83700
tgatgaagga tatttgcatt cagtcccagc attgagccgt ctttgaacag ataattcgcc  83760
cattcttttt cttggttgac aacgtcgaca tacatctggg tcatttcgcc gcgcagttct  83820
tctctaataa tggcaaaatc agggtccatc agtggcagac ggttcaggaa agtctgggtc  83880
aggatgaggt gatcttgctc atcacgagca atctggcgga tgattttagc gttgccttcc  83940
attttgttga ggaattgcat gaaagcccaa gaacacgcaa atgaaacata gaaacgaacg  84000
ccttcgaggg agttagcagc aaacagagca cgccagaatg cacgcttggc gttcatgatg  84060
tcttcacggg tgaacgcgcg tccagccata cgcatcccgc tgtaacgcac catgtcgtcg  84120
tagtacacgc tgatctgtcc ggcgcaatcg acgatctcct gaacgtccag aacatggtca  84180
```

```
aaaacgatac caggatcatt cactgtgtta cgaaggatat gcgtgtaaga tagtgagtgg  84240
atggcttctt ggcgcgtcca ctccagaata gcaaattgga tttccggagt tgatgcccat  84300
gggccaaacg cttcgaacgg agcagcgccc tgaatagagt ccagcatggt ttggcgtttc  84360
aggttgctga agtagatgtg ttgttccgca gcggatagag tggcaaagtc tgctttgtct  84420
ttggtgacat ccacttcttc cggacgccag aactggctga gacctttctc ataccatttc  84480
tgtacaaaag gccatgcgac tttgtcatag cgctggatac tcacagggtc gccaaagaac  84540
ggcaaacctg tattatctga agatgggtca aatactgaaa attgcttttg ttcgttcatg  84600
tttctttcct gatgaataag gggtgacgaa tcacccctga tattaaacga ttgtgtggta  84660
tagacctaat cagacaacac aggtgtcgca gtgattcgga tcttcaattt gtttcaactc  84720
ctcgtcttcc ttggagtctt tgttggtgtt gtaatacaga gttttaccac cccacatgta  84780
gaaagacaga atatcctgca tcataagaga gcgcgggatc ttgccttctg gatatttctc  84840
tgggtcatac catgtgttgg tactgataga ttgatctacc caacgttgta tgaccgcagc  84900
cgtcttcagg tattcaatac aatccagatt ccatttcagg tcatatagag gaccaagggt  84960
ttctacatcc ggaacgatct gtttatagac gccgtccttg ctgcctttga tgctgatgag  85020
accttttggt ggctctatac cgttcgttgc gttcagcacc tgagaggagc tttcagttgg  85080
tgctacggct aacaacgtgg cgttacggat cccatactcg gataggttct gcttaagacc  85140
ttcccagtca agaccatagg cttgcccaac aggctttttg ccattgggta ggatgtccag  85200
cgggagaggc tgaaggtcgg ctgttacaaa tccggaatca tggatagttg acttcttaca  85260
agatccgaaa cgcatggcca gacggttgga cgctttgacc aagtagaaat gaagatgcgc  85320
catccacttg tctagaagtt ctaatccgat aggcgatcca taacccgtga aattcttggc  85380
caggaaatgt gcgacgttga cgataccgat acccagagga cgatattctt ctacggccaa  85440
acgggcttgg cgagctgggt agtcctgata ttccaacaac atatccaaag ctgaaaccag  85500
aacgaaagca acatcttcca tttctgttgg atcttcaaat gccgtcaggt taaatgatgc  85560
gagtgtacat agggcaatgc gaccatcttc atcatcatac tgttggaact cacgagtcgg  85620
gagcgcgatt tctaaacaca gattagagct ataaatcgtg tccaaattga acggactata  85680
ctcgttcatg tgatcaacga atgcgatgta gatccgtcca gtgtcagaac gctggtctag  85740
tagcatttgg aacacttctt cagcttgcag ctttttggaa cgacataatc cggcgtcggc  85800
ggccttgatc atattgtcgt acatttcgcg gaatttattg acgtctgcga aaaatgcttc  85860
atacatttcg cggttgtctt ttggatcaaa caggtataga ggctgtttgt tcaccaggcg  85920
ctcgaacatg acgcggttaa tctgaatccc atagtcgata cggcgttcac ggttctcttc  85980
caatccacgg ttgtttttga gaacaacgac atcatcaaat tgataatgcc agatgggaac  86040
atagcatgtt gccgatccac cacggatacc gccttgagag caagacttca gggcaccagt  86100
caaatacttg atgaatggaa ccagacctgt atggaccatt tcccctttac ggatagggct  86160
accgatgcca cgaattgccc caacatcgaa tccgatgcca gcacgtttgg aaacataatc  86220
cacgatgctt ttcgcagtgg cattaattga gtccaatgta tcaccagttt tgatcaatac  86280
gcaagagctg aactgtcggg tcggggtgcg gacgccggac ataataggtg ttggaagact  86340
gaatttgcct gtactggcgt attcatagaa cttcttcacc attgtcagtc tgctttcttt  86400
atcccacgct gagaataatg ccatagcgat tgccatgtac atgacttgag ggtttcata  86460
atacactttg ctgccagaag aacgatcacg caaaagatat ttttgagtca gctggcccat  86520
tgctgcccaa gtgaaattct tgtcgcgttt gtggttgatg actgtgttaa gttcttcgaa  86580
```

```
ttcttcttta gagtaaagtt cgaggaattc gcggtcataa acacccagct tggtgttctt  86640
tgcaaagata tccagcaaat gaggtggctt gtactgacca tagacaacct tgcgcaggtc  86700
atacgacttc aggcgggcag caacatattg atagttgggt ttatcaacag aaattaaggt  86760
ggccgcagct tggataatga tatcctgaat gcgttcggtt ttcatgttat cggtgaattg  86820
gatcttcgat gcagcttcca cctcagacac cgatactcct tcaaggccgt cacatgctcg  86880
ttcaataacg gtatggagtt tttcaatgtc aaaggggaca gaagatccgt cccgctttat  86940
gatgttaatc atagcgatcc tcggtttgtg tttatgcagg ctgttattat acgccgcctc  87000
catggattga aggcggcggg gaagttcgtg tggtatttaa atgttgtaca ggtcgttaat  87060
ttctaacatc aggcgggtga agttgccgcg accattacga tcagacttat cgaattcgat  87120
gatgctgaat ggttgaaccc actctggata ttcatccccg atttctacac cgtcaatttg  87180
caaggaacct gtttccagct tgttgttgaa gtctttaaag gaatccacat acgtctgtaa  87240
cgcactatca cgcagtcgct tgttagactg tttgatatct ccattcacga agatgtacga  87300
agaatctgaa gcacgggtca gtaagttctt cagctgctcc atatcgcatt cctgcgcctc  87360
ttcgataatc aggaaacact catcgaaagt catccccttt acagtttcaa ggtcttgaat  87420
ttctatgatg cgtttctccc acagatagtt gaagaaaccg tcggaacccg tatctgtttt  87480
gagaaccttt ttaaatgtct gtatgagcgg catcaaataa ggcatcagct tttcatatgt  87540
gtcaccaggc cggaaccctg ctgtggtgcc agttggaagg ggagaacgtg tgatgatgat  87600
cttgttgatt gttttgtcta tcagatgttt tgctgcagca gatgcaccac aataggattt  87660
gcctgtacct gccggaccga tagcgatagt gaggtgttcg tttaatgcgg attgatatgc  87720
gaggttctga ttttctgaga ggccattgaa cggagcaatt ttgaaatcac ctttagaaaa  87780
tttcatccag tcttcttcct tctggatggt ttctttctta cgagcagatt ttgtcttcgc  87840
tggcttcatg gatacaactt tagacgcaga ttgcatgttg aaccttccta tatctacagg  87900
ggttgtcgac acctttaatt aagcgacacg cccagcatac ctgtatatca gataaagaaa  87960
aaggccgttt ccggccttga gaattagcag aaactcttgt atgctgccgc cagtttagta  88020
tcatactggt ttttcgcata tgccggacca ttgtaccgac gagcaaactc ggcccaattc  88080
ttgttcttca gggctttcca catattggca tcagccttga tgaacttgac aaatgccaga  88140
aggtgggcgc gttcaccagt caggaaatca gtgaacatct ctttggcatt tgaatagcca  88200
cagatttggc agttgaaccc catgatctgg aataggccgt aggaagcact ctcgtaagcg  88260
cagtcctcgt caagggcgat tgcaccctga aggcgttcca actccgcgtc tccgccgata  88320
tacccgccag aattggggtt aaccaatgtt ggatagagtt ggtacagagc attggctctt  88380
gcttgctcga atttggccgt caccttttg tacatgatgt ggcgctcaaa cagagttttg  88440
atcttgccag ttttggtaaa acccgtgcca cgggattcta cctgattcac cgctttcata  88500
ctggccagct caacaccaag ttcacgtgct gcgtcaacca agtccgcttc ggtcagatgt  88560
tcctggtgag cgtctccagc gttgcggata gcatagaagg tctttggccc agcaatacca  88620
tcaataacca atccagcacc tgcctgaacg gatttgacgg cattctctgt tgccttacca  88680
aatatgccat cggctgtaag agagaaaccg attttgttga ggctttgttg aagtgctttg  88740
acttcagaac ctcggttgcc aagttttaga atggccataa gaaaatacct ccgcaatgta  88800
tgcgaaggta tttaaagtga aagtcgaact tgaggattta gtgtcgatta tctgactacg  88860
acgacaggca tgatttcttt gaaggaagtc ctaacttcgg aatcataccc atatttttca  88920
```

```
aatattttca acatcgcttg ttccagttcc tcttggaact gagggaagac tttgttcgga  88980
atgcgatcag caacccagag agcgcctgaa gaggcttgaa tgactgcccg gctcatgctg  89040
cttcctccct ctggagttta gcgacggcag cggcgatgtc catcaccact tcctgagcgt  89100
ccttacagaa ccccactgcc agcccgaggg agaaatcgaa tgcgctcggg gggcttgagt  89160
tcaccatgtt cgggttgcgg ttgaacaaag tgaatgcgat gttgttgatg cacatttcgt  89220
atgcggtcat tcgtcgtctc cttcactatc tttccaggag tccatgtgct caccgcaatg  89280
cgggcaatca ccgtcttcaa attccatttc cgaaccacaa tgcgggcaat acagaacttc  89340
ttcgtccatt ttgaatctcc taccaaaaat ctgaataagg aggggagttt ccccccttc  89400
gattaagcca gtttgcttac cagggtctga acgtctttgg cggtcagttt acccattttg  89460
acgtactgag cttttgcttc gccaccagcc gctttcacga tgtcggtgtt gtcgtagccc  89520
ttcttaggga agaccatcac agagaaggaa ccgttgttca gcgggttcag ctggatgcga  89580
cctttaccga ctacgatggt gccgtaagtt tcggtgttcg cttcgacaac gtggatgtcg  89640
tggcccaggt ctttcagcat gccaactttg tcggcagtct tagcaaccac agctttgtca  89700
accacaacct gctctaccag ggtgaagcca ttggtcgctt tcactttgcc gttcagcaga  89760
ttcatgaagg aagttttgcc accagtgaag ccagctgcct gagcgatgcg gaacatctca  89820
acctttgcaa cttcggtgtt cagctcaaaa gagatggtgc cgttggtgat cagagttttg  89880
gtagtagcca tgatgtaatt cctcataatg tagttgggtc gtttcacttt tcattcggcg  89940
gggtgttgtg taccgcccta tgtgaactat aatagtgcat gattattgaa gagtaaagtc  90000
tttttcaata aatttttaaa ttatttttga agtattttaa aaggcctcgt agaatgaggc  90060
ctgaagggaa ataatttgag ttaaaaagtt ttaggtcggc ttctttttca aatactggcg  90120
agccaaatcc atttgttctt cagtgatagg acaaccgccg aagtccacca ttccgttcct  90180
ccaaccatgg atgaaactct tagattctaa accagatagg acatatcctt cacgggcttg  90240
catatacccg cgaagaatct cttcatcgtc catactattc agttctttta aatccatcat  90300
atcttcctca agtcagaaaa tcgtaaggac gccgacagtc cctgatatac gttcttggct  90360
atgatctgaa gcagatcacg tatcgggata tttcccttgt cggggcgaac catatcattg  90420
atatccttcc acggtatttc cggtggaaac agaacgactt tgactccgct gtctatcatc  90480
ttctgtatac cgtcacaaac ttgtttgttc ctgtattggt tatcggggat atagatatcc  90540
cccttagcac ttaataagtc ggcatcggca gtcgcaagac aattgggtag aaacaagcta  90600
tcaattggac cttctactac caactttgtt ttgttccaaa tgatgcgctc ttccccgtag  90660
atcttagtat cttcgttctt aggcttgaca gtggcatacc gtaatacccc atcaggaagg  90720
ttatcgccga atgcgcgccc ctgaactatc ttcatgcgcc cgtcttgggt ccagaatggg  90780
attaccagcc gctcatcttc gggtatcttc ttttgcttct caacatccgt ttcaaaactc  90840
agaagatctt gacgaaaatt tctgctgtaa tacaacaaag ataacgtgct ctccggcatt  90900
cccctgcctt caacataacg acgggcgata tgatcacggt caagaagatc aaggcgtatc  90960
atattcccaa ggtgctcttc atcccgtttg gcgacctgag aaccgatacg cgctgtctgg  91020
gtcaggcgct gtagtggttt gagtttttgt aacgggcggg aactggtatc cccatgatc  91080
ctgaattttt caaggttgta ttcattatac agacgctcgt caaacttctt caaccagaat  91140
tcaaacgccc aaccgctcat ttcattacag ttgtggcact tgaaacgaaa cacatcgtca  91200
tcacgatcat aaaagaagtg accacgacgc ttgttggcac tcttcttaga atccccgcat  91260
aatgggcaac gaaatttggc gacagcgcca acacgttccc agctgaattt atcaagtcgg  91320
```

```
ggggcgagaa aattgatgta ttgttcgtcc aagaatttca ttagatattt ggcctctgga  91380
acacttctgt cacattataa tccaccccgc gactttgagc tatgcaaagc tgtcgccaag  91440
ccccatacag aatattttgt tccgcaacct gattgcgttc aaagtgggcg aattcttcca  91500
gcatctgttt gtaccctaat agataatgag ggatatctgt aggtcttctt ttgtccaaag  91560
atttagacaa atatgatgca taatgttccg gtgaagacaa agaggaatat tgcatatttg  91620
gaacgtgaac gggcttcaaa gattttctag ggtgaagta caacaaaccc catttgggag  91680
ggaggtcttc aattttaata acatctgctg ggcaaacata gaaacgatat gctcccatgc  91740
ctatggaagg attcatgcga tgaggtttct ttttgtctgt caggaagtcg gcgcgggaga  91800
ctttaacttc cattaatata gaacaacccc caggtctgaa cccgatggcg tcaggggatt  91860
cacgattatc gaatgaattt ggttctacga acacagcacc acaattcatt tgtttgtgta  91920
gaaattttgc agcgatttga caaccttctg agtgagaagg tataaagatt ttgcccattg  91980
ttatctgtat cctattgatg acgaatgggc aaaattataa cctgacgatg atcctattga  92040
gttaggacaa ttgcttcagt ttgtaaatcg tttgatagca caaagttttg atttcatcaa  92100
gcgtattttg aagatggctg tcgcattgac cataaattcc gtttacgtcg ataacaacac  92160
tgttgacata cgatatagga tctgggttgt acagtttaat attctcaaac cctgggacat  92220
atacaccacc cgcgccgata tatgcctctg taaaggtatc cagcaagtcc tccagttccc  92280
cgtagaactc cccgagtgcc ttgtgcttgg cataggacgt tgtaacgaag tggagggcat  92340
gagagtgggc tatagcaagc agtccacggt tgatgaatat actcgcattg accatgatat  92400
ttacccctaa aaagaaaatc cccctgtatt taggggggatt gtattttata atcacttttt  92460
accaaaaaac gattttaata aattatcagg aatttttgga agacctaatt ttgccgccag  92520
ttcttctggg gaattaccca aaatttttct accgttgatg agaccaccaa caaatttggt  92580
tcgatctgtt ggactgcgaa ggatagtgga ggcaccgcca acttttgcgt catacatcag  92640
aatatgagcg ccacggtcac cgacgaaacg ccagccttcc gcttcagtaa cctgaccttt  92700
gtcagccgac ttgccgaaga aaaattcaaa accatcatgg acggcaacga cttcttggcc  92760
ttgggtaatg ccgtgggtct ggtctggagt tagcttcact ttgatggtgt tgccattagt  92820
caattccaga ttatagatgt cggcctgatt atctggagtg atctgggtca cggtagcgcc  92880
ggagcaccac tgagtgccgt cggcctgttt ggtgatggtt acacttttgc cttgtatgcc  92940
gccatgagtt tgcggttgtt gagcttgttc tttaaaatat tcgataaacg gtttcatcgt  93000
ggatctccta aggattttga tgtatttagc cccccgaaggg gctatgactt atttcagact  93060
aatctgaaga ttaccaccca gcgattgttc atattcactg tatgcactat caccattact  93120
catagcccat tcgtcggatt ggcgagcgcg ttcaagagtc atgagatttg gctcggtagg  93180
attatagcct ttagatttcg cgtcgttgta taccgtttgc aggtattggt tggcacggtt  93240
gatctgatcc ttgaattcac gatatgctcc ttcggtcgta ttgcgacgga aagtgatatc  93300
ccaggcaaca ttcagaactg taccattact ggctgcgtat acctgccaat ccagatctcg  93360
tccattagga gcgctatcac gaatggatcc ggcataggtg gccagatcgc ctgcattctt  93420
accaccagcg acctgatctt tcgcccgagc caaagcatca atgactgccg tgcggttttt  93480
ggactgtgcc agatctttgt cttggaacat aattgcacca aacttactga cggtgatatc  93540
attcaggaac agcttgttcg ggttatagtt tgatgaaccg agatggctca attgagccgc  93600
agcgtctttc aggcgttgtg aagtctcatt caatgcatct tgcacagact tgacagataa  93660
```

-continued

```
ctgaatgtca tatccgctgc tattgactac atttcggcca ttttctgtca gcatggtcgt  93720
gatgttggcc ttattacgat cgaagtcgta agtcacgttc gtaacgaacc gtgcggcttg  93780
cagctggcta ccagcaggga actggaagtc ccaagccaca gagaacccat gaacggtttc  93840
accaaaaaat ttagcgttgc ttggtacttt gatgtttgca gtgatcactg cattttcact  93900
ggaattggtg ttgatttcac caaagatagt acgctcgtcg gaagattgaa ccaacagagt  93960
atcttttcca cgccaatcat agcggacttt gaatgttgta cgaggaaact ctttcatcag  94020
gtcaagtttg acagccttgc ccaaggtaaa ccgattcagc agagcgtcag cgatcttcaa  94080
tgtgaaagaa ccacaatcaa cgtaagaata tccctgggaa cgggaaattt tttgaatcgg  94140
atatggggcg ttattgatag gaaccacacg gcattctact tctcccgcaa attgagaatc  94200
ggctgcacgg gagattgcgc ccactatttc aaaagcggcg tttttcacgt ctccttccag  94260
cataagttgg tcatgaccag acaaatctga tactacttct acagaaagtt ttccgttgac  94320
aattccccag aaataaacct gaatgtccag accacccgaa gtacgatatt tgcccgcgcc  94380
gattcgtgtt agtttctcac ctgcatacat accgacctgt tgtggagcat atgtgtctac  94440
aatccccaga aggcgagcaa tataaccctg gttgcgcaga tcatccatag aaccggtttt  94500
tggaagagtt ttcatgtcga cgggagcagt agcccctatt ccaaattcaa catatgccac  94560
aatcttgccg ccggacttca gttcccatcc cattccctga cggtcagaag ctgccatgat  94620
tttgcgatcc acttcaccgc gaccgacata ttctttgttg aatacggtca cctgagcgat  94680
agattgggag cgggcaatct tcgccattgc gccatctttg accatgatgg ccagatcatt  94740
ggaactcaga gtcacgtcgt tggcaccgac taccttcaca acagaactga agatgccgtt  94800
ggatttcgcc atgacggaaa tgttccagtc agggttggca tcactggtcg ggaagttaat  94860
ttcacgccag tctttgacgc gttggttgaa attattgagc agatccgaag gaggaacagg  94920
aacaccaaat tcacgacaaa tatcttctac ggtcggttct accacctgct ttctaccgtt  94980
ctgaccaacg aggacatcgg cctcactcag gcttggggta atgtccaagt caaatgtgcc  95040
acgctgataa tagttgatgc gaggaggctg accgatctta ccacgccatg accaggttgc  95100
gggattgttg gtagtagcgc caacattagt gtcttgagta tcgttctgaa ccggaacgtc  95160
gccgaccttg tctggatcat cccatgtgac acctttcatt ttcgggccat cgaatacctg  95220
agcaggatcc ttacctttac gcacaaccca tacgaatgca cgatcaggga taggggtata  95280
cgtcaggtcc atgacattga gcttctgctt caggccggac tgacggatga tcttcggcag  95340
gagggtaaca ccacgttcca atgctttctt ggagaagtta attgcaaagc cgtcaatggt  95400
tttccccaaa ggcgtcgcca tgaattgctt tgttgcttca atcatggatg cgataacacg  95460
catcggattc ttgaaacgac cgatggcatc gggatatgtg gaaccacgct tctgaccgat  95520
aaagacttgg cgaacattct tgcctagacc ttgtggggta tagaattgaa tacggaattc  95580
tttttcgtct tcatcaacaa atgtgaagaa aatgtcgcca gcgttcttct tgccgaatgt  95640
caattcatat ggggatgagt taaacgcttc gtctaattgt ttagactctt caaggaaatt  95700
taagaaagat gggatggcca ttgtaattct cctgattata aaatcggtgc ggtttccctt  95760
aattagcgaa aagaaaggga tgctaacacc cctttattct taacgacgga acgggcgaga  95820
cgcgttttgg cgattgttgt aattcttatc aaattgtgcc aacgccgccg gactccattc  95880
gcgttcccat tctttgtcaa cttcggtttg gttggcaggt tcaatcattt cagcagtagg  95940
aaaatcgcgt ttcataattt cacgcaattg ttcagaaggg gcggtttggg cgtggactaa  96000
ttcttcaccg tcgtaaactt tggccatcaa ccatttgctg ccgtaacgga tatatgcatc  96060
```

```
gaggatgatt ttcataatgt agttcctgct tttcaagttg gtgtcgtact gcttatgttt  96120
agaattatac gtgggttatt gaagaagtaa aggggctttt gccccttttta ttgaataatt  96180
taaggtattg gattgacaac gggaatatgg aacctgatcc cagagacaat gtccttcagc  96240
tgaggcttcc agccgtccac caggcgggac aacgcgttag aaccaggata gacaataatg  96300
atgtcgcttc cggttacatt atgttgaggg aattgtgaca tgtattgctc catcgtcacc  96360
cctgggtcta tcaacacagg accgacatcc gaagatgcat atgttgcccc caaaccgtcg  96420
acgccccatg ctagtattcc ataatcagga atattggctt cagaagttat ggtgaatccg  96480
aagatacgat tcagcgcaga aaaatcatac acgccgtgag cactgtcata tgtcagataa  96540
ccctttgaca gcatatcagc gaatatcgcg tctgtgtcac cagttgccgg agtcggtatg  96600
gtaaacaata actcaccagc aggaggggat ggatacgtgc cgagtgcata aaggcaccaa  96660
gcgtcgatgc atttcttgat gaatgcttcc ggcgcgacat aatccgcaag gcgcattgta  96720
ccggaatatt ctgaagtaat gatcccttcc ttcgcgccct gaatggccag aaataccatt  96780
atgtgttcat atccggtctg agatggagtg atattcatta tctggtcctc ttgagtttct  96840
caatcgtgcg cttattcatg gcgatcactc ctgggtcgac ctttgggttt attgccatgc  96900
ctttgaaaga cacacatcgt tgaagatatt tagccttctt cacgacgtcg gctgcataag  96960
aattggattt ctggttacga ttgaacccag cattgtaaga ggaaagggat ttgcggatgt  97020
tttggttatg atattctaac cagaaattca tttcatcaag ggcagcattg gcagcatatt  97080
cttgattgac cagtaatttg atcgcgacat tggcgtaaca cttctgtgtt ttgcatccct  97140
cccgtttccc gacggtttgg acgcgatttt gaaatgcccc catattagcc gatttgaggt  97200
tattccgcat ggatacaaca tcttctccag cgcggctttc cctccatgat attgcggcga  97260
gagtgaaacc aaggtcttgt tgttttccca cgtgataggc tgtggccatg gttgaaagtt  97320
gttgatcaga aaactcataa tcacattggg tggtactttg ggaagcgtgc acactcccgc  97380
tggcaatggt aaaggtcacg gacaaggcca tggccttcaa cgttgtcatc gtcatgatgg  97440
cgttccttat gtgtttgtcg acttgcagct cgctggagcc tcctgacagg gttaaaagat  97500
aaagggcact tgatatttag tgcccttcac cttattcgta gatcagatgg tatgattcct  97560
cgatgcattc caaccaaccg tagacaaatt ccataggatc atcccaagct gtattggaag  97620
caatagtgaa atccccgtcc aagatttgca tgtcagtata tttgttgaaa cctaacacgg  97680
catcaacgac tattaagcca ccttgctcta gataacgctt tggggtcaac gtcacctgat  97740
aatgtttgtt tcgctgattc cataactcga cagcgatatc acaagcaatc tgaatttcat  97800
ctttctcttc tgacatatgt ttgtctcaaa tattcagtaa aagatttacc caacttgcgg  97860
aatagtttaa tacgaccgat cactttgaca taaacatctc catgacatgg acgcggctta  97920
caccagcatc ccaaggtctt tccgtctaat tcaaggagtt catcttcggt gatatcccct  97980
tcaatcaggc gcacatacaa gtcgtcttca aacaactcaa tacagtttcc ccgcccgtgg  98040
tctttaacct cgaacgggtt cccccatttg ccaggacgac caatgtagat atcgtatggt  98100
tccttcttga agtggacgac tttcattcca gttcttcatt gtcagagatt cttaccagaa  98160
acgcctggtc tctgtttgct tcaagatcaa cgaatcttcg acttccgata gcttcaattt  98220
tccaccaatc gaaagaacac caattcttga tgatacattt gatggctttt tgctgcatac  98280
tacaatgagc gcggcgatag cgttccttgt atttctttgt ccaaccgtgg ttgtccgcct  98340
tgtgatcata aataaacatc aggcgaatag ctttgtacag gcgcttttca gcgcccttag  98400
```

```
atttcttcga taccctgatc atgatatgca tgcgttaatc cttcttaatc acttcggtca  98460
tgccattacg cagaccataa cgaatgttgt gttggaaata ttcttggaac tcctgctcac  98520
gctgactgat gacaaacaga ttgttcccac caaatttatg tttcagcatc tcaaccgatt  98580
cttgtacgcc acgctcgctc atgttctcaa ggatttcatc taacacaaac aggttacatt  98640
gcaccgacgc cttgaggttg gccacgtccc gtagggctaa tgtcacagcc agattgagtc  98700
ggctgcgttg tcctgtagac agggagaata tgctttgccc tttacgacct gcagcgctca  98760
tggtgatttc aaatgtatca tcaaccgcaa tatccaagaa catattgagt gcttcaagat  98820
actcgtttat tttactattg aggaaaggca aatacaggct gataattcga gccttggtct  98880
gatcatcttt taggaagaac agaagatggt tcaggtcttg caatttctca tccaactcta  98940
cgcgccgcgc attcagatct tccattaatg ccgtgatgcg agcgatctct ccttccaggg  99000
cttcagttgg tgtcggctta accgccaatt tacgctctaa atcggcaatg gatgcctcta  99060
gaggggcacg gcgtgatttc aggctggtga gtttatcagc agtgtcattg atgcttttag  99120
agagctgctc acgggcttgg cgaatagaag ttgtgatatc ttcataacgg acatctactg  99180
ctctgaggat atcattaact ttagattgtt gttctcgctg taaagatgct ttctcaaccg  99240
ccgcaacttc gtagaacccc tggatatcgc gttttaaagc cgcgatggcg gtttctgctt  99300
cacgggcttc gttgcgtatg gattccaatt ctttgtcaac aacagaaact tgggaagata  99360
attctgaatc tttgacattg taattttcaa tgagtgagtt cacttcttct agggctgtat  99420
caacctgaag aatcttgtcc tgcaattcac tgatttgcgg ataatattga ctttcaatac  99480
gagacttggt gtcgtcagac actaattgtg tgcaagtcgg acaagtcccc atttcgtgaa  99540
aacgtttaat ggcagattca tggccttcca tttctgtgac gaatttgaaa cggaagttct  99600
ctccctgttg acgccgcgcc aacgctttat tcagttcgtc gagattagca ttcctctgac  99660
cgactagttc gtttttgtgt tctgcgacca ccgccattct ttcgcggatt tcttgtaacg  99720
acctttcgcc gtcggatact tctatgcgtt cataatcttc agccttggta tcggcttcat  99780
cctgaactgc ttggattttg gccgcatact cttcattgat ggcatcgata tccccttca   99840
tttcggcatt caggcgatta cggacttctg ataattctga ttccaattta gagtcttgag  99900
cacggaattc cgtcagttct tcttgagaag caccaatatc tgaattcaaa ctattcagac  99960
gttccttctc ttggacaagg atatccgcag attgttgctg gatcatcgca ttggaattat 100020
tgatctgttc caactgcgct tgctggcctt ttaaatttac atcatgaaag gcgtaatcat 100080
tggtgaccgt cgtgagttca ttcgttactg tcttgataga tgcttttaca tcttcattca 100140
tcaaactgaa gaaccctaaa tcccagattg tctctaccat agcgcgacgg tcggcagtgt 100200
acatttccgt gaatgggatg aacttctctt tgcctagaac cagggagttc tcaaacatct 100260
tctggtctac gccaatcagg ttcacgatat atttgttcat gtcagctttg gccgcatcat 100320
tcacgacctg cttccactca ccgtctacca tctgatagac ttctacgaaa tcaggtttga 100380
taccacgacg gactttccat tcacttcctc gagtggagaa ctcaacttca cccacgcatt 100440
cctttttgtt ttgggaattg actaatccgg ctttcttttc tttcttgctg tatgtgtcat 100500
tatacagaac gaagaataac aaccaaacaa gcattgtaga tttgcccgcc ccattgtcat 100560
cagatgtgac tagggttgca gggttgcgtt ggtaatcaat ttccatgaat tcattaccga 100620
tggaacggaa gtttttagcg cgaccgcgat ggaaagtcag tttgtgggta atttccccac 100680
ggatttcaaa tggtgcttca acagaaacag gagtgtccgc ttctttcaac agcgaaccga 100740
atttagacag tagatctaca ttgttcatta ttatgcatcc aatgtgttca aacgttgttg 100800
```

```
ggcagcatta taaaattgtt ctgcaagttt gcaaacattt tcagggcgct ggatattgtt 100860
ggctgcgcgg atatctttct tcaagacttc caccgcatca gtagccacca tctcttcagt 100920
gacttctacc ttctcggaag caacagtaat cgtccgatcg atgaagttgt aatcgatgca 100980
tttacagcgc ttcaatgcgt cacagaactt ttcataatgc ttggcattgt cacggttctg 101040
tacaatcacc ttaacgattt gcccttcaat acccaaacca ttgtttagcc aatctgggtc 101100
aatccagttt ccttcggtgt cggaagacat ttgggtgtag tcgtattcca cgaaccggaa 101160
caacgtttgt tgttcgttgt tggggataaa caattccccg ccattcatgt cgtctacata 101220
gaatcctcgg ttcgtcccgt ctttgtggtc ttcccaggta agatgataag gagtcccaat 101280
atactgaatg ttaccttcca tcgaacgggt atggaaatgt ccggtatcca cgcgctcgaa 101340
tttcgaaagg agcgccaagt cgatctgacc tttatcacat acagaggact ggtacatttt 101400
gaaccctgcc aactccagat gcgcaaaaca gtacttggcg tctgtatctt gtatcgcttt 101460
aatggacgca tcatagttct ctttgttaat ccacggcagt aggagggtct tgacaccttc 101520
aatcattact tcagttggtt cgctgtaata atgataaaca tctggtgcca attcattaag 101580
ataagaaggc cagttaatgc gattggactc ttctaacgtg atatcatgat tgccgacgat 101640
gccattccat ttaatacctg ctttgcgcag cgctggcgtc aattcatctt tcaaccaatc 101700
tttatcgcga ccatacatga atttgcgaac atcaaacgta tcaccaaatt gccacacttc 101760
tttaatatcg gcgtcaacca attctggaat aaaataattg atgagataat tctttatgaa 101820
ttctcgaacg taacgggaac cattacggct cccgatatgt aaatcgccta ttttagcaat 101880
cgccattatt ttgttgctcc cgttctaatg ctcgtttctt tgcttcttcc caatctggtt 101940
ccatagaaca tatttcgtct tccagattga attgagtaga gccgaagtca tagtctgaat 102000
tatcttcggc gtcggcggta atggtatttt cactctttgt gagacattga agtataccgc 102060
gaggaatttt cttattcttt tcctcttctt tgatggcgat ttgcttttgg cgttcctttt 102120
cgcgctgggc ttctttctta gtttcaaaat ttccgatacg ctcacggaag tccattgtta 102180
taccagtgct gtctacgaat gtctgttgct ggaagtctgg gtcatctgat aatgcagcga 102240
aaccacctgc ttcttcaaat gaacgcaact tgatataatt gtgttcttct tcactggtga 102300
gtttcttggc gaatgaacga tcggcgcaca tcgttaccca agagaagaaa ttgatttttc 102360
ctttcttgcc gatatgactg acgtcaaatg tatggaggta acgaaggatg ttgacaacgg 102420
cctcactgac catgtcttcg cggtatggat aatcacgata gttgtagcgc atactcatgt 102480
tcttaataat catctgaaca ttcatggcca cataattggg gattcttggt aggggtgttc 102540
cttcggccaa agccttttg cgagccggaa tccaatctct caatattcca acaacacggt 102600
cattatcttc gtctgtgaaa tatttggtga cgttatcacc cctgtctaca aaattcatac 102660
ccatcgtgat aatcctcaaa taccaatgaa ttcattgaaa gaaccaacga ctttcttgac 102720
cgagaaacgg ttattttcaa gaaccattga actatcttct ttggctctaa cgctccactg 102780
atccgcaatt tcgttgccca tcgttcctgc atgacctttc acccatttta attcaagttc 102840
acaaattgaa caaactttgt cataataatc gaacaactcg agcagaagtt ctgtgttctt 102900
aggcggcatt ccttcatatt cccatttacg acgccactcc aaaacgctat tgataacata 102960
ttggctgtcg gatataatgc gggctggggg aatgcagcgt tcaccgcaat tagagaattt 103020
ccataggatc ttcatcgcgt ttataacccc gagtaactca gctatattgt tcgttgacgg 103080
cgggggtaaa tacccataaa acactttcca ttgctctcca gtgattggac tgatggcaaa 103140
```

```
tgcccaacca gcggctcgtg tcttctgagg ggatgatgcc ccgtcagtgt atatttcaat 103200
catgtataag tatcccaaac tggttttatc gatgaggaac gaatcatgtc agaacgcgca 103260
tatcgtttca gtctgaccgc cccagaaatt gagcgtttgc tcttgtctat aaatgattcc 103320
atacaaaagc tggacatcat ttatgactac acggcgggtg ggactgaagg tcaagtcgca 103380
gctgcgtcag ctgtcaaaaa catgtggcta aaacttaatg agatggtcac aggtgaaggt 103440
cttaaagacg caatcaatgc agctaacgac agcaacgtat tcaccgatta ttataagtct 103500
attttagatc gcgaaacttg gaaatttatt ggttctccgg cagatttatt agcaagggac 103560
gatatagaca cttccaattt tgaaggcggt gaagtaatcc tcctacaaaa gaacgcttcg 103620
ggcaacccag aattccaata ctggaaaaga actcctgtgg taggaggtga tccaatattt 103680
ggttgggaat ctgtttatga aggaaactcc aacgactctt ctattgatat tccggttgtt 103740
gggaccagca tactgaagac catcccaaaa gcattgtttc atatggtcga attccgagta 103800
cacgctcgag agtctaccct cggtcattgg caggacactg atggcaaaat cggttatcgt 103860
ggtgaagatc tgatttatag cctgtataat catgttcaaa ccaaaccgat cgcaaatata 103920
tctttcagcc aagatgtgga caatatgatt atcacgataa cgacacttga accaaatatc 103980
aagtgccatt tatcgtttat tgcgggttat taaacctcaa acactgcatc ggtgaaccag 104040
gttgggaaga attctgggtt gcgcatcata agagattcaa aggatgaatc aatgatgtat 104100
gtcgcagccc agtcatcaac acccctgacc gaacgcccac acatttgaac aatgcgcagt 104160
actgcattgc ggaaatatgc cgacggatcc actgaattga tatgtgctat cagtggatcg 104220
cccagataat cataagggac tttgatcagt atttggaaac ggctgtaatc ccctttgaaa 104280
tcataacctt cttccatagc cggactggca atgacgcatg ggactttgt tctaaaagca 104340
ttttccataa tatccatcaa cgcctttcgg gtacgcggaa catggataaa attctgatat 104400
ttgctgaatt tttgtattgc caaggcgcga tcataactca ctgtatggat aatgccggac 104460
tgacctgggt ggaacgcgat tatttcatca atatattccg tcaacctttt catttcatag 104520
tcacccatat tgttagtcat cttcactatg ggcatatagt tgacttttct gttttcaatc 104580
gggatagggt tgccgatctg aatggaatga taatccccct gtcgaatacc caatgaacga 104640
gcatatgaat ctataccaca gatcgttgct gacatatgaa cgtgataatc ggcttttcgg 104700
aataacccga attcgcttac atcagaaggc ataacaggtt taaaccggat aaaatcttcc 104760
cccttatctt gcacaataaa tgtacttgct tgggtttgtg acataatacc gcaataatca 104820
ctcaagttat gcaagacatc tataatgtcg gcgagtttca tcacttggct ttcactcaag 104880
cgatcatctt cgaccaattc ttcaagaact tccaacaaat tttctacttt gagatggagg 104940
gcttcaaaca ttgaatgcag ttcaccagac aaagaatata acttgcccag gacatagtcc 105000
ttggtgcgtt ctacgatatc accaatggta gagacgatct ccttgccctc agggatagaa 105060
cgcagcccct ccacggcctt tgtattgtat tccatgatcg tgtgctctag gagcgtagag 105120
ggcattttat ggcactcgtc aaggatcagc atatcggaac ggttttcggg cttcatgcag 105180
atggttgtac acatttcgat catcatggca gcattagtac aacgcaatga tgaaatatcc 105240
gtccacaaat tacgcgcctg tacataagga cagcggcgtt tgctacaatg cccgtcacgg 105300
catgctatac ggcattggac agcattgtaa tacacatctg gatgtacgtg gcaacgatag 105360
ttcttcttgc cttttaggat gtctatcgcc accgcctttt cagcagcata ctgatcttgc 105420
agacctttgg tcggggtgct gatagaagtg cgaaattgcc cataaggatc agcctgtaaa 105480
accaaatggc gaatcacttt atgaatggta gtgccaatca aagatttacc gacacctgtc 105540
```

ggagcttcaa tgatgacatg tttaaccttt ttgttgataa gcgcatctat ggcttcgacg 105600
atgcattcca tctggcctgg gttcgctttg tcatatggga attcatcttt ggtaaggcgt 105660
tgtatttctt ccacaggaac cttacggcct atggcgtcaa tcgcctttcg gtgttgatta 105720
aatgctgtca cgttgttcct cctttggatt ctgttatagt ttacccgaat cccaacaacg 105780
aaaaagccga ggcattaacc tcggcttctc cttttagcct tgcgccgctg cactgcagac 105840
atgcgctggg ccgacgcctg gtgtgattac tggccgttgg cagcagcttt cagaccttca 105900
ccgactttga atttaactac atttttcgct tcgatctgga tctgttgtcc gttcagcggg 105960
ttgcggccag tgcgcgcttc ctgatgttta acttcgaacg cgccgaagcc tacgaattgg 106020
acagattggc cagccgcgac tgcagttttc acgccattga taaaagatgc aacgattttc 106080
tcagcttcgc ctttggtcat accctgggtt tgagcgatgt gagcgataaa atcagtacgg 106140
ttcattcgga ttactccagt tagttgttta cgatgtttca ctacaagagg actacagctt 106200
acctaacaaa tactattgaa taaagcgttt atttgccgac gtttagcatt ttacttgagc 106260
ctgaaccatc aacaatcaga gtacatttcc cgctgttggc gcaagattgc aacaccatgt 106320
tatattcgtg ttgtaaatat tcaggtgtca gagatgtcgt cagtttctga ttcgccctgg 106380
cttcttggtc tcgaatttca acgttctttc ttgctgtatc caaacgtttg tcggccatga 106440
cattatcacg gatagattgc tcaatcgaag gatctgtcag cgcctttttc accaacacac 106500
gtgtgattgt gaacatgcca ggcgcagcag tttccaattg ctgctgggtg cgttccttga 106560
tcatcttttc taactcagcc cgttgggtgt gaattgtcat agaatccaaa gaggaaacgg 106620
cgtccatcgt tgaggatgct gcggcggttt taaccaggtt gaatcccacc gctatcgtgc 106680
cgtcaccgag ttcagcgctc tgacctgcaa atttggtatg gaaccaagga accttcgcga 106740
cgttcggtgt gtaataaacg tccacatcca gatcttccaa ggtcaggttg tctttggcct 106800
ttggcgtcat tttcgtcaga ctcacaacgg cttctttggt cgtgtaaaca tccacgcttg 106860
aaacaaagct ggtgtagatc cccgctgtta cagggttcat gtccacttca ccccattggg 106920
ttcgaacacc gacgtttcct tcatcgataa caccgccgca gcctgaaaga aggcttgttg 106980
ctaggaccat aattgcgcca aataccagtt tcttgaacat caatgtactc cttcaaaaat 107040
gtaaatataa gcacccaacg tgagtgcagt tattgtaacc gaagaaatca gcagtaggaa 107100
agttactctc acccgtttgc gccaacgttt actccggtag attttagtct ctttcaagta 107160
tttgaaaaag aaaaataaaa tgaatgttgt tattacgaat atgaacagat aacggattaa 107220
cccgatcata tttcccaccc tgtgctacgc agatgatcaa aataatcgtt gagttcgtca 107280
atatcttcga tatcaaccca acgatcatcc agtcccatat catttagatc ttcttcagtc 107340
agatcatgtt ggtatatttg aacgccggaa gcattacaat aatccggctt gatgttattg 107400
ttatactgaa acaggtcgta atcggccaga gtattcttca gacgttgcgc ttcttcaaat 107460
gttggaacct caacatgaaa agcgatccca ggaacctggg gaatatgcca aacgcgaaat 107520
ttaagttcaa acggtttatt cgacatgggg ttctccctga gacagtatgg ttttcatctg 107580
ttcacgcgtg ataattgttt caacaagatt ctcgtcaatc atcatttcgt ttaacagatc 107640
acaacccagc acatgtggtc gtgccatata cggcatcgtg ttgagttttt cttcaatgtc 107700
aagaacgcgc ttgacagtca gacccatcga agaaaaaggg acaggataaa agaatgaaat 107760
gatctgatta tccatcccgt ttgaaaatct taccaacaat acatcacacc atacgccgga 107820
catattacac ctccagacgg ttacaatgag aaagcgcgtt atcaatctgt tcccgagaca 107880
gatattccaa cgggttgcga gaatacgcat ctaacagcag cagttggagc acagcgcgat 107940
tacgagtttc actctccatc atgatgccgt tcatatgtgg tgaacgggct gtccatacaa 108000
catactgacc taaatcgtcg ttggcagtca ggctaatgcg aaactgattg cacaatttgt 108060
cgattaacgc ataatcatat gtgaacgtcc cttcagtttt ccagcttgat ttcttcacct 108120
gaagagcttc accacgaatt ctgaattcta acgtcactcc atgagtttca ttgtcgaaat 108180
gaacaactct ctgagtttca tttttcagag tccggttcat attatatgcg aagaaacggg 108240
cgtcgatctc cctattgctc atggaattaa aatcgatcgg ccaaaatcgt gcacgcataa 108300
tcgcgccttc tggcaataca attagtccat tttcacggga gacatagcaa agacgtttaa 108360
ctgtagggtc aggatgttcc acacaataaa cggaaattcc agtgggaagg atagcgtggg 108420
cgacaacacc agatctttca aaatataaat taccctggtc agccccgatg ataatacggc 108480
tcttgttgtt cataatatag atctctcaaa taaaggcggt ttaataataa ccgcccttgt 108540
attatagaat tattttatat caccgacata catgttcaaa ctttcatccc attctaaacg 108600
aacacgaata gtgccagaat cgtttgggaa agacaatttg tcgcacatat gacgatttgc 108660
atatgttccg ctcttattaa caggataatc tttaccttca ccgattgcga atcgtttgaa 108720
gttccgactc accatcatat tgatgttagt ccactgcaat tgttcccgta gggttttaca 108780
caatataatc ttcccattag accggaaaga cacgaataaa tcatttggtg aagaaaatcg 108840
tctttcttgc gggcataact gcctgattga aataaattca gattcttctt tattctcaac 108900
cggagacttc acgggttctt cttttcgttt ttctgcatat tgctcaacag ccttttggct 108960
gacaggcggc agatcaatag aaggggagat gactgctggc ttaatgactg gtgaagtacg 109020
agcagcaaca agtttttcct gagcttccag aattctctct tggcgagatt ttggtcgagt 109080
atcaaccttg gagctgaaat cacaaaccgt aacccagtca ccctggtcgt tgcgcttggc 109140
aaccagagtt aatttgtaaa tgatgccctg tagcttgctt tcacgcatcg tgtctgcaaa 109200
ccagaaagcg caccccttgct caaatttttc agcgaagacc acgcgaccat catcatggat 109260
cagaataacc tttgctttgt taggtgcgaa cattttattc ttttcaacga tcgcctcagc 109320
gatctttttg gtaatgatca tcacgaaata cacctttcag ttcaatgggg aataaaattt 109380
taacctgaaa ctatctttga tttccaacga aattagttgc aatttcacga cacatcgtca 109440
gatctttaat agtctgtttg ctgttgtctg cggcagattc catcatgggt aaatcaagcg 109500
cattctctat ctggtccaca ctatagagat caaggcgttt caattcacct tcataatcag 109560
ataaaaggat tgatgtgtcc ttatcatctg gatgaaattg ttgatatgta gacaaccaag 109620
cagcacaaat attcaactta ctggccggag ctgccaatac ttgggaagac atgaaagtgc 109680
acaggaataa caagaatatt atgtttctca tctttcgttc tccttcatca tattatcaca 109740
gtcaattctt gtttgcttga gttcacgggc aagcctggga tcatcaagat tgacagacaa 109800
attagtggaa agatctttca aaccattctg aacacggtct tcataataat gatcattttc 109860
caccagccat gctctcaggc caagggcgcg agtccgccat tcctttttca aacgtcgatc 109920
tgattcttga tcagcactgt attcaaatac tcggatacat tggttgccat cattgatgag 109980
atccagctga cgtcggccaa cctgcacacc tttttgtaat gctggagaag gaagagaacg 110040
gcactgtctt acggtcattc gtccttgtgt gcccatacga ccagtcatga tgagatcgcc 110100
agcctccatg cctcctcggt taaattcttc gtcgttcata tatcctttca ggttgaacgc 110160
gccttgctta tatcgattaa actcaatacc agcatttaca acggcatctg tgacattacc 110220
tgtggcccag agttcagcaa agttctctat ggaaccagtt ttgtctatag cgacggcttg 110280

```
ggagaaccca gcacagtagg aaagatcaga ccacagtttt tcacccgtgg aattcagctt 110340
ggcggtggca ggaagtgcca gaccagccag cacaaccccg atgattaaac gtttcatggt 110400
gattctcctt atttcattgg ataaaatgat agggctgtca ccatgttgag taaagggttt 110460
caataaacta tcgtattcag aaacgggtat cgctgaccgt tctgtatcgc acaccctgaa 110520
actgtttagc gagtttaaca aattccatcg ctggcaaatc aactttgtag accttcatgc 110580
gctgtttgcc gtccatgttc aacgcagcga caaatcggtg agacccgtca acaacgtaat 110640
tgtcagaaga cacccaaact cgacccatgg gcttcttatt tctgatctgc ttcataatct 110700
tccagacctt cattttattg atttcgttct gggtaagacg aagcattttg atgggcactt 110760
gcgcagcatc tatggacacg ccgttgtctt caagatattt gtgaaaatct tcttgtttgt 110820
cggcatcgat ttgcggcata gaagaacgag aaagcccgag gttcccaaca ggaatcctca 110880
ggccatttat gatattcatc cagtcaataa aggatgtaag gaacatgaca cacctcggga 110940
tataggatta tcccttagtt agttcattcg gacttaaaca gcaattcgcg aacagaattc 111000
ccaacgttat tctgggcgtt caacaaacga gttaaatcat ccatgtcgta tgctgaattg 111060
gtgacatggc ccaagataat cgccaacatt ccctccagcg ctctccgatt gttattctct 111120
tcaatgtcaa acttaatttc aacaaatcga gatagcattc tggattgagc atgagtttcg 111180
ttggttttgc tctgtataat atctttgatt tccgaacgag caatacttct ttgatctgtc 111240
atgatatagt tccttcattt caaatgggcg gggcaaagat accccgccgt gggtttatag 111300
ggtaacaagt gatacggtaa aaaccatcgt cccatctgtt gccatttttc ttgaaactgg 111360
gaagacgcga ggctgacaga atatccattc tttctccatg gacgccaagt ccagcatatc 111420
catttctgat tcatcgcctt tgttcacaaa tttttctaga gaaccaaaga cattaagccc 111480
ctctgggagt ccgtttcgat gtttataaca aatgcgggca acagctttgg ttccatacga 111540
tttagaaaat tgtttggcca catgcttcag ttcgctgaaa ctaagacaag aatcccatgt 111600
ctgaaacatg tctcctcgtt caaacatcat ctccaaacgc gcaacgtcct ctttaggcaa 111660
cccgcgataa agtgtggtca tctgcggttc gcgtaattct tgcaccagac cacggatggc 111720
aggggaaaca gtgccagggc gcatgatgtg ggacttatca tggacgaggt aaaataaatc 111780
ttgaatttgt tgatcggtca tgatgtattt ccttcatttc aaataggcgg ggtaatcata 111840
ccccacccta agttatagaa ttaactgatg tgcttcagaa gagcgaagag gatcgcggcc 111900
ttggctttca cctttccgac gacgcctgtt tcgacatcga cttcttcggc aacccaatct 111960
tttcccttct tgctgatgat aacatcgcgg cgctgggcat atacttcttt ggtcgcatac 112020
acacgacgga accctttagc gcggagcaag ccccaattac gatcaatctc cactgaagtt 112080
tctaccattt tgttcttcat gatataatct tacctttcaa cctggtgaac ccatcgttcg 112140
ccagttattg aataatacgc atttgcctta tagaagtaaa cccctaaaag taaaaatccc 112200
caacgtttgt tggggattta ataaaagtta tgcctgttta atttctcggc ttgaattttc 112260
cagttctaat tttcttatag cggaaattct accttcatca gttgcgggaa actcccaaac 112320
agcacgacgt ccgttgtggg tatcacaact tgccagccag cagaaattag agggatcttt 112380
aaacaatacc aatttagggt tagcaatatt gttcaggcaa aatggggtga ggtcaacaac 112440
gcgtgataca gcagacataa tatatacctt ctttcaatga acgggaacgc cccgcccgat 112500
gaattcaata atacgcattt gccttataga agtaaacccc taaaagtaaa aatccccaac 112560
aaacgttggg gatcttcagt tacttgcgca gggcaacgac gagttcagct aactctccga 112620
```

```
gggtaggatc atctccatgt ttacccaccc actcgtcact aatttctaca tcgtactctt 112680
cttcgatttc catgaccagc tcaatcatgt caagatcgtc accgccgaga tcattcttaa 112740
cccgtaacgg cgctaaagca tcgatattat catcaatgtt atcaaacttg tccttgtgat 112800
ccccgttgcg ccaagtttcc atgttcaggt tgtcacaagc gtactgagcc agaacacgca 112860
ttacttcaac ataagttggt ttgtttgaca taagcatatc tcaaaatgaa ggcgggtttc 112920
cccgccagtt gaatttagat tttgacttct ttttcagcca gttcggcagt gacagtgtat 112980
ttcaccccat caacttccac atccatagtg gattcttcca aatccaggtc ggtaaaccaa 113040
ccatggcctg caacaatccc ataaactacc ttggacagcg ttttgttcag agatcgaact 113100
tcgttgatag ctgcttttgc tgcatcacca atccaacttt cgatcagctt tttctgagtc 113160
tcttccggta cgctggtgat catcggcgat ttaacaaacg cattgtattc ggccagggca 113220
ttagcgatca gctgatcagc gacattcagt tttttaccgt ccgtctgttt tttgataaca 113280
gacgcgatgc tcggcagtga agatgcgcct ttgattttca cattcaattc acgactcata 113340
tagacatcgg ttgattctac agaagaagtc ttcggtgaaa atccatagtc gcgaatgccg 113400
tttgctgaca ggaaatcagc cgcttctttg ccatattttg aagccagacc agtagcgttg 113460
cctttgccaa ccagttcatc acggtagaat ttcagaactt tttgctttgc cttcaatgct 113520
tcacggcgca cattgtctgc aaagaattca gcagcactga tattctttgt catggcgcgg 113580
ttaaccattg ggacactttc cagatttaca ataaagactt ccggcccacc aaacacatga 113640
acacccatgg cagtcaaatc ctgtgccacc ttagcccgaa caatcggaga atctgcagtg 113700
ataggcattg ttttcaggtt gatgatacca tccttgacaa tggtgtaatt gcgataacgc 113760
caggttccca gctcttcagg aagttcatat ttcttctgta caaactcagg cacaataacc 113820
gttccgtgtt gaactgtctg cacactgatg ttaggacgtt ctgaattata gaccaaattg 113880
ctgatcggga caatcccttt atcatctgct ggattgaatt ccggcgtcca atcttcgtgc 113940
tcggccagtt tgagcgccag ggctttacgc tcttctttag aagtcgcatt cgcaatctct 114000
tcggccaact tgtcttcggt gtcgtcaact ttttgtatag taccgcgccc aatgctcttg 114060
taagagaata gcggatgctt ggtgacgata gagacatctg cttcagccaa atacgtcaga 114120
acatcaacaa tggtggtggc gtcttcagcc ggaaccatat tgtaatcgat gccatctacg 114180
ccgcgcagag tttcatccac gatagcctgg gtcagatcga ctttgatgtt ggaatagtcc 114240
tgcttggtga aacagttgct gtattgtttg atgaaacgaa catctcccgt tttcttcagc 114300
gcagcccaaa ccaaatctgc gtccatggta tacacgccgt aaaatgccag cacgtatgcc 114360
gcttggatgt ctgccagatt atccagctgg tcgatcatgt tggggtttac aacccacagc 114420
tgagaaacgc tttcagggat gctgacgtga ccaatagggt gctcttcatc aggatgcacg 114480
gctaaaacag tcgccacgcc attttcaaca taaatggcat gggtgtaaac caggggaaca 114540
tcgaccacca ctttcggtga agaagttttt agcacgtttt ccaattcggt ctgatattca 114600
ttctggcctt cagcgaatac gtgggtcgca ccagaacgtt ctgccattag cgccagcagt 114660
tcgcgattac aataccaacc gtattcgatg aaggtaatgt tatcaaacgc tttgggcagt 114720
acttcaacgg catccaggat ttcattagaa cgccagcagt tgtcatatcc gtcggtcatg 114780
aatgccaggt tattaacata accaggttta ttcaagctaa tggcagtttc agcagccaat 114840
ttcagcggct caacaaaacc agtacaacca gaaggcttca ggaaacggtc aattagatta 114900
ttgatctcac tgagatcagt tgcactgtta atctgacgtc cggcaaatac cgttccgaaa 114960
tcaccgcgag atgaaaagta aaggatgctc acagtatctt ccggtttcac cagggaaggc 115020
```

```
aggttctcct tcagatgctt acggacttct ggaagtgaac gatacatgga accggagata 115080
tccacaacga ttacatggtt agacggcgcg acggtcgcaa ccgcattctt aaatgttaat 115140
gattcaatca tcgttattac cttctttagt ggtatggacg gcttcacctt ccggcttcac 115200
cagcatgtgt tctatgaatt cgcgattagt ttcaatctgt tggattaaaa cttcgctggg 115260
tttaaactgt gagtcaagag agtcaactcc tgaacgcaaa aatggtttgg tcatatcaat 115320
tttcattttt acggacatga tttcctcgct ttacaattag accattatac cttggcttgt 115380
taattgaaac gcccagcaat ttgccggacg ttattgattt tgaaagactt ttgaaaatca 115440
caagtatgac accacgatgg ctctatacag cgcccccacg gaatcatcag gttcggcttt 115500
cggatctaac aagaatttct taacacgatc acaagctgct tggcgtttgt cttctgatag 115560
gtcacaccac ggataatccc ctgaagcagc attacacgtt ttcgccaaac gcaagacaag 115620
ttcagaattt agttcttcag aagtcatgaa cgagcgaaga tacgcttcca ccaaagatct 115680
tgcttcacca ttacgtcgtt cgttataacg ttcattatcg gtgcgaacaa attcaactcg 115740
aaatccccga cttggatcct tgggatgacg aaacacgacg gattgtcctt tacccttaag 115800
gaattcagaa ccacccatct catgtatcgc ttccctttct gacacatatt catcaatgtt 115860
gatcttagca tctttgacgg acacatcgat gatctgcttt tctaccatcg cgcgatatgc 115920
ttccagttcc cacagctggg agaaggtctt ttcataggcc agtttcttac ccaactcttc 115980
atcaaagttg gctgggtcga tagaagttga actattcttc ccccagacga cgaagccatt 116040
gtccatcttg aagtggcatg taatgacacg atggccaccg acttcacggt cttcataaat 116100
cacttcggcg atgtgagact ttagaagttc tggtgtgagt ttaatccctt cacgattacc 116160
cattatccac ccccactttc accaaacgat ccagtaattg gtaaatcttg cggggacaac 116220
gccttaaatc ttcatccgac agatatagca cttcggtctg aatatcttta aaagttgaaa 116280
ggttattcaa ctcagattcg acgacggttt tcaattgcgt atacgcttca tcgcaataat 116340
ttcggcggtt gcagtcggtc attacctgag ataacttttc aaaagattct tgtatttcct 116400
ttgacatcgt ttgacaccta tagttggtta cacacagata ttactttacg gcacgtgtcg 116460
atatcgaaca agccgatatg gcaatcgcgc ttcttgatcc ccagattatg agccagccag 116520
ctgtaagcat cactcctgct cctctgccca cttttccaga tagggtcaaa agacctatga 116580
gcttcctgct tagcagcacg gagagcggca ttcgccatcc ttcccatagg ggtctttcca 116640
tcaccatgtt tatggcaacc gactcgggcg tcacatggag tgcacaccca gaacttcaga 116700
ttgcggagtt cagggcggtg ggggtataca acatcacccc cgacgtattt ggcaggaagg 116760
ccgcagtaat cacagatgac aggtttcatt aaccccatat ctctttcttt tctacccagc 116820
ctttaccacc acaataatga caagtcgtca tatcacgccc gtcgccagac ggagagtcgc 116880
gacctttgcc atcacaagaa gggcatacct tgcgaatacc ggacttcatc ttctcataat 116940
gttcggcctg accaagagta tcgaacactc tgccgtcatc cgtttgatat tgggtgattt 117000
gtactgtctt agtaatttgt ttcataatat ttctccaaaa gaaaccccgc acaaggcggg 117060
gttgctcagg ccggagccga cagattattt caacagcgct tccagttctt caacagattt 117120
accttcaagc tcctgctgtt tcttacgctg gatcagttcc agaataacct ggttgttcgc 117180
tttacgttcg gcggcggttg cgctttcgtc acgttctttc agtttgacac cgatgatcgc 117240
tttcacgata tcgaaacgca gttgtaactg agagtcgact gcgcttttca cgccgatgaa 117300
atcttcttca tcgctggcgg cttccttcac ctgacggctg aggtctttcg ccagttcgtt 117360
```

```
tagggcattc aggttcagat cccaaacctg ctcaacagac agcagacctt tgttagagtt 117420
gaaacgcagt tttaaacggg ttgcttgatc aaacatttca ttgttcctta ttacgaattt 117480
gtggtcaaaa tcaattagaa aatgactttt acagtacggt taaacgcgcc ggacactttg 117540
acgaacacgt ggttgcgttg cgtcgtcgag aatcccagac cggacagttg gttttcattc 117600
ggctggactt tcattttact acccaacatt tcaaaaacct tacgatgttt atccagttcc 117660
ggcttcagat attcgttgta gaaaccacga gtaccttcag gattagcaca accttccagg 117720
atgaagaaca cgtgcttgtt gcctgtctgc tcgccatccc aatggtttgg tgaattcagg 117780
accagctgta ctttctggaa ggtcgcagtc ttgatacccc aaacttcttt agacttatca 117840
acattagcca gttcggactt aatgccaaca acttgtttgt ctttaacagt caggatgact 117900
gcagtgatac gcccctgatc tttcaggcca ggatggctga aacgatgcgt tgcgcctttg 117960
tattctactt cgacttcaaa cccttcgtcg attttttcac gttgattgta gttgtggatt 118020
tcgaaacggt attcaccatc gcgcagcttg ctttcatctg taaagatgat attttccacc 118080
ggagcgcggt ttggatcaat accatccata ccgttcatat cgatatccag atgggcacct 118140
gtcatagagc ggcgatcgcg gaagtaaacg tgctccatgt tgttgaacat atgcagatcg 118200
aggtcgtcgt tattgtgcca cgccaaggaa acgcgcagat acccgtcaac tttaccgcca 118260
gcagccttta cacgttcttt aatggaatcg gtcacttcac cgttgtaaga ccaggagaaa 118320
ccgttgttcc acttgaacag gttaggcgca tctgggttcg ccggagcaac cagggacatc 118380
aggttgctag tatgagaatt ctctacaagc acttccattg aatgcgcttt tggcagaaca 118440
ttgctcagga aatcatcaac gctgatctct tcaacttttt ccagggattt ggtcggagtt 118500
ttcacttcgg cagccagctg agcaaacgga tccatcgctt tctgagcagc cagatctgcg 118560
aacagaacgt tgttgattgt cagatcatca taaaccgcat aacgacgcgc cagtgagtct 118620
tccaaaccca gagcaataac ttctttctga gcgttttcga tcatggattt tgaaaccagc 118680
gctgtcggac gtttgtagtt cgccggagca actttggatt caaacgattt aacagccttt 118740
tccagttcca cgccttcgct gatatctgtc agcagagtgc cgataactgt gttgcggatg 118800
ccgtgtggaa catgattgtt tgaacggtat ccagtatgcc atgcccaaag agaacgggct 118860
gattcgggga cttgttcata tgccttttttg gtttcaacaa atcccttcac tgccgctttg 118920
tgttctgcgc cgcgatacag agaattctgg tcaatcagtt ccagaacgat ttcagctgat 118980
tccagagtaa tttcacgcag accgcgttca aacaattcaa tagcctggcg gatttcacct 119040
tttttcgaag cgattgcgtc cggacgcaga acatagctac ccagcaggtc ggtgtgaaag 119100
tggttgtagg tgcggacatt gccgtctttc atttcgtgat tcgactcaac accgactttc 119160
ttggtatcgt taaaataaac atcgacgatt gcgtgttgtt tgacatacgc cgacagcgcc 119220
gcagcgacaa catcgtattc gttacccaac tgaataccgt cccagatgga aattacgttc 119280
aggtcggagt cgatggtgac cacaccgccg atgttacgga tgaattgttt acagcaggtg 119340
caatcgtgtt cagtacgttc gcggtacagc gggttagtac cagcagggaa agatgccaga 119400
tacagatccc aaagagcatc tttatcgata ttggtcatga acagaccagt tgcggacatc 119460
gccagcacgt tgttattaac tgccgttgcg aagggtttga attctgccat ggtatagtct 119520
tcctgtttca gttcaaatgt gctccccgtt tgccagggcg cttcgtttaa gtgaggtcaa 119580
taatacggtg aaaagagtta ttgaagaatg aagtaaaggg aatctttatt caggtttctt 119640
caaacggtcg aggagattga cagagctgcg actgagcaca acttcatcac agcgcttctt 119700
gtaggcacca cttccatcat agccgacctt gccccgaggt ttttcaccgc gcccgactgc 119760
```

```
ctcaacacag cgagtgtact tgctcagttc acagaacatg ttctccagct gcatgacgtt 119820
catgcattgg tctacaggct cttcggccga ccagaattgc tcgcgaacat acccatattg 119880
ggagtatacc gcgtcctgat tatcccgcag ccagaagatg cattcttcat gcgtcatgcc 119940
gtctttgttc aggaacagca gatcaatacc tgcgcgacag cctggtccag caatcgtgaa 120000
gtgattctcg ctgaacggat aaccaggcat gtacgtgaaa tcaacccaga tctgatatgc 120060
caggaatggg ccaagccctt ctatgtcgtc atacatgcgc tggtatactt ccagaggagt 120120
accaaggcgc agcaggtcat ggaagtaatt tggatacttg ttgacgaatg ccttcaggga 120180
gcggatgaca cgcattggca tgtacggttc ccaaccttcg atggtataga agtccggctc 120240
tgcttcggct atcgccttgg cttctttata atccatgttc tgggttgaac cgtctttaca 120300
gatcagattc accatcatcc caccgaagcg ctgctctttg tggttgacaa ccagctcagg 120360
gaaagccagg cattgcttca ggccgcctgt gttgaaggca ttggtgaata ccttaccgcc 120420
gtcagcctcg aacttctgaa gtcgttcgcg ggttgcgtca aggttgatct tggcgaattc 120480
tttgatcgtc atcgcgccgc cgatagcctg aattgggtcc cagaggttga acatgcggaa 120540
cagcacgcag ttaaacatct tgtctgccat gcccagagca tcgttcttga cgatgttatt 120600
gatcaggttg agggactgcc tgtcgtgctc tctccggacg ttacagaact tgacctgccg 120660
tagtatagga ttattcgtcc aaggagcagg aagacgctgc acatccttct tgacgtggat 120720
cttatagcgc tcgctcatcc agtcgtaaga caggcgggta tgggtcggac tgagaaccgg 120780
tttggccgac tttatctttt cttcacggac accgcagtac gggacgtcca gggctttatc 120840
tttcatggta tcctcttaga atacgaaaaa cagaggccat tatagcctct gttgtttagt 120900
gaataactgt atatcttaat cgatacgggt cagctgggtg atagatgatt gcactgggct 120960
ggccacatag atacggacgt tggctttcca ttcaccccag atcaacggca gagttgggaa 121020
gttgtcttca ttgaaaacaa acacaggaat ataactctcg actgtttcgc cagagaacgc 121080
ctggaagccc atcttggtgt atcccacgat ctcgtcaata aaatcgaacg gagcgaaggc 121140
aacaccagcg tgttcgttag aaccgagtcg acctggggtg gccgtgcccg tcagaatgat 121200
ttcggtgatc tggcgcttag gctcggtggt caacatatca gagaagtctg gctctttgaa 121260
ggttgccatg ttcttcagga acttgccagc cgggtattct ttgccgtcga ccgtgatggt 121320
gtctaccact ttgatgcacg cctgagggaa ttccccttcg atgcgtagac tttcgcgtgg 121380
gaagcctttg ttgtagtagt aatccagtgc aggcacaact tcaccttcat tacggatgaa 121440
cttgctcatg ttggaagcaa agacgcgctg taggcattca tcaccgtcga aaccggcaat 121500
atgagctacg ccgtcgttga ctgtggtgat atcaccctgc gcatccatga tggctttcat 121560
cagatcttca gtagttgtcg gcgtttcact ttcccgagga ttaagttcca atgtcagaac 121620
tacttgatga tcgaaatacg ccgcttccag gagttcgcgg gtttcttcca gaacgagttt 121680
cgcctgattg cgaattttgc taaagtcggg ggcggttacg tcccctttag cattaccaaa 121740
agccagattc agtctcacgt tcttactaaa tgtagttgtc ataatatagc gactccagtt 121800
attcgctttt tgcccgactt gggcgaatgg tgtattttgg aaccaatttc cactcagaaa 121860
cttggtcatg ttttacaact ttgatccgag acatgtcagc cacttcggtt atttgttccg 121920
gatgcaagat cttaaccata ttccattgct ccagaagccg tataatccga ttcatacgca 121980
ggacatcttc acgcgtaaag ccgttatagt gcccatctag catgaacaaa tgcttgaaat 122040
gcacgatgtg atatctgcca aatttatgca ggatatgaca cgtttgatac aaggtgttag 122100
```

```
gctcttgacg agtgttaacc cctatccgac tcagcgtttc cttgataccc aggaaaatcc 122160
ctggtttgtc ttggttcaat tgaacttcaa ccatacagtc aacaatgctg gcctcatcgt 122220
tgacagctga aagttttaag atgtccagcg tattacgcgc catgactcat accccttttaa 122280
caattatttg aattacttag ccttgcgcgg tttggctttt tcgttgctgt tggaacgttc 122340
gaccttcgcc ttgatttcag ccaggacttc tttcggcagg aatcgaacat attctgaagc 122400
cttttcagga ctgatgtaat aatactcaga aatcaatttc acatcaggat ccatagctcc 122460
cttcttagac cacttgtcat agcgacgttt tgccggaatg ctatgaaacg ccaggttcca 122520
ttgcatccaa ggagtaatgg catggaagcg gttcatttgt tcggcaacca caagcgtgtc 122580
tttactctga gcaaggccgc gccgagtcat gaaaggatca aatgcctttc tgatttcggg 122640
gtcttcggtc atcaacagat tctctttggt gctattcaac gcaccgaggt aatcgaacag 122700
tgacggagcg gccataatat tacttccatt tgatgttgag catgacgtta gtcaagaagt 122760
aaacgccgtg taaccagacg tcgccgacgg aacgatgttc aatctgagac tgaccacaga 122820
cgcataccag atcagggatt gactcgtttt gaatcaaagg agtcttttcc ttgttctggg 122880
gaacgcagaa atggaagaaa cgggaataaa aatcttcagt gatgtagttt tggttgtcgg 122940
tcacccactg cttcatccca gcccaatcat tggtttttag gaaatccacc aacgcttgga 123000
attcccctgc tttaacctgt gccagagcgc gttcatcgat tttaccaaac gtggtggcat 123060
tatcctgaag agttcccata attttgcgat tatctgggaa atatgatttc acaatggaag 123120
caattacacc agcttcatac ggaatgcctt cctctgtcag gatagttgcg caacgacgca 123180
tgaattgaag tttaacttca tctgcttcct tttcagacca gataaaatca atttcgcgac 123240
agcgggaacg cagaggttcg ttaacgcgct gtttcgcatt agtcgtcagg atgaaggagc 123300
agtttttgga gactttctct acgatgcctt tcagggattc ctgtgccgcc atagaaagtc 123360
gctcaacttc atcaaggata acgactttac ggccaccgaa aacactgacg ccagttgcgt 123420
attgaataac acggtcacgg atgacatcaa tgctgttatc cagtgacgca ttgatcatca 123480
acggtttgat acaaccgatt tcgttgcaaa cagccagagc agaagtagtc ttgcccgtac 123540
caggctgagg ggaatagaac agcattgagg ggatgtttcc attgcctgat gtaacatagc 123600
catggatttt tgcacggacg tctgaaggga ggacgatctc atccagattg tcagggcgat 123660
atttgttttc ccacgcgtat tgatctgtga cgatagtgat gttagacatt gcagcctctt 123720
tagataaaac gtttcaaagg gcggggaaac ccccgccacc gataataaag cgccgaatcg 123780
ttattgatta atccagctgc atgccgacgt aatagttgat ggtgccgtct gcggattgga 123840
agttaaccag ttgcatttcg gcacaggcgc ggatcacgta gttgccttcg atcattttca 123900
ggttgaccac atcaacaggc atagcaaaat cacccagagt tgtttcaccc aactcaacag 123960
tgtaatcgtt ggaattgtcg atagtagtgg tcgtgcccac cagacgagtt ttaccgccgc 124020
tggccaccag gcgtacagtt ttgtggccca gagtagaaca ggcgcgagtc agctctttca 124080
ttttttcagg agtgactgtt gcttcaaatt ctacagacgg aagatcgatg ctgtctgctg 124140
gaacgacagt cagttcttta gcggaacgcc agaattgcag ttgggagttt tcacctttca 124200
gcaaaatgtg gtcttccgac atttcaattt taccgccttt aaaactcggc agacgctgga 124260
ttgccagcaa tttggtcaga tccagaatcg ggaattcgaa cgggaagtct tcgtcaatgt 124320
cggcaatagc gataactgta ctggaatcgt taacagtgcg caacttttta ccaggtgcca 124380
gaacgataga ggggcagatg gtttcaaagt tagccagcag ttgtaaagtg cgttcggaga 124440
gagtgatctc ttgcattagt tgtatcctca aaatatagtg gggttcaagt catatttgac 124500
```

```
gcaaattagt atcgcgtgtt tgtagttata gaacaagtga taaattgccc tacgcgcgat 124560
aaataaatgc ctgacggcat ttataatatt ctgttttaat aaaacctttc tttatcagtc 124620
tactcgcttc gctcgtgata atactcgttg ctcgcaaagc tcacaactcg tatattacgc 124680
acggattgtt caacaagaaa gcgattttta ttcaacaagt aaaatatttt atttggtcta 124740
aacagagcat gacattatta tgtagtcaag tttgctaaca cgtgagaaat aatatatgaa 124800
gcaatttgtt ggtttatacg cagtagggga agaccaagaa gcaattcttt ccatagcaga 124860
acaacgtccg tcattaaaag gcgtttattt acaaagcctt ttctgtacat cggggtttat 124920
tgtgtcaccg atgttggtga taccattact cccaaataac aaaggtctgt atgttggcat 124980
tattcaacaa ggccaggcgc gggaagtgaa agttgttcca ttgctggcat ctaatgaaga 125040
attgttttct cagattcttg agccgaaagt gctacaacaa tgtattggca cgatcgactg 125100
tttatttggt tccaacaaag aaggcgaggc aacccccgcc tatgtgaacc aagatctttg 125160
aaatagttag agcgccactt ttttcatttt aacagggtgg cgctccataa gataaaattt 125220
atatctctca tgagaatgcc tgagagcatg gttgtaggaa ccgttgtagc gcaggttgtc 125280
taccaggtcc caaattcgcg caacatcctt agaggaatgc tgacgcatca aacgccccaa 125340
tgtctgtata acacggatat aagatttgct gggatgggcc aatatcagat gatggagttt 125400
tttgatagat acgccctgtt gcatagtacc atatgatgct aacagtgtta tatcttcccc 125460
ttcttccata gcagcctgaa tctgtttacg aacttctgtc ttgacttccc cattgatgac 125520
gaatacgttt ttcttgactg ccgatagcat ttcataaacc aacatcatgt gtgcatcgat 125580
acgttcgaac atgaccgcca cgttcccttt caaagacaga gccattcggg ctatcaattc 125640
attgcggcgt tcgttagcaa tgagaaattc tatttccttt tgatactcag caccgtgcat 125700
ttcaatacag tctgccatag gatgtatgac ttcaatcata ttaacattga tgtctgccgc 125760
atatcctaga tcgattaaat cgcgcgctgt aataatttta tgatatgcgc caaagtgagc 125820
aacgacttgt aaccctgcga cctttgtatt cgccagggtt ccggttactc ccaaacgttg 125880
atcagcgtta atacagttgt tcaagatgta agacaattta tctgattttg atgtatgtac 125940
ttcgtcgacg acgatatctc caaattgatg gaaccactct ttgggttggt tctggatacc 126000
ttgccaagtt gaaataacta tgggtttgaa aatctctttc gttgcccctt cgtatattgt 126060
ctggacattc atcaatggct tccattctgt cccgtggcta tattcttcga agttgtcata 126120
caactgagtc accaaatgaa tggatggtac aacgattaac gtcctcagat tactttcgag 126180
ggcatctctg cgttgcctgt agtaacgcgc catgatgtac aaaataaagg atttgccagc 126240
actcgtggca gcttcgagga cacatctgct ttggcgtatt gctgtggcaa cggaatcaaa 126300
ttgatattcg cggacaatcg ctttttgata ttgtttgttt tcgtctcggt acactgcatt 126360
caatgtatcg atgaacgcat gaatttcttc atccggaata tcttgaatat attttaaggc 126420
cggatctaat ttgatggtgt aaccgttcat cttacagaat ttgaacacct caaataacag 126480
gccgatgtcg ataagcccag aactctttgt gaacagccgc actacgccgt cccatttact 126540
gaacggattc ggttggaaat taggatcttc aaatttgaag taatcgttga gttcttcacg 126600
gatataatcc tcggcaagga tccgcattct aacttcgttc actttgacta tttggatctc 126660
agacatcact aatttccccc aatattatgg agtatttagc gatccaccca gattccgttc 126720
tgttctttat ccattttgtg atacagacgg acacggtcaa acattttaga aataacgtct 126780
ttgcgatcga attcgattat ggtgggaaca agggcatttt cgttggatat aatattgatt 126840
```

```
aaacgctcta tcttgacatt aaacatttgt tgaaacatga ctgagtatag acacaattga 126900
atactataat cttctatcat gcttcgagtt tttagggtgt tagatgtttt gaaatcgatt 126960
atgcttggaa ttccttcgta aaccccgatg aggtcaacac gaccagcaag acccaggact 127020
tcgctatata atggaatctc ttgtgcatat atcttgctca ttttgttaag gtaggggaaa 127080
acctgtttga acataaacac gtattcccct gcagcttcca gaacttcctt cattggtctg 127140
tttttgagat acaactcaca agccaaatga agtttttccc cacggtctgc acaacgatgt 127200
gtttctatat cagcagcttc atgccccaac ttgtcccgcc aggcttctaa ccatgtgtgg 127260
tcaccagtac gccctaacat ggtcgtcact gaagttagtt tgactccagt gggggaaaca 127320
tagtgacgac cattttcggt agttacgcaa gtcagttcct taaacggcaa ggaatattgc 127380
tgaaatgtat gatgacgatt ttcaaagtca ttaagtttgc gcaaagcctg tagagaaacc 127440
attacatccc atccaaatat tttcgccaat caatagcatt cttcacttca tatccgagtt 127500
tgttcaaacg atctaagcaa ctttcgatga acttgacttt ggctttctgc tcttgaagca 127560
tgctagacaa ttcgatataa tcatcatctg cttttaccca tacatctata tcagatttca 127620
ggggtcgaac ttttaatggg cgttcaacat aaacgttggg cggcaattcc cctgcataaa 127680
atcggcgtaa atagagatct atttggcgaa atttgccagt tagatactcc agatatcttc 127740
cttcacgaat ataatggcgt tgcacagtca tccacgaacg accaattttc aatgacattt 127800
ggtctaagtt catgtcttca ggatttaccg aaataagagg ctccaattct gccattatat 127860
cttcggtttt catcgtttca agttttgttt cgctcatgat ttattccctg ctgtttcaac 127920
tctctgtatt ataacttatt gtttatcaat ttcgcgggtg acgcgagtcg gagtcagttt 127980
caaatatttg aacgtaacag tcgtgaccag ttggggaact gcagcatcca catccaccaa 128040
tacgttatcc aaagctgtgg gacgggcttc ttccaacaac aattgtagac caacaggtcg 128100
attcatgtta tcaagaaggt cgatggtgat atcacggcta acagctaaat cagatccagc 128160
attggacgca atccaattgt aaatctgttc ccagttgtac caactctcat cgataacgaa 128220
cgtaaatacg atggggtcat acgtgagacg ttctgaaggt atggagttga gcacatcgcc 128280
aggggatggt ccctcgatac cttcagaata cactccagga atactgaagt catgtattga 128340
acgagtaagc aatatcaggt ctccgatagt taagcgccat ttatcggaag ccgcgaaatt 128400
aggatttcg tttttgaatt gtacacctgt catgttagca cctttgctgt ggagaacgtt 128460
ttagtgttcc tgatacgcgg attcagaaaa tggatcatga cgatgataat ggtgcttgca 128520
ctcacaagtt gccgtatctt tgtcacgtcc gtcatttctg taaccgacct ctgggatcct 128580
gaaatcagaa ccatacctgt taacatctca gccgacattg ataaatgcaa taaaaatatt 128640
ctggatcaag tagtatctga ttttcagaac ttccagactc ttcaagctgt tggttgtttt 128700
gatgataaca accattcact gagaccatac tggaaaacca cgattcccct attgaggaaa 128760
ggtgacgaag gaaagatccc atatctatcc gcaagtattt attactctca gaataatagc 128820
atcatagcga ctttcaaccc ttctttcttt gacaaactca gaaggaatac tcaagcaagg 128880
gacgtagaaa tcaccagaga cgttgcaata tcatttcaga tagttaataa caccaaatct 128940
ccgatccgaa ttgccactca gggtgttttc gttaatggat ctgctgtagg taatgaaatg 129000
aacatctatg aaataagacc aggcggtaaa gtatggattc gaatgagtga tgttggggtg 129060
aactccctgg tgatggaagg tatcgaacca gtgggagttc tccccgctag acattaatta 129120
tttcagggac tcttttaatt ctggagtccc tattttatca ataacgcctc cagcgcagag 129180
atctttagcc cattctccaa gaacattcgc aaaagagaag tttagacatt ctttgatcat 129240
```

```
gctttcaatg tgagcaagtt ctgcggctat accatctgta atatcactta taaccccgtt 129300
gactgcggtt attgcctcat tgatatgtcc tgttacttca gcagccaatt gctgtagttt 129360
tgccatccct tctgaggcac cttccataat catgtcatac aattccgata tcttgtttgt 129420
tacggtctgc agagcacctt ccatagcatt cagccattgg cgtcctaaat cctgaacaac 129480
accaaaagcc ttgttgatca aatcacaatt gtttggttcc cgtgatatac ttttcaaacc 129540
tgatttatat gaaacggaag taccgatgcg agaatacgcg tcattgatac tttggtcgcc 129600
atatgtgttc agtgtcgtta tccccgtgtt ggcggcgcta tacatggtgg tggctgctgt 129660
gagtttttct ggtgttagtc caccagcaac catagccgcc tgcatctccg gagtcgcgtt 129720
ggcagttatc aatggtatat tggtactacc actggtgatt aaatcctgtg agggaccgga 129780
gagggacgga agcgggttgc taaatgcatt accagaggaa aggacatcgt agatttgtgc 129840
gttcataaaa tacccccaat tttgggggta tttataatca cggaagatga tagataaaat 129900
tctcgcagaa ctttttggtg tatttcttta gaaatataaa tttaggttcg cgtggtgtat 129960
ctttcagatc atttagtgtg atataactga ttcgcgccag aaagtacatg gtaaaagcga 130020
cacaaagaat caaaattaat tgcagcatag ctaactccat atgggtgtga aggcaaacat 130080
atttataaca atcgtttggt tttgggtttg cccatgagag tgatattgac attgacacct 130140
gctttttca tacgggtaat catgtcttgc gtcccagtag acgaaccatc ccataatgca 130200
attccaaaga cctcaagacc tttttgtttg gccagggttg tagctttgtc taacatatct 130260
ttgttacgtt gatttcctgc gcctttccca tatatcgtgt gataattctt agggatctcc 130320
attggtgtaa catgaacata attgatttca caccaatcac gagatatcaa gtccacacca 130380
accgcttcac cttctataaa agtttcgatc tcgtggggat ctaacagttc atccagtttg 130440
gcgaagattt tatcccgctc ggttattgag cgggaacctg taatgagcac gacatatttc 130500
ttcatagaac tcacagcgcc ccaagattgc tgatgacgta caggctgcac aagggagtcc 130560
ctgatgaacg aggttctatg ctcattcccg agaggcggat cagttccagc aaaccgtcgg 130620
tggtctgata cgcacgagtc gaaccgtttg gacgatatag ctccaactcg gttcgccctt 130680
cctttaatgc gttacggatg cgtgtgaata cgctgtgacc ttgatatttt tgacgtagaa 130740
tatctaaacg ggtgatgaga tttcgactgc ggctgcgacg tcccgttgac gaaacaacta 130800
atttcatttc tggtgtttta caagccatgt tatagtcctc tatttgtagg ggttgggtat 130860
gattttaaca tacccgttca aatggtttag aacaaattac agatcttggc actgatcgca 130920
atattcgtcg tatgtgaatg tctcatcaca caggccgtca cgcatcatat cggccttggc 130980
ttcgccaaat attttcaggg tgataacgtt gccgtctaaa tctttacgaa gttcgttcgg 131040
cttggtttct atgaagtcga acaccacaaa gaacccttcg gtgacatatt tgatggtttt 131100
gttgctcagc ttacggatgc caccattctt tttgaagata gaggtgcgga ggttttcgaa 131160
ttcggccaga ttgtcatcgt gattcttgat ggcgttcagc attgcgtcaa ggtcgatttc 131220
aggacgaagc attttgacct gatcttcgcg gtcataagaa gtgaaagatt ctatgttggt 131280
gatgcccaga gcgtttttaa caaacgcgtc aaatttggtg aaattgttga atgcccagac 131340
ggagattttt acggttgtca tgatgtagtt ccttcatttc agagtcagtg ttgtgctgct 131400
tatggaatga agtatacggg gtttattgaa gaagtaaacc ccgtttattg aataaatttt 131460
aaatttattt gaagcgatca ggaagagtgt cgtgaacctc agcgctcagc accaggaact 131520
tgccgtcttt agtagggaag cagtagtctt tcttgatgtg gcgcatgtgt tcagccgtag 131580
```

ccgctacaca gtcgttagtc acgtcggtct tctcacctac ccacatactg gttttggtat 131640
tcaatgtacc ttggaagata gtgcccgtca atgggcttgc tccaatcttt ttgattctca 131700
taatttctcc caagtccatg tttgcgcctt ggcttttccg actactggaa cgttacggtg 131760
catgtttctg aagctgcctg tctgataaaa acagatcctg atgcgttcat tttcggtatg 131820
ctgtgcccaa acatgatgac cgtcagggta tggatcatga ccagtgctac cgccttgtag 131880
ggctgttttg gtaacgacat aatgcccttg catgtaaccg aagaatccct caggggtgat 131940
ataaccagag tccgtttgcc aatctccctt gcaattagaa tacaagaaat gctttggcac 132000
ttgagtttca atggtcattt cttctgtgag gacgaacaca tcgccgactt gaagcagtgg 132060
taaattgttc atagtggacc tcagttaata cggaacaaat gtggatagcc accaggatga 132120
ccctggccag taacgaacac gtcgaatttt gaacccttga tcaggccagg cagattgccg 132180
gagtccagca attcacggat ctgctccatc gccaacatcc aggttttggc aggttcggct 132240
tctgcttctc ctcgattgag tacgagttca ccttcggaat agaacttccc gctgtccttc 132300
atatagtaca acgtgatatg aatgtactga ggggacggaa ctaaacgcca accgtcgtcg 132360
atcagatctt ggcgatcatt gtccagtgac tgataatcaa tatcaccaga tggcaaacca 132420
tagctgcgca tgtagcggaa cttctcaaca cgatctttca cgtcggagat gaagaactct 132480
ttcgtggcgg ggctgatgaa tatgtatttt ccttttgaca tgatgtagtt ctctcttcaa 132540
agtgataaat ggttgcgtga aagttgggta atgatggttc attacccatt tattgaaaac 132600
attaacaatt atctttagac tcgtcttcac aatttgggtg ataaaacgtt cccagtttag 132660
tatggatgac gtccatgtgg gcattgattc tatcgatgat atcgtcctgc tctccttgta 132720
tgttaaggat agcaccaaca agacctggat tgtgtgttga tttttcttca gaattagatt 132780
cgggaaattc accatctaat tgtcgacgaa tattgatcac attagtgagg atgtcaaaaa 132840
gacgttcttt ttgggtgcgg gaattaatga ggatttgtga cacggattgt tcagaggtaa 132900
tatttcgggt tgtcatgact gatactcctg ttgtaagaaa gttatatcgt acaacaggaa 132960
ttgttattga actattcgcg tattaaatcg ttacgataaa caatcacgca ttttgagaaa 133020
catatttcag atatgcgtat ttgtaacctt cctcggtgag tacacacaga tgtgtatctc 133080
gaccttttgg tacgttttta acatcaactc gtttacaaaa ccccagggag gccaattcgg 133140
cttctccaga tttagcaggt atttccccag cttcacgagg tccaaaccag aaaagaacga 133200
atagagtatc gactgcaccg ccagataatt gatgagacat tttaacctcc tttgataaat 133260
gagactttat tatcttacat atccctataa agaaaaaccc cgccgaagcg gggtttgtta 133320
tcaaaacctg tcgcttagaa cagagatttg atcaaccctt tacggaagta aacgttgcta 133380
tcctgagcaa taccgtcagc agtcacgtaa acctgcgggt cttggttagc cggaatctgt 133440
acgaacgggt tagcacagat gccgtaacgg gttttgaacg ccatacgcgg agcgaaggtg 133500
gtttcaccct gggtgcggta catttccagc ggcacatacg gcgcgaagaa gataccggca 133560
tccagcgcag ttgcgccttt gtatgccagg gtgatatatt ctgctacagc atacgggtca 133620
acatagacgc gcataccgtt ggacagaaca ccagcgaagg tctggccagt cgggtcaaca 133680
gccagtttag tgttttcctg cagaaccgga gcatagtcca gcatgccaga catcgccaga 133740
gcggatgcca cgttcggaga acacagaaca cggttgcctt taccacgacg ggtgtcaaca 133800
ccgataccgt tcgcttcaac ttccagcatg aaagtcagga acttccattt ttccagcgcc 133860
caacgaccgg agatgtcctg cgcgatatca acaacaccgt tggtaccgaa tttttgaag 133920 cgaacagcac tgaagttcat ggtacggatg aattcacggt tcatttccgc ctgaatttca 133980
gttaccatca cgtcagacag gatattatcc acgtcttcgc cgtgaattgc catcatatcc 134040
tgacgcagtt catggctgta atcagcgtac aggccgcgag acttggcagt aacggtcgct 134100
ttctgaacgg tgataccaac acgcgcccac ggattggtgg tagtacccag cagttccgcg 134160
tcggttgacg gcataccttt accgatagtg gtcacgacag agccggaacc ttcgatctca 134220
gcctgactaa agcctgacgg gtcgccagcc tgtacagtac catcaccgga atagccggaa 134280
tcggcttcct gcatgaacag ttctttacga gactgtgcgg tgttggaact gtcaccaaca 134340
ccctggcgag cgcgcagtgc aaagatctga ccgtcaggac cagacagcgg ctgaacaccg 134400
aagaagtcca tcgcgatgtt gatcggcgcc agacgttttg ccatgtcgat cagaactggc 134460
tgccatttac cgacagtgct gttcacagaa ccaggtgcgt cagattcgcc caggtttttt 134520
gcgttccatt cagcctggtt ctgcatcaga cggatggtta cgttttcggc agacagaggt 134580
tgaatagctt cagattcttt ttggagaact ggcagccact gtttgcgcat ttcttcggtt 134640
acaagtttct tagtcatgat gctcgttcct tacattgata ttcagttaag ttgaaattac 134700
ttagtagttc aaaatcaagc ccccttttcga gggctgtggc tgctaaaatt agccgttcag 134760
caaagcactg atctggcgac ggacggcttc gttgacttct ttgccaactt cgtctttgtc 134820
atcatcgtca tcgtcatcgt catcatcgtc ggcttcacct tctttcttcg gttttttacc 134880
ttctttgatg tctttttcag acttgtcgcc atccggcttg ccttttttcat tgtctttgcc 134940
gactttatca gagaagtcat ctttgccttc taccaggtta cggaaggtgc gcacacggga 135000
ttcaaattca gactcggtct ggaattcaat accttccagc aggttgacaa cagtgtcttt 135060
cttggtgtca accatacctt cacaaatacg atcaatgaca tcattgcgct ggcgtttggt 135120
ttcactttct ttgagctgag ccaattcagt attggcaatg ctggcgcgtt tctctgcttc 135180
agccaggcgg ttggtgagag ctgcaatctg accgtctggg tcagtggcga aactaacacc 135240
tgcttctttc agaacattag agaaaccagt gaggaagcgt tcagcagctt cggttttgat 135300
ctgagcgtca atggccggag catttttgtt agcccattct tcaacaaccg cgttgaggaa 135360
cgaatcaact ttttccgcca actgaagagt gaaattttct ttaaggtctg cgacttcttt 135420
ctggtgggct tctaccagag tcaggcgctc aacgttacca gccgcttcag tttcttgaat 135480
agcttgcaga cgggcggctt caactttaga ttccagcaga ccagatactt tgtccaagaa 135540
atcggtgctg aggccattaa cgccttcaaa cagtttttgc aattcaggtt tcatgatagt 135600
ttccttctga acgatttttc agtatttagt gagctgaaat tcagcccaga tgattcaatg 135660
ctgcatcaag gcggcgcagg aagtcgtctt ctacttgaat attggctttc accaactgat 135720
caacaacgtt tcctttaaca tcccgaggca tccaaatacc agaagcctca tcaagctgcc 135780
attcaacaga ttcactcaca gccttaacat aacaaacttg tccagaagga cggtcgactg 135840
catcaacagc ggtgagcata aagccaggct gaacgtcatc ataaccgttt actgacttgg 135900
tctcacccag gccacgtgta gacacggcca gattgaagtc tgcttcggcc aatgcacgta 135960
tgatttggcc ttttggtgta tttaaaattc gcgcccgacc gatggcatta gtgccttccc 136020
agcgaaggga ttcggttttg agcgcagctt ccaccagatt agggaaagga tagtcaggat 136080
gtgtgacttc accgattgcg cgacgatctt ggatatactc tttgtcgtat gcttcgacag 136140
caggaatacc cactttctgc agatcatagt tacgcccgtt acggttgact tggttacaca 136200
tcacaaacgg accttcgatg aacatggcct tcccaccagt tgaggttgtg gcctcaccga 136260
tttgaagatc cttccctatc gctgtgatct cacgcaacag tttcatcata aactccttac 136320
ttgttcttac tcagtcccat cattttgcgg aacttcatag ccttttcctt gcggcgctcg 136380
attttacgtt gatagcccat tcccatacgc tttttagagc ggagggcttt gcggttgccg 136440
atcttgcgaa cacgacgttc gctggcgtcc ataacttcac aacgtgaacc atcagccgac 136500
aatttgaacc caggggcaca tttcaagcgg cggcggcgtt taccacgagc gttcacttta 136560
tcgatgactc gctgctcgtc catacgagag gccaggaaat cagcgaacgt ggcgatctct 136620
gtgatttcca tcatgcatct ccttactggc cgttgttgtt tgaattcata tcagctgcga 136680
tagaatccag aacatatgcg gtgccttggt ttaatagttc ttgactacgt gcatcaagtt 136740
ccatgttgca ttctgcaaca gcagtttcag tgtcaccgtc aattactgca cgaacgatat 136800
caattgcgct catgattttg atctccgaat taattttcta tatttagttg aactttaaat 136860
actatcgtct gttgaaccgg agaatgggat agtctcaggt ttaaacttca acggactaac 136920
atctgaaccg ctataattgc cagtttcatc tgcttgaacc ttcggataga gacctttctt 136980
tttctcttcc gcgatcttcg tttgttgttc tttaacttct tcatcagaca tacgcaatac 137040
atttctcatg acgtagtcta tggagaaaat ggaaccaaca aatggctcaa cagtgttcaa 137100
tgaagccaga cgatcattca agatagcgtt ttcttgttgt tcacgaatgt aactatcgga 137160
tgtgaattca aactttataa acggtttgat cttctcattc caatcctttt catccgtaac 137220
gcctttcaaa attaactggc ggcgcaagaa ttccatgaag aaatgggagt aacggcgtcg 137280
taacccagca cagaacttgc tgaagcgcag ctcttcctgt gtaatctccg caaggttaga 137340
acccccaatg ttaatagatc cttcctcttg gaggcggctc ttagggatca ttagagcatc 137400
atagagtttt tcacggaaat agttcacgtg atccatttcg cccaattgat tcccaccccc 137460
aacagtcgca atctctgtag cattctgacc ttcgcggcgc ggcaaccaat aatcctctgc 137520
aatacccata agatgggcat tacctgttat cttaccagtg gtgcggtcat atgcgttgcg 137580
gtttttgaat ttacccatca tcatggtcat gtattcttca gcagatttct taccgagagt 137640
accgacgtca agatagaatg cgcgtttctc aggggcgcga gtgatggcat aaattacagt 137700
cgcatcttca gtcgtaacca ggttgttcaa cggacggata gcaggattta aaaggcctgg 137760
gacaatacca ttggccaatg gctcttcacc actatcgatg taaacaatgc tttcgtcatc 137820
gaatacgagt tcttgctgtg aaggctggaa gttctgggaa gtaccagatt ggccagtgaa 137880
ttggtttcga ttataattcg ggttgtaata atacttcaat gttacagatt ctattgcttc 137940
aataccgcct tcacgcatcg ccttctcaac gatatagaca ggacgaatgc aacgagaatc 138000
aagcataacc aatttcttga tcccgccttt tttattcgtg ggatcaacga tgacatgata 138060
tgcttgtcga ccgtcaacat accatttccg gatcttctga tatgctgtat tgtcaaagtc 138120
catcaagtgc ataacttctt tgaagcattc ggtgatagat tctttaacag tatcagatat 138180
cccttcaact ttgtcaaggt ttactgtcac tggagtttca tcttcctcac aggtgacaac 138240
atcattgaca ataatgtcca ccgctttgcg aatttcaggc tgttgagcca tggactgata 138300
ttcttccaca actgttttaa cgctgagaag ttcactctca acgccaacat agttgtaggt 138360
gtttgcaccg ccctgaagga ttatagaacc gtcttgagca tcgtccagag caacaactgt 138420
cgccttggtg agcaacaatt catcttgttt ttgggctaac ttatcggtgt cgactttggc 138480
attgactaaa ccgccgccgc caaacaaacc gaagaaccct ctgccgtatc cagccatgat 138540
ctaagtcctc aacattttct tgtaattagt gaggggggaa taacattccc ccagcaccga 138600
ggacattaca atgacttgtc agaaacggct tggaaataac gcaagtcgac agtgaactgt 138660
gtgtaagagt ccattgccga catatcgagt tccaattggc cgaggttttg aggccagcca 138720

```
ccctgcaaag tccatgtctt agtcacgttg tcattcgcgt ccagaagttc catgatgata 138780
tcacggaaat aatcatctgg attcgcgctg gcgcggttgt tttcactacc gttgatgaat 138840
tgctgccaca cttcaaaagc attgtatgga gcgttgttca ccacgttaat gaacgtcaca 138900
ggaagcgctt cgaaacgacg atcccctggg aacggaagtt cacgaccacc ccagggcacc 138960
agaatttcgc ccagctgacc tgttggggtg ttggtggtta cagccagcaa ggacacgtca 139020
cgaattgtgt cggaaccagc aacaaaagaa ggaaagttta cagtcacacg ccagcggtgt 139080
tggcgttgta cgccgccccc tcgtgacatg gctgcgcgaa actcattgac tgtcgccatt 139140
tttatatctc caaataagag tacacaattc taattagtcg tcaatctttt aatcttcatg 139200
gaagaaagat cgaaaccatg atgaacatta cttgaaacag gttcgatttc acacaattcc 139260
caacggggat ctatgagaga aacaagacca atgtgttcac ctgtggatgt caattttgct 139320
gcagttttac ccagcatatg acttccatca ttaccgcctt tattcatgtt gtaacccatc 139380
tcataagaat tatattgagc gatgagttgc ttctctaatt cccatttatg gacttcatcg 139440
gtctgagcaa ttacaacgaa agtaaatcca gatgttccat acttacgcat ggcatcatac 139500
aattcacttt ggactccatg atgaaaagca ttcgcaaaat gctgatcata tcttcgttgt 139560
gggtcattgg ttacaccgat gtagaccttt ccattagata tcgtttcaat tttgtatgcg 139620
tatatcattc aataactcaa atcaataaga caaaggaaaa ccccgccgaa gcggggttgg 139680
tcatttatga agcagcaacg atgccgccac cggattcgat ttccgagaat tccatgtccg 139740
gacgaacggc agcaaagtca agatacaccc aatttatgct gtattccggt ttcaaccaga 139800
taccagcaac catttggttt gccgcaatga catcagcagt gttgttatct tcatcacact 139860
tgactttacc atcgtaaatc gcgcccatat ttgccagctg gcgaatatat ggacgaaccg 139920
cattgctgaa cagaccacgt gtaaacgcgt cattgttctc accaagatag tatttggcga 139980
ttgcggcgat gttctgctca gccatgatga acagaccacg aacgttgatg cggtcaaacg 140040
ccgacgggcg ggtcaggcca gttttgtcac catacaggac gatgccttca ttggagaagg 140100
ttacgatgct gttgatctga ttgcggtaca acacagcacg ttcatcagaa gacgcagacc 140160
acgccattcg attatagttg ttgtatttac cacggttgtg gaacgccgga gatttgtaga 140220
tacccgcgat ttcaatgctt cgcgcccaaa cacctgcggt gccgccacaa gccggaatcc 140280
aacgcatttt gtcgttgtac ttgtcgtaca catatgccca gttatcatcc atgaagaaat 140340
aagaagagtc gcgaacaagg ctttcacgcc aagcaacgac atcatccatt tcacgaccac 140400
ggttgccaac aaccgtatca cggagcgggg atacgaaaga taccgtatct tttcgctcag 140460
tagataagtc gatcaatgct tgttgctcaa tcagttcttc gcagtacgca aatactggct 140520
tcgcatcata tgcttcagca ttgttcaaga cttggatagc cgccacgcgg ttgatgttat 140580
aatcgtctac gccgccttct aattcaacga cacctgcaac cagttcgctc gcgaaggtat 140640
acacccaatt tgaagtatcg ttgatcacgt ctttgaagta cgcattcgcg ccatcggatt 140700
ttttagaacc ctgggtgttc tgcatcagtt cgtatttttc aatgatggaa ccagaagcgc 140760
caacagtagt gattacggct gttgcagtca gtcctttgtc atcaggaacg atagctgtaa 140820
cggcctgagg accgatagct ttatgtgtca cgatgacagt gttggacttc acgacaacag 140880
aagaataaac acttgtcagg gaagttagcg ctgtaccgat tttggttgcc aaagtggctg 140940
gagtatcagt atccagatat gcgatatctt cacctgccac actgatggtg ccagcagcag 141000
tagccgtacc agaaacggag atacggtcaa cctgaccgac cgcgccagca gagtcggtaa 141060
```

```
tgcgaccaac tttgtctacg acaactacat ggaattcacc agactgaggt gcgtatgcaa 141120
agttattacg gaattcccaa gtcgagaacc cagcagcatc acaaacattg atagcaatat 141180
cattacccag ggaacctgga taacgaccag tccaagtgat ggacgccgaa ggacttgctg 141240
tttcaaaatc cagtttgttt ttgatcgcaa tcgctgtctg acctttggta acagagttct 141300
tggctagagg accaacaaca cgggtcaccc atgccataga gctgtaagac aaaaagtccg 141360
cgattacgag aaaatcggtc gcagtactgt cgttgggttt gaagaatttc ttcaccaaac 141420
ctgtctcacc accagtaacc agcactggaa gttcaacttc accccattga aatttgccga 141480
cggtcgcgcc ctgaacaaca acggacgggg acgtctgaag cgtggcatca cgctcagtcc 141540
actgaacgga cggcgcaacg ctgaagcttt gagttgccat aatatcattc cttctcggta 141600
gagtttcgct caatttgaaa gatatttagt gatcaattct taaaccactc atccatggtc 141660
atccctgaca tttcgttgaa aacttgaatg cccccgaaac caggcaaatg ctcagtttcg 141720
gatggggtgt ctccaacgac taaaccacca aatgggaata cctgctgaga ttcagttgaa 141780
gacattcggt ttctcatgtc ctgagaaata cttgtagacg tcaagtcact gaaccattct 141840
tgttttaccg cccatgaata taagaccaac ggcatgacac agtcatcgtg acaaccgtca 141900
tcggcttcat accgagcgcc tttgaagaca aatgtactga gttcatctat cgtgtcttgg 141960
tcttcgatca ccaacatttc tttctcaata agcgctttca ggttagcaca accaatagat 142020
cgcactttcc tgttggtgtt aatgcctggc tctggtttac gaccaccaat ccgtttcccc 142080
gtccctttgt tatccgtcga cgtgaatatg atctctggat actcaatttc ttgatacaag 142140
atcgtgataa cctgtccacc gacgtcgttg tttgtttcaa caaggacagg acattccccg 142200
tattcggtgc acatatcagc tatcgtgtat gcatacatca taggaggtat cgtgttattc 142260
ctgtacttgg ctgctatgac atgcggatat tcagttatat ccagaattgt taagacggaa 142320
taatctcctt ccaccccctt cccagtgtcc gcaatcccaa agtagagacg ttgtgggtcg 142380
tattccttat aaatcttggt gaattcatta ggttcccgat acaacttgga cgtcatttta 142440
tctaagcatt tggccggaat caatgaaccc acggaaccac ggaacttaat gccaaattct 142500
tgatcgaaac gagcatcccc cagacgagcg cgttgtttgg tttcccaatc agggtctttg 142560
gtgtacgccg gaaccttgta ccaagggact tcggtaagat ggaagtcgtt gtattgtgga 142620
tggcgtgggt cggcttttgt aacgatatcg tagaacaacc ctcgctggcc tttcggagta 142680
ctggtcagga tacaacgtga agtatcagca gatgcgatcg ctgggaatgt tgattcccaa 142740
aattcaaagt cattttcgat gaacgctact tcgtccacgt acaagagaga tacagaacga 142800
ccacgaatag agtccgaaga cgttgcataa gcatatatct tagagccgtt ctcaaactct 142860
atcagtgtag aaccaaactt ctcacaaccc tgctgaagga agaatgggag gtcctgatac 142920
gccttcctga tacggtcaag aatttcaatc gcttgtttct ctttgtttgc cagtaccgcg 142980
atttctttgt ctgagtggaa catcgcatac caaagaagaa acgcagccac gaccgtggta 143040
ttatggctga ggaacccatt cgtgtaataa cgttgatcgc tggacttgac ttgcaagtca 143100
tacatgtggt ggtactcacc agtctcccag atctcagaga tgaattctat tccctcctgg 143160
gtcattatgg catctccggc ctccatgtct ttagcaaata cttcgcgccc atattcattg 143220
aagaacatgt gctcatctgc gacatgaatt gtgcgtccgg tttcagtcct gacaacgtat 143280
tcagcgtatt ctttcgtttt atgagcggca ataaccggaa cccagccagt gtcggactca 143340
acaaaatatc gtttcccgaa acggctgtct acaaacttat tgtggttgcc aatggtattc 143400
agtggcacag catggttcgg tccttcgaag cgcttgtgaa gctcttctat ggtgagatgc 143460
```

aactcttgtt gactgattgt atcatagaca taaacaagag tatcaccacg gacgcattta 143520
ccggactgac gagcctggac gaccgcattg aatcgatagt cctgaaagtc atggaacaat 143580
tgtttctgat aatcatgcat atcgaaaagg ataaagcctt tatcgatcgt ggttatcttg 143640
taatagttgg cggcgaagta atgcgcgtcc attgaacatt caacgaattc gtcttcttgt 143700
tcatctgtca gcattaactc gactcgagga gcacgcacag aaggtttgcg catgaacgtt 143760
tggtccatac gcagtctgac gtcttggatt ttgaaacctg ttttctcagg tgcccaatct 143820
atttcttttt tataggccat gatggcttct ccacttcaac cacttagggc attcagaagg 143880
attccaaccg cctttgaatc tagcgattat tggttgtatg gaatttatgt atcggtcatt 143940
accaaagacc attctgcaca acacaacccc tttggatcca gacaaccaag cggaatatag 144000
aatatcagat ttcaaataga atgggatatt ttcttcatta aatctattca tctcccaagg 144060
cattaatcca agtttctttt cactcatggc cttcttggat tcttctgtat gggatttacc 144120
ataaaatgga tttaattcac gcaaattttt ccctgtgtta gacttagaaa ttttatccct 144180
tgtctctttg gatataatgg ctccggaacg aggatgtcct tgttccttcc atcttttctt 144240
taaagatgca gaagccttca atctctgctc ttgactgatt acagaccctt tgtttcgttt 144300
cgaaagtttc tccctaacat ccttcctgaa cattggattg tctgacttca ttctttctga 144360
agataattcg cttattttag aataaaattc ttgtttagat tcttggtata atctagatgt 144420
tctcaaaaca cccatagtgt tcttcataca actgaacgcg aacagcatct ctctggtgtt 144480
agttattttc caaagaagta aatggcaaat gaaatgcgct ttgggggata atctaaccaa 144540
gttatcctta tcttgtgtga aagaagggta caaggattta ggaagaatgt gatggacttc 144600
ccctcctgtg ttcacagaac ctttttggat aacaaaattg tatcgcctaa tcaggcgata 144660
catatctgga taaccctttt ctaaaatatc aattgccttc tgatacgcca tcgtcttctt 144720
ccttcacatc aactgtttca ccatcaatga tttcatcttc tggttgttgt gcggcctttg 144780
cttgtgatct ttcttcagcg cggcggcgtg catcttcgat cgtcttcaat aaatcgcgag 144840
aagatcgcgc ctttttccca accgatactg ttgttgttcc gtctggtgaa gttgtaacat 144900
ccactgtcgt gtcatcaaca ggtggttctt tatcacctgt cacagctttg atggtttttt 144960
ggttttccat caggtcttta ttcagacctc gcatgagttc acccaattca cggaaaacag 145020
aaaatgctcg cggagcttct gtggatgcag ccaatttagc ggcttgtccc atcatgaaca 145080
ttgtggcttc ttgcatggca tatgttgtgt cgcgtatccg tttgtaatcc gttgtagcat 145140
cagtgtccgc aaactcaggt actttggatt ccttggaagc aatatcctcc aatgaaggcg 145200
gttcaggaat cggctgatac ccttccggac gttcaccaaa ccattcacct gtattttcat 145260
cgaagtcaat acctggacga ggggcgacag cctccatcgc ctccttccca acttcgtctc 145320
gggcggtcac tgcatcaagc gtggcgagta acctttctga catattgctc atgatcaatc 145380
ctccggatga tgtatgccgt ctttatcaac tcggaaccac tcaggaagtt ccgaccatgg 145440
catgttcaaa tcattagaca tttcaataat tatctctttg atgacgtttg gatcaccacc 145500
gccagagcca tcatcgaccc aataatcttc gccataaatg tgtccatgta attgaaaatt 145560
aaaggtgcaa tctatatggg gtgattctgt tgcgtctcct tcccagttgt cagaaatcgt 145620
gtgatttaac aacattatct tcacgttctg atcttgagat aaagtatcgt tgtcctttat 145680
ctgacagtca acagaaggag taaacacaga ataaatttgt tctaatactt gcaacatttc 145740
gaccaatttt ttagttctga tattgtattc aaaatctata atgatcggaa tgcgttgctt 145800

```
ggaccgtgct gtggcggtcg atatttggtt gtggtatgac ttcgtcacct gtttattgat 145860
ttcgaactga ccaaaggaca ttgttgcaaa tggcagcata ttggctggca cgttcctgtt 145920
gaggtcatta cggcggccaa tggccatatg cagcgggatt tccatcaagc cacgttcggt 145980
tttgactttt aaatctgaca tgatagcgtt gaacacatgt atgtatttca acaatgattc 146040
atgatagaaa tatttttcaa atggtctggc catgattatt ccccgaagtc tatcttcatt 146100
ttattgggcg aaagatcttt ctctatttcg tccgcaaatt ggtatccgt ttgcaggctg 146160
gcgtctttgt acacaccgtc tccttccaga tcctgcaatc gtttatcaat atcgtctatt 146220
tcagatacac ctgtatcgaa atcttcgtta ccgtattgga acaacgtaca tggtagggaa 146280
tatgtgtacc atttcccaaa ttgcatgaat tcttcatcgt tattcgggtt attcacttta 146340
aatattttgt tagccatagg cagatatatc aaatcacctt cttgaggcat ttgttcaagg 146400
cctggaccat taccaataac ttctgaaaaa cgacgacgag caatagtgaa ggtcacttca 146460
tcttgtaatt ggataccgcc gaacttttcc cacatctgtg tgttgaagcc ttgataatcc 146520
tgcatataca cttcgatgtc aaacgcttgg tcgaatttgt gttcggcctc gtttaaaatt 146580
gggtattttt caacaataga acgtgggata tacttgacgt caatcccacg caattgtatc 146640
atctcgacca ccaagtcatc aattaatttt tgagtacctt gatgtgctgt atagttgaaa 146700
tattttgaag tagccatgac tttaccctca attttgaagg tatttagtca atcattaatt 146760
cttttgagga attgataaat gaaggttgaa gatattaaag aaactcgtga cggaaggcgt 146820
gtgagaatta tctgtgtaga tgctaaaatc gccgatggtt catataacat tgtgggtctt 146880
atcaaaggcg aaaaggataa tgattttatt gaatggtggg acgaaaagaa cgtggttgat 146940
ggttatattc tagcaaattc agatccttcc ggacgcgaca tcaagttata aaaagaaagg 147000
cgggttatcc cgccttctct tatcccatca taaaatcgat agggtattgc tgaccagtac 147060
gcaattcttc ctccagccgc tctatctcgg tctcggcctc actgaacata ctatcaccat 147120
ccagttcgat accaccaggg agacggatgc ctcttgcctt tttaagcacc tctgcccaac 147180
ggcgcttgac caatgcagtc gcatacgctt tcaaccacat atcattccat gcttcagcgt 147240
tttcttccga ttcggggtcg atattttgat aacaacgaaa agccagagtt tcatcaacaa 147300
tggcagcaaa ctgcgggtaa aggcgtcgct ggaacttctt gtacacaaaa ttacggcgaa 147360
catttaagac gcttgtgata tccgacaggc gttgttgcat ggaaacataa tcaatgagac 147420
gaatagaaac cagcgctgct ttggggacaa gcattgcttg agccatttgc cattgaggag 147480
ttgcccagtt tccgattgac tcaataggag gtccagggat aacttcaatc acatcgtcaa 147540
tatcatcggg aaattctata tatcccttgt cgatatcttc ttgtttaact tggtacagga 147600
agaacgcatc ttggctacca tcacgatgat attcccaaaa tttctgcaga gcatcatcga 147660
ctgcatcttc gacttgtgaa ctgtcaaggt taatttggat cacaggagcg cccaatttac 147720
gcaagacata attcataaaa gatttttgt ctcgaatctt attgacggcc attgttattc 147780
cccttttgct gcaaatcaga tacagtaatc cgcagtgtgc gaacatcatc tgaaagactg 147840
ctgctattga gttttaactc agccatgttt tgtttgacat atgcgaggtc agtattcatg 147900
atcgccatac gttcactcat gtcattcact ttctgaagaa cttgatccat cttgttggaa 147960
tctcgttcca atacattcac gcgcgtttcc atcccgccca tgaaccaaag gaacgatgct 148020
gccgagacca atgcagaagc cacgacagcg gttaagatac cacggatgtc aagccccgtt 148080
ctttcagctt gcgtcgccat tctgacctcc ttcggggatt tcgatcccca acttttcggc 148140
catcattttg attgtcgcct ccagattaga tatctggttt gattgttcaa caatggtggc 148200
```

ttcacgggtt tcattgcgtt gacgggcttg caatgcagcc atgccagcgg cgtgatcggt 148260
gcaaataatc gcgccagggc aagaactgct tctcaacatg gatgcgtgcc cctgtacttt 148320
cactccacgc atatctttat cctctattgg tttggtgggc tttacgccca cctttcaaca 148380
ttatttatgc cagagcaata agacggaagt ctttgaatga tggaggagca acgcggttcc 148440
cccgtacaag cgctcggact ttcaggccaa caaacgggtt attgctcgcc acagtcttgt 148500
catactcata ttcaaagaat gtggaaccgt cgttaaccag aggcgaagtt ggggtgacgt 148560
cttcccaagc cacactatcc atctcttgcc ctgctcgtag aagtttcacc tgcaccttca 148620
tcgaagactg agatgggagc attgcaccaa agaacaactt cacagtagaa cacggattat 148680
caaatccgat gtcctttgtc acgtatttga agacatcttc aaatggatcc acaccgtatg 148740
agttgaagat tacgctcagg tcatcgccat caatcattgg agcagtgtac acgttgtttt 148800
cactacgagt catagtagca cgaatctgga agtcaccaac ctgacgatag ataccttcag 148860
tcggcaatgc cacgtcagtg tcagtttcaa actcagccca atcagacata gaatttgaag 148920
tggcatcgcg ataacggtat tccaatttca gaattgaacc ttccagagcc gaattggtaa 148980
cgctggcata gaacatatca accagataat tgcccaagaa agaagcatta tctccaccga 149040
tttgtccatt gctgtctgct gccgtaccga cgtcaatctt gaatgaagta tagctcgcat 149100
ctgtcacagt aaacgttttg ttaagttgtt caggagtaaa gccacaaccg cctgtcaatt 149160
cagaaagagt gacattgttc ccagcaacca aaccatgacc aggtgcaaac acagtcacaa 149220
cagaagaccc gcttacgcag ttcagagtgt tcaatcccaa cggacgttgt tttggcccga 149280
gcttcggatc aaatgttaca acgttctgtc ccgcagcgaa gttacaacga tatatgcgga 149340
atttcatatc agccatttgg tttggagacc atgtagaacc gtttgaagaa gtgaagaaca 149400
cccctgtata cggttgtttg gcgatatatt cgttggacag aaggtttttc ttgcccattt 149460
ccgcgatata cgcgttgtaa tcctgagtat tcgccaacaa aacgatagca aactcagtcg 149520
atgcttgcag atacaccgga taatcaaagg tgaacttcgt accgccggaa gagtctgtag 149580
agatcgtcac ttcagacggg ttcaaagttt tacgagtaat gactgtatga gaaggtaagc 149640
cattctccat ctcgcgaatt tccagagtga tcggaacatc acgtgacttg gtagagaaga 149700
atacttccac gccttcaata tactcgccgc caatcttagt cgccaccata aacgattggg 149760
caatcggatc acgccattga tcaacaacca cttcagaagt agaagtttcg gtgcgagtac 149820
tggcagtgta acccaggaca cgagtgttga caaaggtctt ttgaatacct tgtttcttac 149880
cgaaagattt atgaacaatt tctgcattgg tcagtgtatc atccgcagat ttactgtcaa 149940
cagggctatc cgttaagcgg aacacgttgt cgcctgtgtt gaacttgatt gtatcgttct 150000
gtggaacgcg gaatacacct ttaacagcac cattggcatc agtggtgatc gggtctccga 150060
aattaccgcc attcggtttg caatacagat tgacgtcacg accagagaag aacgcataca 150120
tacgagtgaa aggtcgcagt ccagatgcgt cgaaagaaat atcgatctcg cgcatgtatg 150180
ggataacttg cgtctccaca atctgttcac cagtcatggt cgtggttgtt ttgtccgtgt 150240
atgtatatgt ggtgacatca cgggcagaaa cagtcgtgcg gtaacgatat ccccaccaca 150300
caccaccagc accatgcggt tcccaaacac gatcagaaac agaaacagta cgccatgttc 150360
catacactga accttcttgt acagtaccac gggtgttgat cgtttcattg ataatacgcg 150420
gcgcaacata atagttttcg aaccagtagt ctgtggtcgg gttaatcttc aagaaacctt 150480
cccaattgaa tactgcatac gggttaacgt tgatcgtcgt cgtcgcatat tcttggttca 150540

```
ccgagatttc aggcgtgtaa ttgcaaacca ccatcccatc catcactttg ttccagccaa 150600
ccggagtcat gtcaacaacg ttttgttgta caaacgggcg cagacgtccg ttttcggtat 150660
cgatagaacc catccaatct tcagacaagt catcaatcaa ccggaagtct ttgaacggat 150720
cagccgcaat accatttttg aaacggggat tgcccgtgat ggggtcgaac acttgctgtg 150780
tcatcgctga agattccagc tgtgacagag aggtatagta ttcaacattg gaaatacggg 150840
tttccagttt accgatatcg cgcatcgtat aacgacgatt atcaatagtg cgaatttgga 150900
tatcatcaat attcggtgta tacggcggga tcaacaattc atacaaacgc atggcgttcg 150960
ctgggattgc tggagaagcc agattattag aactaattcc tcgagccaca ccaaacacac 151020
cgttgtctgc cagataaatc gcgtcgatac gcggcagata atattctgtg tccagaataa 151080
ctgcagtgtt tggacgaacc atatctgtgt cagaagttcc gttggtgatt ttcggacgga 151140
aatccaaact atctgccagg ccgtacaccg cgcctgatgt agatgatgta taattcggga 151200
tatctttata atccatcgaa gtatacgaat cagcagagaa gaaatcaccg gaactgtggg 151260
cgaagtattg atacaccact gtatacgtcc ctgagattgc tccagcgctg gatgacaagt 151320
tagacttgta ataccctgca tcacgttgtc cgccatctag gacgaagctg gaggtcacgt 151380
ctgcgccagt atcgtttttg accgacacca atttccaacc atcgtgattc gccaaagggt 151440
ggctagtctg cgaggtgaac gtcactgttt cagttgtttc agtgatggtc ttcgttttaa 151500
ttgtggccgt ggtacgaatc atcagcgcca gcaaattgat tgactggtta gcattaccac 151560
tgcccagaga aatctgcagc gccgaaccga ccggagaacc agtcaaagac aaagaaccag 151620
agatatcgaa ctgcgcttca gaaccatcag atttcgctgc agagtacaac gaaaattctg 151680
gggaaaaact atatcccaat ggagcagaaa tagaacccgc gccgctgttg tccaacgtca 151740
ctttatacgt tctgagaaca gtgtagttga tatccacgga gccagttggt gctaaagtct 151800
tgacaccgaa taccggaaga gagaagatca gatctatcat agaactctgg ttaaactgat 151860
tggattccag ttcagcagag aacatggtga taccgctttc ttcgtaagac actttggtga 151920
tagtggatgc atcgccagta acgaccaggt cgcgcatata cagacgaaat tctgttgaat 151980
tacgttcagc tgatatacaa agtgctgtag cctgggtaac gcctgaagca ttcagtaatt 152040
tgtatcgaac ggtgcgggat atcactggca cacctttaga attcttagtg accagataat 152100
tgcctgtggc caccgcaaca ggggtgttgt tcaggacatc ggtatcccgc gccttatcaa 152160
cgatcaccaa ctcttccccg acgttttcga tacggcgacc gcgaacatag gaaatacctg 152220
gtttcattac agacacgaat ttactttcgt cgccgccatc agcagcattg aatacaccac 152280
cattgttatt gactttcagg tgttcgcgga tgtcgatctg gtgcgttgaa acgttgtaat 152340
cgccgttggt ttcatacgtc cgttgggcca acgtgtcttc cagaatatta taggtggact 152400
gagtcaccat agactggatt ttaccatcac gaactttggc cagttcaaca aagtcttcaa 152460
ccacagcatc ataatcaaat cgagataaga ccagatctat tcgaagacga tgagcgcctg 152520
gggctttgga gttaatcgtt ccctgaacat ttgaataaag ggattcatct tctgtttcag 152580
tgacaatggt ttcggtgact ttaaatccga tgcggtggga agtgatgtta gaagttttgt 152640
caacgataag agttgcgtca tcaacgtcta ggaacatccc acgaatgaag taaacgcctt 152700
tcgtcatacg agcgacgata gaaccagtca ctgcagctgc gataccataa ccaatacgaa 152760
tgaaattatc attcacgtcg taagtctgga aatacagatt atcgttaaca tggaatccgt 152820
cagcattacc cgcttcagtc atctcaagga tagccagcat cgtatcagga gcagacagat 152880
cacgttcaag agacaacaca cgcgctttgg cattattgtc cttccccaaa acgtagagtt 152940
```

```
cagaaatacc ttccagatca gtgaattcag taccacccgc caaagtgaat ttcaaagaga 153000
ctgcggcgtt agtgatcgtc aaaccgccag ggataaccat agaaccatct ttgaacaaat 153060
ggttgcccag tttttcaatt tgatcctgaa gaatagtctg catctggttc agttcgcgag 153120
tctgaacctt gataggcatc ggacgaaaaa gaatccgtga aaaacgtttc ccaggattcc 153180
agtcatccca atacgggcga cggtttaaat ttgtagattg cattttgatg ctccatcgag 153240
tgccatttta tagagatatt tagtatacag ccaacaaaca gatagaaata aaaaccccgc 153300
attagcgggg ttttatttta tgctgctaca gatccagcaa ctttccacac accagaaccc 153360
atgtgaatcc atttatatgg ttgcccagca acaggaatag ctagctccca tcttgcaccc 153420
gtaccgaact gagtaacaga agcatcagga gggtttcccc catagacatg tgcaatacca 153480
ttaatgaggt agccggttgc agtccaggta actgtccccc agatagtata attaccatta 153540
tagtgtgaga agtttaacca tgatgttgct gccccccaaa gaactctaga tgcgtcagga 153600
gccactgtgt tatcgagatt aatagtagtg tcaccaacct gccagtattt gctagtatgc 153660
gagccagaga actctggtaa gtaacttgcc gtgattgtaa cgccacactg tgtaaagatg 153720
catgcaacca caccagtatc cacaaggtta acaccacgga atccattaat agctatacga 153780
gattgattac actcaaagaa gctaccgtga acctcttctg ctccacatcc gtccatcact 153840
acactagtgc aacctaagaa tacataagcg gaaccagtta cataatccgc tgcacaacct 153900
ttaagagtgg aataagtaat gttagtaaac ttatatgccc aacgggatac attcctgaca 153960
taaacattat ttaagttaaa agttgtacca ccagtatcta cagagatgcc atcttgaaca 154020
tctttgatga gaagtgaatc aaacgcctga agccaactgt cactagttct gtagccagtc 154080
ataacatgct caatatacaa atcctccaat cgaaccatat aactgataga gctataaata 154140
ccataggcat tttttgcagt agcagcgcca atcaggctca tcccagttat tcctccggaa 154200
cgactaaagt taccagtcag atcccctgca acgctactat ccatatcaat ggcagcaata 154260
aagtcaaggg agaaactatg cggtgcgcct tgccatatgc gatctggaac ggttttaatg 154320
tcgttacctg ttttgcgaag gccgcaagaa tctctaccca ccccctccca cataactcgt 154380
ggcgggcgaa ttgctccgta cttaatatcg tagaaacctg agaagcgtaa cttacccccca 154440
gtttgaggaa gacaagcatg aagcctttca agagcatcgc tgttttgttc ggccgttctg 154500
gaggtcatca tgccaccatt ctcaaccgga atatctatgt agcttcccgt tcgcttccag 154560
cgttttcctc ctgccgttac aaagatatta actccatcgt cagcttcgga actggcaaac 154620
gccataaatg ttcctccacc aagacccgga gaatcggaat aatacccaag gactgttata 154680
tgttgaccaa tatatgaagg ttcagttgtt cgtagaacag aaatatctga gcaaatattg 154740
atatctggtt tacccaaaac tacccaagta tcattattta caccaccagc actatcgacg 154800
gtttcacctg cattaacagt ttttggtaaa gaaccagccc accgatacaa atttacccca 154860
tcactcacaa cttcgttttt gacacgaatc gtaaatccag aagtaaaatt ttcaacaaga 154920
gtaacatact cttcccttaa cacagccaat gcacccaaat ctacggtgcc tccagagtgc 154980
gtgagaatgc cgtcgactaa actagtgacc gttacagtac caatgttaga agggagagcg 155040
taggcacgtt gagatacctt atcgtagatc actttataac cagacaagga ctgtcctgat 155100
ttggcataaa caacctcaga ttgcttaaca ccaaagtgtc tggctactgc ttgtttattg 155160
gttaagattc cagtcgaacc tttaccacct tgactaaaca tttcgttcat aagtacctca 155220
ttgtttttct aggagaaacc cctccgaaga gggggtaaaa attaatttac tctataagta 155280
```

-continued

```
aaagtcacac gtaaattttg ggcagtaaaa ttaactgtac catctgggtt aataatccaa 155340

attcgagcac tatttgcact gacattcata acttgtacat gcaattttgc ttggtctaag 155400

gtaggagaac tactgttcat ttgggctaca gcatctatta cagtatacct tgtagtatct 155460

aagccagatg agaataaatc acctgtagta acacttgcag taagggttac agtattagtc 155520

tggtatctag atactcccgc ctcttgctga atggttctac ctctataagt acgagaacca 155580

aagaaaatat taccaatcgc tgtaccaact gaatcaacag aagcatcaga aattaatgac 155640

ccattgcatt gaacagaacc gttaatacca tcagtctgtg ctatggcaaa acactctgta 155700

gcggatgctg cactaaattg aataccccag agtcgtccac catttaggac caagttacca 155760

ttggaagtaa tgtgtatacc atacatacgc cgtccagtaa catcaccacg ccaagcgtat 155820

aaatcaggct cattaagggt tacatgccca ccaataataa agatacaacg tcttgtataa 155880

atagattctg cacctaaaga actagctaca agaccctgac aactttcaaa tacatatggg 155940

gctttagatg ccgcatccgc tgcggaggga ttagacgaac ctgctgcgtc tactccacag 156000

gaagacagtg tagaataatt ggctccgtat agtttaatgc cccctcact agtatgccca 156060

tatactcgtt ctagggaaat agatgtagaa ccccccctac ccgtaccatc attagatagt 156120

aagaaactcc attcagcatg ttcacgtaaa tctaagtctc ggaaagaaca catccacaag 156180

ttatatgaca taatgccata atttgtatac caagtacgta ctctttccac ggttagaaat 156240

gctgcttccg gtgcatagat tgcgtgagct accttacctg tagttactcc ggttgtacca 156300

gctataccat acagttgaat atcggagata gtagttctat acggataacc tgtcccagaa 156360

gagaacactg caagaataca gttaacatta cgcggaagat ccctaacagg agaattggta 156420

gtgacttctg tagtattagt agaagaagtc atctgaatcc tggtggagga ttgagatgca 156480

ccgcgtaaac taacgccatc ccacaagata atgggcttac tagttaagta atcaccatca 156540

gggaaaaaca gtacagatgg tctgctaaac atagttttag tggttaagtc tccaagatat 156600

gacaccgcta attgaatagc ctcagtatca tcagttacac catctcccac agcaccaaaa 156660

tctttaacgt tatagtagtc tttaaaatga ctatcaatgg ttcgcttaat tgcagaagaa 156720

acaccagata aaccagaatt tactaacgtt cccccatcag tagccatagc cgttttatac 156780

gcctgcaact cattctccac tggagttaca tcattaggtg cagggagcag gtcaacaaca 156840

accccaccag gattgtatgt taactggtta ccattaacag aagaaataaa tacattcgta 156900

ggtaatgtag gtaaaccata actggtttgc gtcgctatgt cataaacaac tttcttccca 156960

tccaataaag atatggtgtc cgtactaacg atgacttcag agtctttaac attagcagaa 157020

cgggcaattt cttgaatact gcggtcaaac aacggactga tattcggttg tttaacagac 157080

atttcagcga ctacccaaac gcctgcagtc agtgcagttt gcaaagacac tttccctgtc 157140

gtgctgttat aggaatattc aatttcgggt gttttgtact cgccaccgat ataaagagat 157200

tggactccat aagatgtgaa atcaggagtg aactcggttt cacctcctac ggcttgaaat 157260

ttgtatatgc ggataccttt ggctgtatct tctggcgaaa gaattttatc gaataagcaa 157320

tacacaacat cgcctttgga caatgcgcgc ccgagattca acgtatttcc ttcgatttca 157380

aagttgtcta ac                                                     157392
```